(12) United States Patent
DeLuca et al.

(10) Patent No.: US 7,915,242 B2
(45) Date of Patent: Mar. 29, 2011

(54) VITAMIN D RECEPTOR ANTAGONISTS AND THEIR USE IN TREATING ASTHMA

(75) Inventors: Hector F. DeLuca, Deerfield, WI (US); Rafal Barycki, Madison, WI (US); Moisés A. Rivera-Bermúdez, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1747 days.

(21) Appl. No.: 11/059,313

(22) Filed: Feb. 16, 2005

(65) Prior Publication Data

US 2005/0182033 A1    Aug. 18, 2005

Related U.S. Application Data

(60) Provisional application No. 60/545,347, filed on Feb. 17, 2004.

(51) Int. Cl.
*A61K 31/59* (2006.01)
*C07C 401/00* (2006.01)

(52) U.S. Cl. ...................... 514/167; 552/653

(58) Field of Classification Search .................. 514/167; 552/653
See application file for complete search history.

(56) References Cited

U.S. PATENT DOCUMENTS 5,086,191 A    2/1992 DeLuca et al.
(Continued)

OTHER PUBLICATIONS

Fujishima, et al., "Design and synthesis of potent vitamin D receptor antagonists with A-ring modifications: Remarkable effects of 2alpha-methyl introduction on antagonistic activity," Bioorg. Med. Chem., 2003, vol. 11, pp. 3621-3631.

(Continued)

*Primary Examiner* — Sabiha Qazi
(74) *Attorney, Agent, or Firm* — Foley & Lardner LLP

(57) ABSTRACT

Various compounds such as those having the formula I and XIV where the variables have the values described herein antagonize the vitamin D receptor and are useful in treating conditions such as asthma and in preparing medicaments for use in antagonizing the vitamin D receptor or treating conditions such as asthma

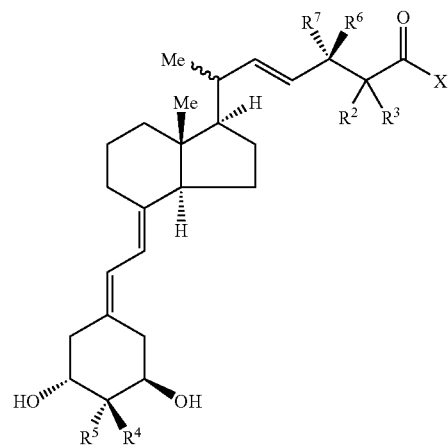

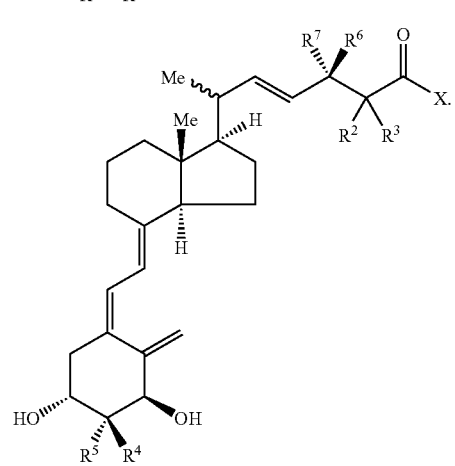

36 Claims, 11 Drawing Sheets

U.S. PATENT DOCUMENTS

| | | | |
|---|---|---|---|
| 5,246,925 A | 9/1993 | DeLuca et al. | |
| 5,536,713 A | 7/1996 | Deluca et al. | |
| 5,585,369 A | 12/1996 | DeLuca et al. | |
| 5,587,497 A | 12/1996 | DeLuca et al. | |
| 5,843,928 A | 12/1998 | Deluca et al. | |
| 5,936,133 A | 8/1999 | Deluca et al. | |
| 5,945,410 A | 8/1999 | DeLuca et al. | |
| 6,376,480 B1* | 4/2002 | Kirsch et al. | 514/167 |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,703,380 B2* | 3/2004 | Raskov | 514/165 |
| 2004/0220418 A1 | 11/2004 | DeLuca et al. | |
| 2005/0070511 A1 | 3/2005 | DeLuca et al. | |
| 2008/0261925 A1* | 10/2008 | Clagett-Dame et al. | 514/167 |

OTHER PUBLICATIONS

Baggiolini et al., "Stereocontrolled Total Synthesis of 1α,25-Dihydroxyergocalciferol," *J. Org. Chem.*, vol. 51, 3098-3108 (1986); published by American Chemical Society.

Casimir, D.A. et al., "cAMP Activates the Expression of Stearoyl-CoA Desaturase Gene 1 during Early Preadipocyte Differentiation," *J. Biol. Chem.*, 271(47), pp. 29847-29853 (1996); The American Society for Biochemistry and Molecular Biology, Inc.

Chomczynski, P. et al., "Single-Step Method of RNA Isolation by Acid Guanidinium Thiocyanate-Phenol-Chloroform Extraction," *Anal. Biochem.*, 162, pp. 156-159 (1987); Academic Press, Inc.

Cohen, P. et al., "Role for Stearoyl-CoA Desaturase-1 in Leptin-Mediated Weight Loss," *Science*, 297, pp. 240-243 (2002).

Collins et al., "Normal Functional Characteristics of Cultured Human Promyelocytic Leukemia Cells (HL-60) After Induction of Differentiation by Dimethylsulfoxide" *J. Exp. Med.*, 149, pp. 969-974 (1979).

U.S. Appl. No. 10/613,201, filed Jul. 3, 2003, DeLuca et al.

Dame et al., "Monoclonal Antibodies to the Porcine Intestinal Receptor for 1,25-Dihydroxyvitamin $D_3$:Interaction with Distinct Receptor Domains," *Biochemistry*, vol. 25, pp. 4523-4534 (1986); American Chemical Society.

Daniewski, A. R. et al., "A Novel Silylcopper Catalyst for the Reductive Bromination of Hajos Cione. Improved Preparation of a CD Synthon for the Synthesis of Vitamin D," *J. Org. Chem.*, 66, pp. 626-628 (2001); American Chemical Society.

Fujishima, T. et al., "Design and Synthesis of Potent Vitamin D Receptor Antagonists with A-Ring Modifications: Remarkable Effects of 2α-Methyl Introduction on Antagonistic Activity," *Bioorg. Med. Chem.*, 11, pp. 3621-3631, (2003); Elsevier Ltd.

Green, H. et al., "An Established Pre-Adipose Cell Line and its Differentiation in Culture," *Cell*, 3, pp. 127-133 (1974); MIT.

Hanessian et al., "Total Synthesis of (-)-Reserpine Using the Chiron Approach," *J. Org. Chem.*, 62, pp. 465-473 (1997); American Chemical Society.

Herdick, M. et al., "Antagonistic Action of a 25-Carboxylic Ester Analogue of 1α,25-Dihydroxyvitamin $D_3$ Is Mediated by a Lack of Ligand-induced Vitamin D Receptor Interaction with Coactivators," *J. Biol. Chem.*, 275, pp. 16506-16512 (2000).

Herdick, M. et al., "Mechanism of the Antagonistic action of a 25-Carboxylic Ester Analogue of 1α,25-Dihydroxyvitamin $D_3$," *Proceedings of the 11th International Vitamin D. Workshop*, A. W. Norman, R. Bouillon, and M. Thomasset (eds.), pp. 259-262.

Kutner et al., "Novel Convergent Synthesis of Side-Chain-Modified Analogues of 1α,25-Dihydroxycholecalciferol and 1α,25-Dihydroxyergocalciferol," *J. Org. Chem.*, vol. 53, 3450-3457 (1988); American Chemical Society.

Lythgoe et al., "Calciferol and its Relatives. Part 22. A direct total Synthesis of Vitamin $D_2$ and Vitamin $D_3$," *J. Chem. Soc. Perkin Trans. I*, pp. 590-595 (1978).

Lythgoe, "Synthetic Approaches to Vitamin D and its Relatives," *Chem. Soc. Rev.*, vol. 9, 449-475 (1983).

Mackall, J. C. et al., "Induction of Lipogenesis during Differentiation in a 'Preadipocyte' Cell Line," *J. Biol. Chem.*, 251(20), pp. 6462-6464 (1976).

Mandrup, S. et al., "Regulating Adipogenesis," *J. Biol. Chem.*, 272(9), pp. 5367-5370 (1997); The American Society for Biochemistry and Molecular Biology, Inc.

Mascareñas et al., "Studies on the Synthesis of Side-Chain Hydroxylated Metabolites of Vitamin D. 3. Synthesis of 25-Ketovitamin $D_3$ and 25-Hydroxyvitamin $D_3$," *J. Org. Chem.*, vol. 51, 1269-1272 (1986); American Chemical Society.

Miyamoto et al., "Synthetic Studies of Vitamin D Analogues. XIV. Synthesis and Calcium Regulating Activity of Vitamin $D_3$ Analogues Bearing a Hydroxyalkoxy Group at the 2β-Position," *Chem. Pharm. Bull.*, vol. 41(6), pp. 1111-1113 (1993); Pharmaceutical Society of Japan.

Mincione et al., "Improved Conversion of Vitamin $D_2$ into the Windaus Ketone and its Regioselective Hydroxylation via Organoboranes at $C_{26}$," *Synth. Commun.*, vol. 19(5&6), pp. 723-735 (1989).

Nishii et al., "The Development of Vitamin $D_3$ Analogues for the Treatment of Osteoporosis," *Osteoporosis Int. Suppl.*, vol. 1, 190-193 (1993); European Foundation for Osteoporosis.

Ntambi, J. M. et al., "Loss of stearoyl-CoA desaturase-1 function protects mice against adiposity," *Proc. Natl. Acad. Sci. USA*, 99(17), pp. 11482-11486 (2002).

Okano et al., "Regulatory Activities of 2β-(3-Hydroxypropoxy)-1α,25-Dihydroxy-Vitamin $D_3$, a Novel Synthetic Vitamin $D_3$ Derivative, on Calcium Metabolism," *Biochem. Biophys. Res. Commun.*, vol. 163(3), 1444-1449 (1989); published by Academic Press, Inc.

Ostrem et al., "24- and 26-homo-1,25-dihydroxyvitamin $D_3$: Preferential activity in inducing differentiation of human leukemia cells HL-60 in vitro," *Proc. Natl. Acad. Sci. USA*, vol. 84, pp. 2610-2614 (1987).

Ostrem et al., "Induction of Monocytic Differentiation of HL-60 Cells by 1,25-Dihydroxyvitamin D Analogs," *J. Biol. Chem.*, vol. 262(29), pp. 14164-14171 (1987); The American Society for Biochemistry and Molecular Biology, Inc.

Peleg, S., *Chapter 60: Molecular Basis for Differential Action of Vitamin D Analogs, In: Vitamin D*, Feldman, Glorieux and Pike (eds.), pp. 1011-1025 (1977); Academic Press.

Perlman et al., "1α,25-Dihydroxy-19-Nor-Vitamin $D_3$, A Novel Vitamin D-Related Compound with Potential Therapeutic Activity," *Tetrahedron Lett.*, vol. 31(13), pp. 1823-1824 (1990); Pergamon Press, Great Britain.

Perlman et al., "Novel Synthesis of 19-Nor-Vitamin D Compounds," *Tetrahedron Lett.*, vol. 32(52), pp. 7663-7666 (1991); Pergamon Press, Great Britain.

Peterson et al., Studies of the Ketone Obtained from the Ozonolysis of Vitamin D. Molecular Mechanics Calculations for It and Related Hydrindanones,: *J. Org. Chem.*, vol. 51, pp. 1948-1954 (1986); American Chemical Society.

Plum, L. A. et al., "Biologically active noncalcemic analogs of 1α,25-dihydroxyvitamin D with an abbreviated side chain containing no hydroxyl," *Proc. Natl. Acad. Sci. USA*, 101(18), pp. 6900-6904 (2004).

Posner et al., Stereocontrolled Total Synthesis of Calcitriol Derivatives: 1,25-Dihydroxy-2(4'-hydroxybutyl)vitamin $D_3$ Analogs of an Osteoporosis Drug, *J. Org. Chem.*, vol. 59, pp. 7855-7861 (1994); American Chemical Society.

Posner et al., "2-Fluoroalkyl A-Ring Analogs of 1,25-Dihydroxyvitamin $D_3$ Stereocontrolled Total Synthesis via Intramolecular and Intermolecular Diels—Alder Cycloadditions. Preliminary Biological Testing," *J. Org. Chem.*, vol. 60, 4617-4628 (1995); American Chemical Society.

Qiu, Z. et al., "DNA Synthesis and Mitotic Clonal Expansion Is Not a Required Step for 3T3-L1 Preacipocyte Differentiation into Adipocytes," *J. Biol. Chem.*, 276(15), pp. 11988-11995 (2001); The American Society for Biochemistry and Molecular Biology, Inc.

Sardina et al., "Studies on the Synthesis of Side-Chain Hydroxylated Metabolites of Vitamin D. 2. Stereocontrolled Synthesis of 25-Hydroxyvitamin $D_2$," *J. Org. Chem.*, vol. 51, 1264-1269 (1986); American Chemical Society.

Sato, M. et al., "Demonstration of 1α,25-Dihydroxyvitamin $D_3$ Receptor-Like Molecule in ST 13 and 3T3 L1 Preadipocytes and its Inhibitory Effects on Preadipocyte Differentiation," *J. Cell. Phys.*, 135, pp. 545-550 (1988); Alan R. Liss, Inc.

Schaub, K. et al., "The Formation of the 1,25 Dihydroxyvitamin $D_3$ Receptor Homo- and Heterodimers Depends Both on the Kind of Vitamin D Analogues and the Hormone Response Elements," *Proceedings of The Tenth Workshop on Vitamin D*, A. W. Norman, R. Bouillon, and M. Thomasset (eds.), pp. 220-221 (1997).

Sicinski, R. R. et al., "New $1\alpha$,25-Dihydroxy-19-norvitamin $D_3$ Compounds of High Biological Activity: Synthesis and Biological Evaluation of 2-Hydroxymethyl, 2-Methyl, and 2-Methylene Analogues," *J. Med. Chem.*, 41, 4662-4674 (1998); American Chemical Society.

Sicinski, R. R. et al., "Synthesis and Biological Activity of 2-Hydroxy and 2-Alkoxy Analogs of $1\alpha$,25-Dihydroxy-19-norvitamin $D_3$," *J. Med. Chem.*, 37, pp. 3730-3738 (1994); American Chemical Society.

Suda, T. et al., Biological Activity of 25-Hydroxyergocalciferol in Rats, *J. Nutrition*, vol. 100, pp. 1049-1052 (1970).

Toh et al., "Studies on a Convergent Route to Side-Chain Analogues of Vitamin D: 25-Hydroxy-23-oxavitamin $D_3$," *J. Org. Chem.*, 48, pp. 1414-1417 (1983); American Chemical Society.

Yeh, W. et al., "Cascade regulation of terminal adipocyte differentiation by three members of the C/EBP family of leucine zipper proteins," *Genes & Dev.*, 9, pp. 168-181 (1995); Cold Spring Harbor Laboratory Press.

\* cited by examiner

Competitive VDR Binding

$K_i$: $1,25(OH)_2D_3 = 2.2 \times 10^{-11}$ M
CN-67 $= 1.5 \times 10^{-9}$ M
OU-72 $= 2.3 \times 10^{-11}$ M

VITAMIN D RECEPTOR ANTAGONISTS AND THEIR USE IN TREATING ASTHMA

CROSS REFERENCES TO RELATED APPLICATIONS

This application claims priority to U.S. Provisional Application No. 60/545,347, filed on Feb. 17, 2004, the entire disclosure of which is hereby incorporated by reference and for all purposes in its entirety as if fully set forth herein.

FIELD OF THE INVENTION

This invention relates generally to vitamin D receptor antagonists and their use in treating conditions such as asthma. More specifically, the invention relates to various ester and ketone vitamin D analogs and their use as antagonists of the vitamin D receptor and in treating asthma.

BACKGROUND OF THE INVENTION

Asthma has long been a major medical problem throughout the world, especially in well-developed countries. To further compound the problem, both the incidence and severity of asthma appear to be on the increase. For example, during the period of 1980-1994, the reported incidence of asthma rose 75% in the United States. By 1998, 17 million Americans, 4.8 million of whom are children, were diagnosed with asthma. An estimated 5,000 asthma-related deaths occur each year in the United States. Centers for Disease Control and Prevention, Morbidity and Mortality Weekly Report 47, 1022-25; Focus on Asthma, National Institute of Allergy and Infections Disease.

Asthma is a disease in which bronchial constriction occurs resulting in impaired air flow followed by an infiltration of eosinophils and lymphocytes in the peribronchial tissues. Thus, an inflammatory process appears to be involved in the underlying reasons for allergic-based asthmatic reaction.

To date, no true in vivo antagonist of the vitamin D hormone has been disclosed. However, the following two compounds have been reported to act as vitamin D antagonists in vitro in the Schering laboratories. Herdick M., Steinmeyer A., and Carlberg, C. *J. Biol. Chem.*, 275, 16506-16512 (2000); Herdick, M., Steinmeyer, A., and Carlberg, C. Proceedings of the 11th International Vitamin D Workshop, (Norman, A. W., Bouillon, R., Thomasset, M. eds.), pp. 259-262. Schaub, K., Steinmeyer, A., and Bunte, T. Proceedings of the Tenth Workshop on Vitamin D (A. W. Norman, R. Bouillon, and M. Thomasset, eds.), pp. 220-221 (1997).

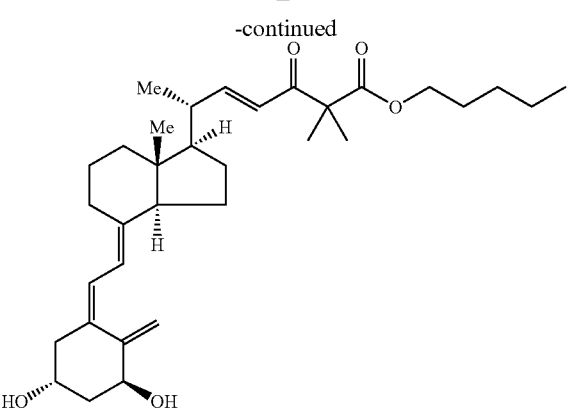

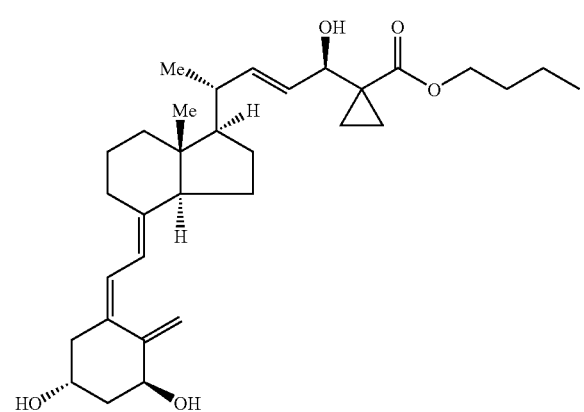

Related compounds having a 2α-methyl group have also been disclosed. Fujishima, T., Kojima, Y., Azumaya, I., Kittaka, A., and Takayama, H. *Bioorg. Med. Chem.* 11, 3621-3631 (2003). The structures of the 2α-methyl compounds disclosed by Fujishima et al. are provided below

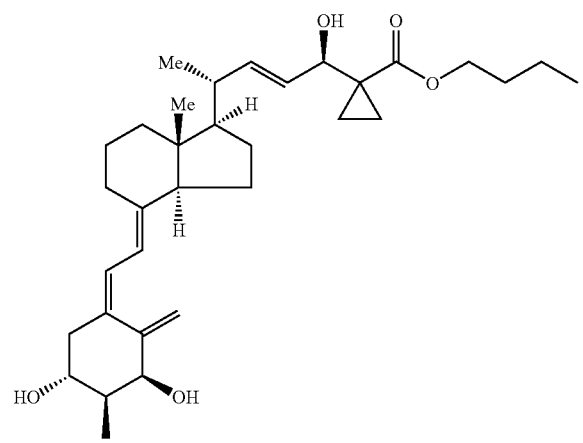

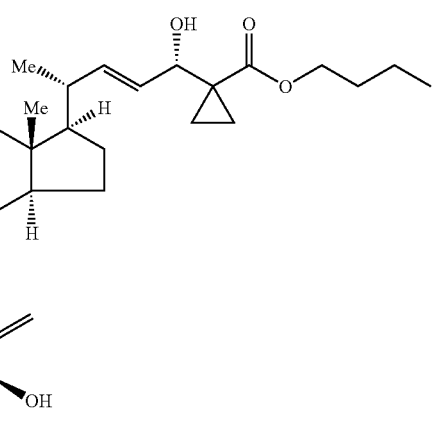

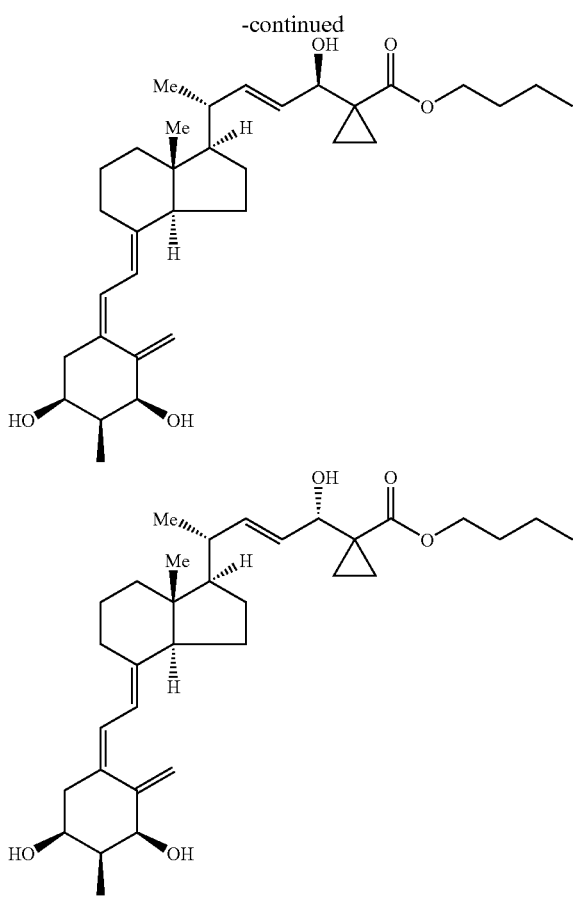
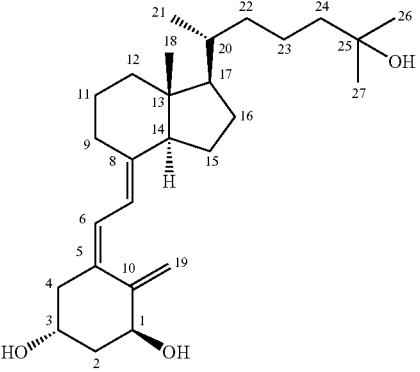
Because the six compounds depicted above are esters, delivery by circulation to target tissue may be limited unless they first undergo hydrolysis. However

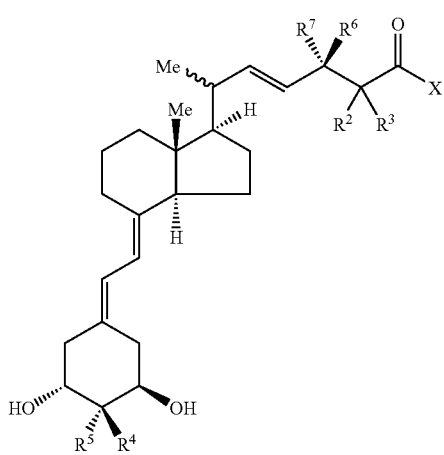

where

X is an $R^1$ group or is a group of formula $-OR^1$ wherein $R^1$ is a straight or branched chain alkyl group having 1 to 8 carbon atoms;

$R^2$ and $R^3$ are independently selected from H or straight or branched chain alkyl groups having 1 to 4 carbon atoms; or $R^2$ and $R^3$ join together to form a ring having 3 to 6 ring members;

$R^4$ is a straight or branched chain alkyl group having 1 to 6 carbon atoms;

$R^5$ is H; or $R^4$ and $R^5$ together represent a $=CH_2$ group; and $R^6$ is OH and $R^7$ is H; or $R^6$ and $R^7$ together represent a $=O$ group. In some embodiments, $R^6$ is OH and $R^7$ is H; $R^6$ is an O-alkyl group and $R^7$ is H, wherein the alkyl group of the O-alkyl group is a straight or branched chain alkyl group having from 1 to 8 carbon atoms; or $R^6$ and $R^7$ together represent a $=O$ group.

In another aspect, the invention provides compounds of formula XIV, tautomers of the compounds, pharmaceutically acceptable salts of the compounds, and pharmaceutically acceptable salts of the tautomers

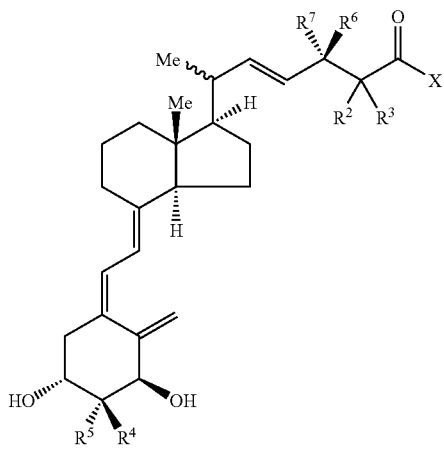

where

X is an $R^1$ group, wherein $R^1$ is a straight or branched chain alkyl group having 1 to 8 carbon atoms;

$R^2$ and $R^3$ are independently selected from H or straight or branched chain alkyl groups having 1 to 4 carbon atoms; or $R^2$ and $R^3$ join together to form a ring having 3 to 6 ring members;

$R^4$ is a straight or branched chain alkyl group having 1 to 6 carbon atoms;

$R^5$ is H;

$R^6$ is OH and $R^7$ is H; or $R^6$ and $R^7$ together represent a $=O$ group. In some embodiments, $R^6$ is OH and $R^7$ is H; $R^6$ is an O-alkyl group and $R^7$ is H, wherein the alkyl group of the O-alkyl group is a straight or branched chain alkyl group having from 1 to 8 carbon atoms; or $R^6$ and $R^7$ together represent a $=O$ group.

In another aspect, the invention provides compounds of formula XIX and XX

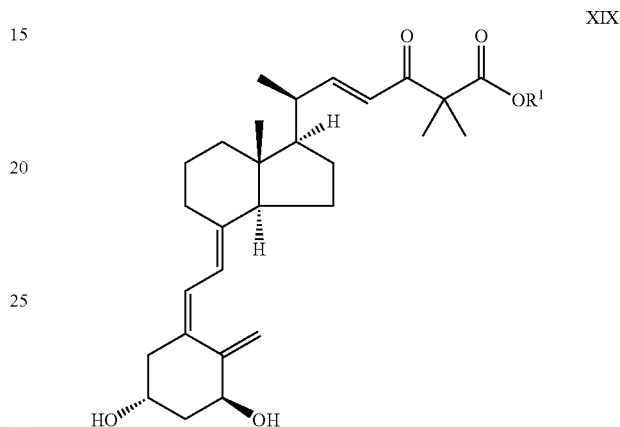

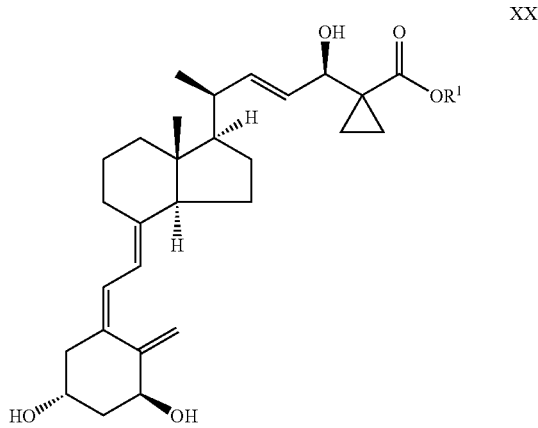

where $R^1$ is a straight or branched chain alkyl group having from 1 to 8 carbon atoms.

The invention further provides pharmaceutical formulations that include one or more compound of the invention and a pharmaceutically acceptable carrier.

In another aspect, the invention provides a method of antagonizing the vitamin D receptor. The method includes administering a compound or pharmaceutical composition of the invention to an animal subject. The compound administered to the subject antagonizes the vitamin D receptor.

In another aspect, the invention provides a method of treating asthma or eczema in an animal subject suffering from asthma or eczema. The method includes administering an effective amount of a compound or pharmaceutical composition of the invention to the animal subject. Administration of the compound leads to a reduction in the symptoms associated with asthma or eczema.

In some embodiments of the methods of the invention, the compound or pharmaceutical composition is administered orally, parenterally, transdermally, or topically. In other embodiments, the compound or pharmaceutical formulations is administered in an aerosol which may be accomplished using an inhaler or a nebulizer.

In another aspect, the invention provides the use of a compound of the invention in the preparation of a pharmaceutical composition or medicament for antagonizing the vitamin D receptor and/or for treating asthma or eczema in an animal subject suffering from asthma or eczema. In some embodiments, the compounds are used to prepare an aerosol which may include a glycol compound such as propylene glycol.

In yet another aspect, the invention provides a method of antagonizing the vitamin D receptor. The method includes administering an effective amount of a compound of formula XXI or XXII to an animal subject. The compound administered to the subject antagonizes the vitamin D receptor. The compounds of formula XXI and XXII have the following structures

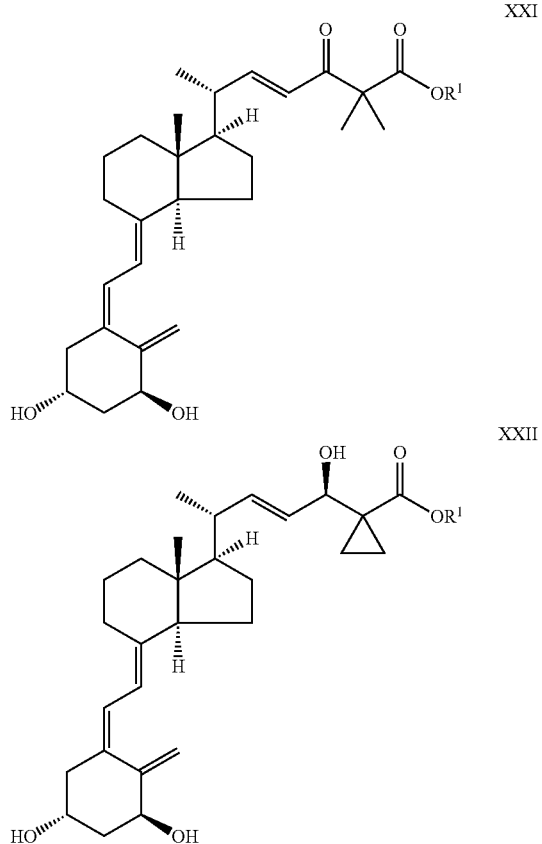

where $R^1$ is a straight or branched chain alkyl group having from 1 to 8 carbon atoms. In some such embodiments, the animal subject suffers from asthma or eczema, and administration of the compound or a pharmaceutical formulation that includes the compound results in a reduction of symptoms associated with asthma or eczema in the subject.

In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the animal subject is a primate such as, in some embodiments, a human.

Further objects, features and advantages of the invention will be apparent from the following detailed description.

BRIEF DESCRIPTION OF THE DRAWINGS

FIG. 1 is a graph comparing the relative activity of CN-67, OU-72, and 1,25(OH)$_2$D$_3$ to compete for binding with [$^3$H]-1,25-(OH)$_2$-D$_3$ to the full-length recombinant rat vitamin D receptor.

FIG. 2 is a graph comparing the percent HL-60 cell differentiation as a function of the concentration of CN-67 with that of 1,25(OH)$_2$D$_3$.

FIG. 3 is a graph comparing the percent HL-60 cell differentiation as a function of the concentration of OU-72 with that of 1,25(OH)$_2$D$_3$.

FIG. 4 is a graph comparing the in vitro transcription activity of CN-67 and OU-72 with that of 1,25(OH)$_2$D$_3$.

FIG. 5 is a graph comparing the in vitro transcription activity of of 1,25(OH)$_2$D$_3$ with that of 1,25(OH)$_2$D$_3$ plus CN-67.

FIG. 6 is a graph comparing the in vitro transcription activity of of 1,25(OH)$_2$D$_3$ with that of 1,25(OH)$_2$D$_3$ plus OU-72.

FIG. 7 is a bar graph comparing the bone calcium mobilization activity of OU-72 with that of (20S)-2-methylene-19-nor-1α,25-dihydroxyvitamin $D_3$ (2-MD) and 1,25(OH)$_2$D$_3$.

FIG. 8 is a bar graph comparing the intestinal calcium transport activity of OU-72 with that of 2-MD and 1,25(OH)$_2$D$_3$.

DETAILED DESCRIPTION OF THE INVENTION

Figure 1:
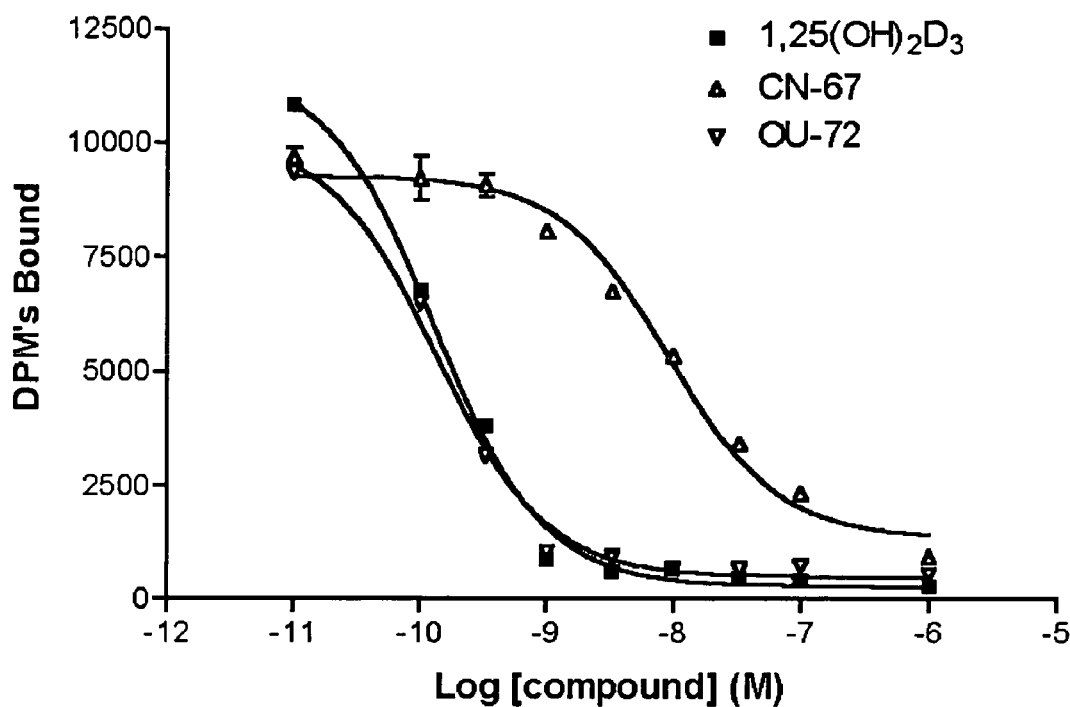
FIGS. 1-8 illustrate various biological activities of (22E)-(24R)-24-butoxy-25-carbobutoxy-2-methylene-26,27-cyclo-22-dehydro-1α-hydroxy-19-norvitamin $D_3$ (referred to as "CN-67" in the Figures) and (22E)-(24R)-25-carbobutoxy-2-methylene-26,27-cyclo-22-dehydro-1α,24-dihydroxy-19-norvitamin $D_3$ (referred to as "OU-72" in the Figures) compared with those of the native hormone 1α,25-dihydroxyvitamin $D_3$ (referred to as "1,25(OH)$_2$D$_3$" in the Figures).

The invention provides various vitamin D analogs that act as antagonists of the vitamin D receptor. The invention also provides methods for antagonizing the vitamin D receptor, methods for treating conditions such as asthma and eczema, and the use of various vitamin D analogs in preparing medicaments for use in antagonizing the vitamin D receptor and/or treating conditions such as asthma and eczema.

Various 19-nor 2-alkylidene and 2α-alkyl analogs of vitamin D are synthesized, tested and found to antagonize the vitamin D receptor. Such compounds include compounds of formula I, tautomers of the compounds, pharmaceutically acceptable salts of the compounds, and pharmaceutically acceptable salts of the tautomers

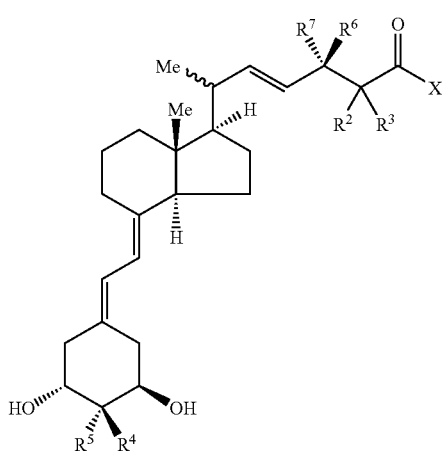

where

X is an $R^1$ group or is a group of formula —$OR^1$, wherein $R^1$ is a straight or branched chain alkyl group having 1 to 8 carbon atoms;

$R^2$ and $R^3$ are independently selected from H or straight or branched chain alkyl groups having 1 to 4 carbon atoms; or $R^2$ and $R^3$ join together to form a ring having 3 to 6 ring members;

$R^4$ is a straight or branched chain alkyl group having 1 to 6 carbon atoms;

$R^5$ is H; or $R^4$ and $R^5$ together represent a =$CH_2$ group; and $R^6$ is OH and $R^7$ is H; or $R^6$ and $R^7$ together represent a =O group. In some embodiments, $R^6$ is OH and $R^7$ is H; $R^6$ is an O-alkyl group and $R^7$ is H, wherein the alkyl group of the O-alkyl group is a straight or branched chain alkyl group having from 1 to 8 carbon atoms; or $R^6$ and $R^7$ together represent a =O group.

In some embodiments of the compounds of formula I, $R^4$ is a methyl group and $R^5$ is a H such that the compounds of formula I are 19-nor 2α-methyl analogs of vitamin D. In other embodiments of the compounds of formula I, $R^4$ and $R^5$ together represent a =$CH_2$ group such that the compounds of formula I are 2-methylene 19-nor vitamin D analogs. In other embodiments of the compounds of formula I, $R^2$ and $R^3$ are either both methyl groups, or $R^2$ and $R^3$ join together to form a cyclopropyl ring that includes the carbon to which they are both attached. In other embodiments of the compounds of formula I, X is an $R^1$ group such that the compounds are ketones. In some such embodiments $R^1$ is a straight chain alkyl group such as a methyl, ethyl, propyl, butyl, pentyl, hexyl, or heptyl group. In other such embodiments, $R^1$ is an ethyl, propyl, butyl, pentyl, or hexyl group, and in still other such embodiments, $R^1$ is a propyl, butyl, pentyl, or hexyl group. In other embodiments of the compounds of formula I, X is an —$OR^1$ group such that the compounds are esters. In yet other embodiments of the compounds of formula I, $R^6$ is OH and $R^7$ is H such that the compound includes an allylic alcohol group whereas in still further embodiments, $R^6$ and $R^7$ together represent a =O group such that the compounds include an enone functional group.

In some embodiments of the compounds of formula I, the compounds have the formula IA whereas in other embodiments, the compounds have the formula IB

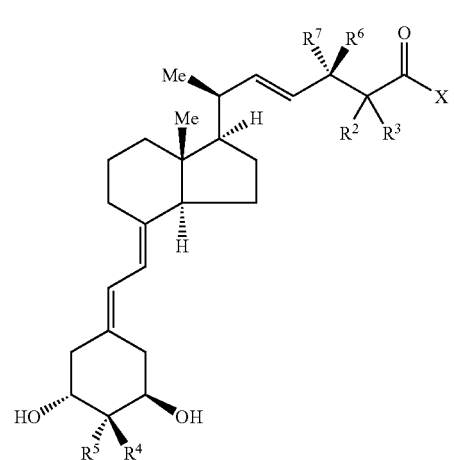

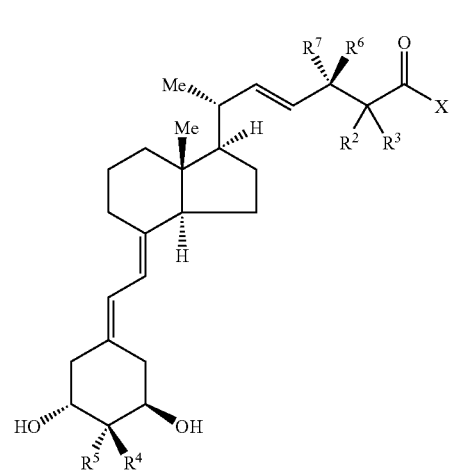

where the variables X, $R^1$, $R^2$, $R^3$, $R^4$, $R^5$, $R^6$, and $R^7$ have any of the values of any of the embodiments of the compounds of formula I.

Examples of suitable compounds of formula I, include various 2α-methyl 19-nor vitamin D analog ester compounds. Examples of such esters include, but are not limited to, compounds of formula II ((22E)-(20S,24R)-25-carbobutoxy-2α-methyl-26,27-cyclo-22-dehydro-1α,24-dihydroxy-19-norvitamin $D_3$), formula III ((22E)-(24R)-25-carbobutoxy-2α-methyl-26,27-cyclo-22-dehydro-1α,24-dihydroxy-19-norvitamin $D_3$), formula IV ((22E)-(20S)-25-carbopentoxy-2α-methyl-24-oxo-22-dehydro-1α-hydroxy-19-norvitamin $D_3$), formula V ((22E)-25-carbopentoxy-2α-methyl-24-oxo-22-dehydro-1α-hydroxy-19-norvitamin $D_3$), and the like.

II

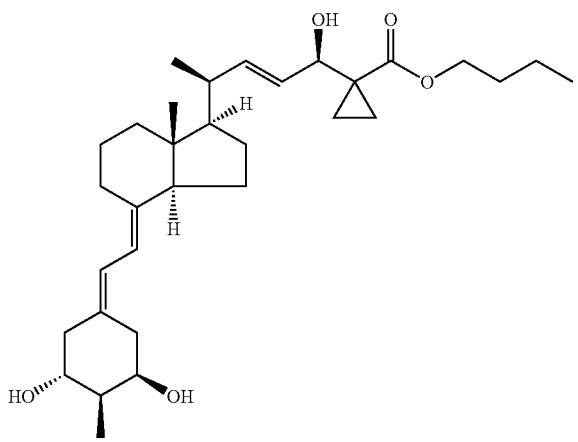

III

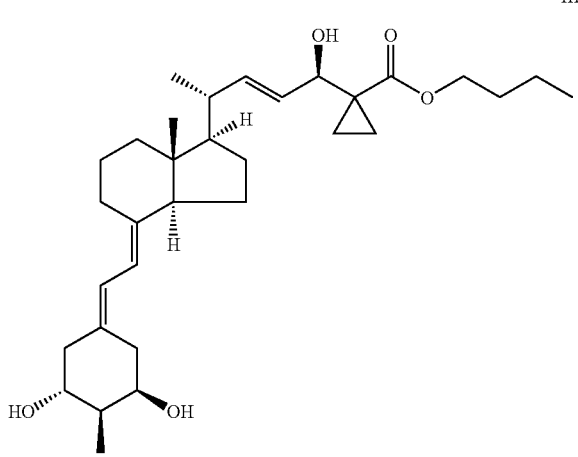

IV

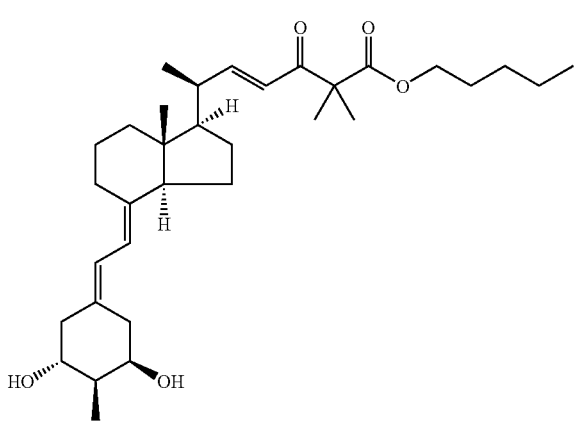

V

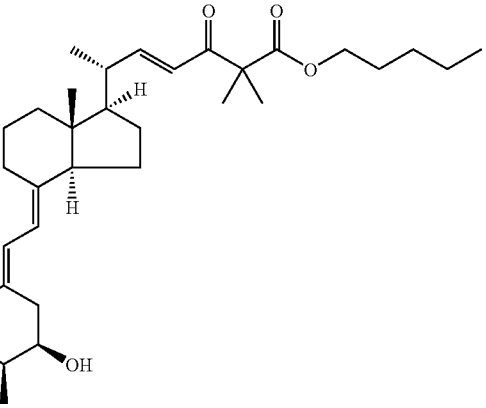

Other examples of suitable compounds of formula I include 2-methylene 19-nor vitamin D analog ester compounds. Examples of such esters include, but are not limited to, compounds of formula VI ((22E)-(20S)-25-carbopentoxy-2-methylene-24-oxo-22-dehydro-1α-hydroxy-19-norvitamin $D_3$), formula VII ((22E)-25-carbopentoxy-2-methylene-24-oxo-22-dehydro-1α-hydroxy-19-norvitamin $D_3$), formula VIII ((22E)-(20S,24R)-25-carbobutoxy-2-methylene-26,27-cyclo-22-dehydro-1α,24-dihydroxy-19-norvitamin $D_3$), formula IX ((22E)-(24R)-25-carbobutoxy-2-methylene-26,27-cyclo-22-dehydro-1α,24-dihydroxy-19-norvitamin $D_3$), and the like.

VI

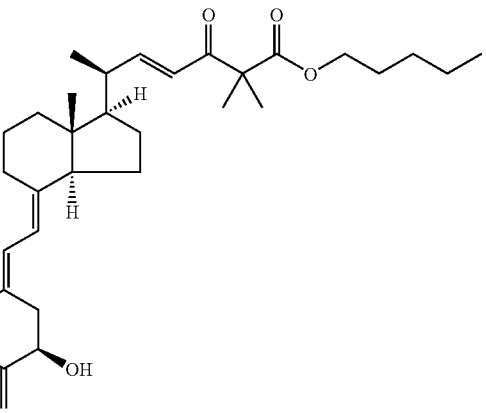

VII

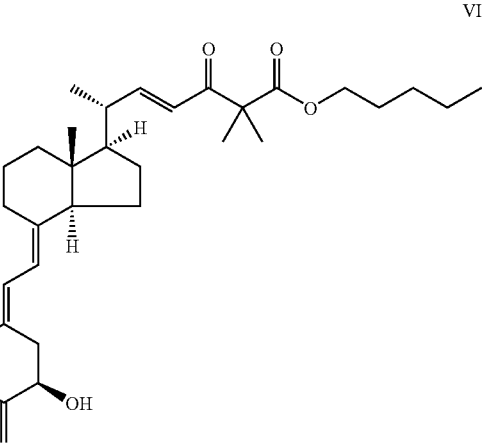

-continued

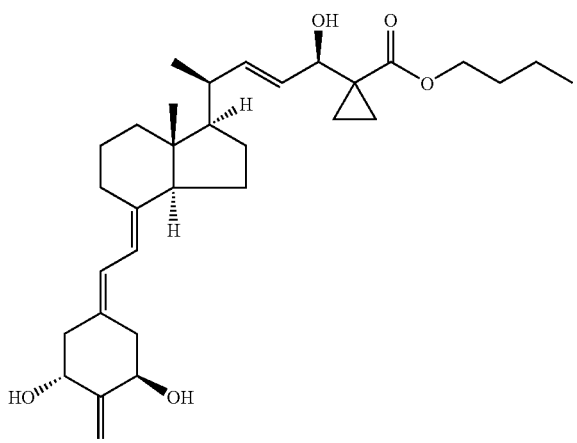

VIII

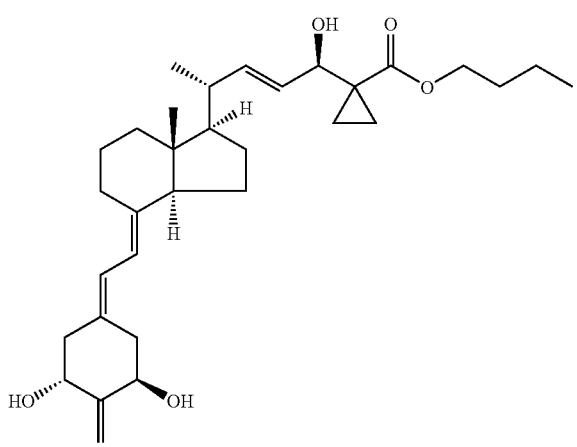

IX

Still other examples of suitable compounds of formula I include various 2α-methyl or 2-methylene 19-nor vitamin D analog ketone compounds. Examples of such ketones include, but are not limited to, compounds of formula X ((22E)-(20S)-25-heptanoyl-2α-methyl-24-oxo-22-dehydro-1α-hydroxy-19-norvitamin $D_3$), formula XI ((22E)-25-heptanoyl-2α-methyl-24-oxo-22-dehydro-1α-hydroxy-19-norvitamin $D_3$), formula XII ((22E)-(20S)-25-heptanoyl-2-methylene-24-oxo-22-dehydro-1α-hydroxy-19-norvitamin $D_3$), formula XIII ((22E)-25-heptanoyl-2-methylene-24-oxo-22-dehydro-1α-hydroxy-19-norvitamin $D_3$), and the like.

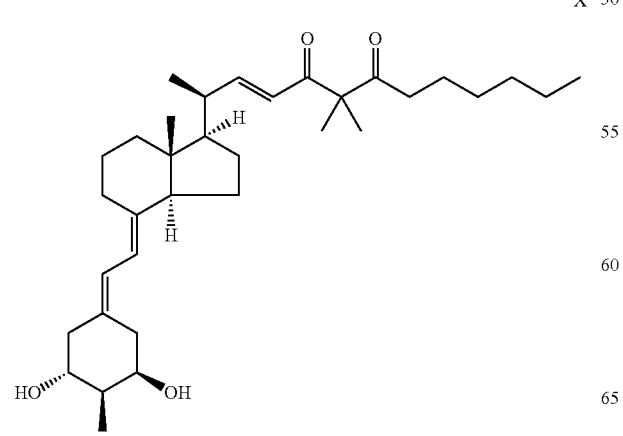

X

-continued

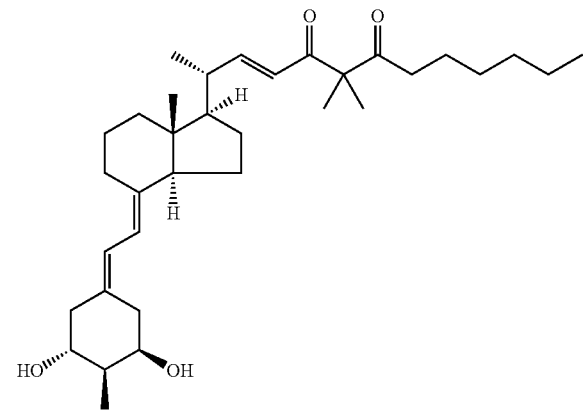

XI

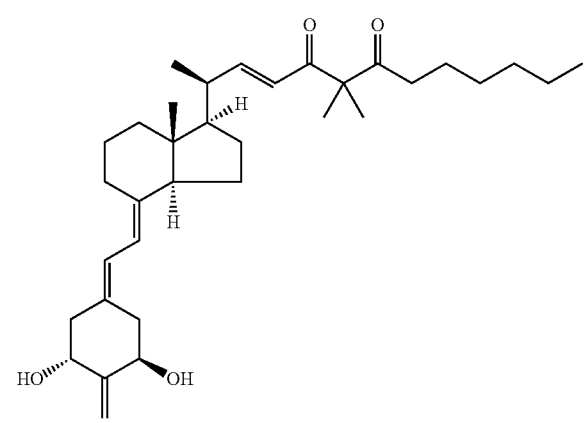

XII

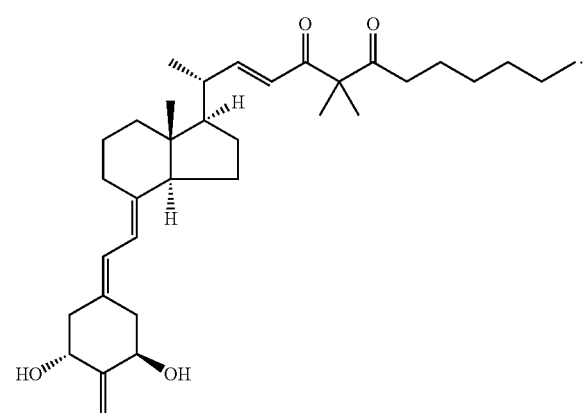

XIII

Other vitamin D analogs are also synthesized, tested, and found to antagonize the vitamin D receptor. Such compounds include 2α-alkyl vitamin D ketone analogs such as compounds of formula XIV, tautomers of the compounds, pharmaceutically acceptable salts of the compounds, and pharmaceutically acceptable salts of the tautomers

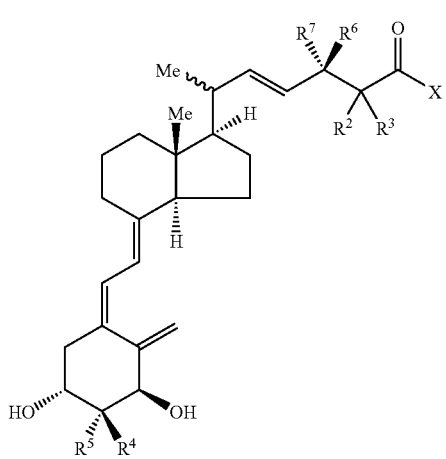

XIV where

X is an $R^1$ group, wherein $R^1$ is a straight or branched chain alkyl group having 1 to 8 carbon atoms;

$R^2$ and $R^3$ are independently selected from H or straight or branched chain alkyl groups having 1 to 4 carbon atoms; or $R^2$ and $R^3$ join together to form a ring having 3 to 6 ring members;

$R^4$ is a straight or branched chain alkyl group having 1 to 6 carbon atoms;

$R^5$ is H;

$R^6$ is OH and $R^7$ is H; or $R^6$ and $R^7$ together represent a =O group. In some embodiments, $R^6$ is OH and $R^7$ is H; $R^6$ is an O-alkyl group and $R^7$ is H, wherein the alkyl group of the O-alkyl group is a straight or branched chain alkyl group having from 1 to 8 carbon atoms; or $R^6$ and $R^7$ together represent a =O group.

In some embodiments of the compounds of formula XIV, $R^4$ is a methyl group such that the compounds are 2α-methyl vitamin D analogs. In some embodiments of the compounds of formula XIV, $R^2$ and $R^3$ are either both methyl groups, or $R^2$ and $R^3$ join together to form a cyclopropyl ring that includes the carbon to which they are both attached. In yet other embodiments of the compounds of formula XIV, $R^1$ is a straight chain alkyl group such as a methyl, ethyl, propyl, butyl, pentyl, hexyl, or heptyl group. In other such embodiments, $R^1$ is an ethyl, propyl, butyl, pentyl, hexyl, or heptyl group, and in other such embodiments, $R^1$ is a propyl, butyl, pentyl, or hexyl group. In still other embodiments of the compounds of formula XIV, $R^6$ is OH and $R^7$ is H whereas in other embodiments $R^6$ and $R^7$ together represent a =O group.

In some embodiments of the compounds of formula XIV, the compounds have the formula XIVA whereas in other embodiments, the compounds have the formula XIVB

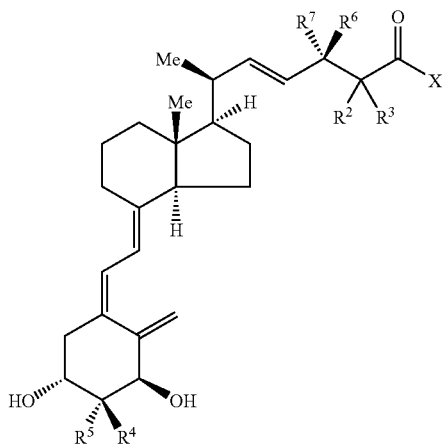

XIVA

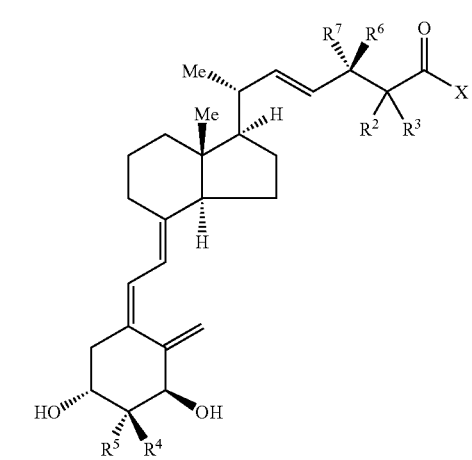

XIVB where the variables X, $R^1$, $R^2$, $R^3$, $R^4$, $R^5$, $R^6$, and $R^7$ have any of the values of any of the embodiments of the compounds of formula XIV.

Examples of suitable compounds of formula XIV include various 2α-methyl vitamin D ketone analogs. Examples of such compounds include, but are not limited to, compounds of formula XV ((22E)-(20S)-25-heptanoyl-2α-methyl-24-oxo-22-dehydro-1α-hydroxyvitamin $D_3$), formula XVI ((22E)-25-heptanoyl-2α-methyl-24-oxo-22-dehydro-1α-hydroxyvitamin $D_3$), formula XVII ((22E)-(20S,24R)-25-hexanoyl-2α-methyl-26,27-cyclo-22-dehydro-1α,24-dihydroxyvitamin $D_3$), formula XVIII ((22E)-(24R)-25-hexanoyl-2α-methyl-26,27-cyclo-22-dehydro-1α,24-dihydroxyvitamin $D_3$), and the like.

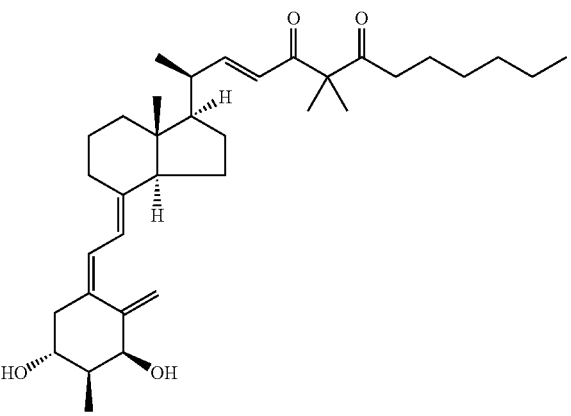

XV

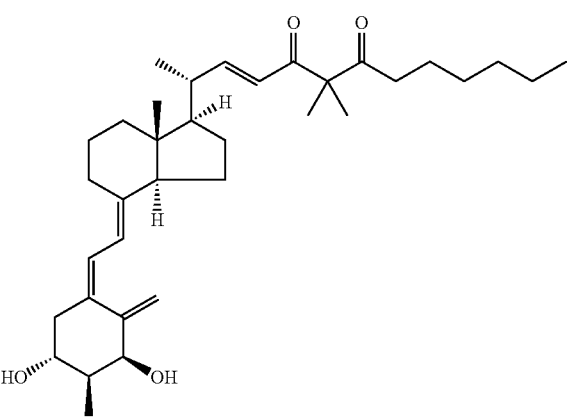

XVI

-continued

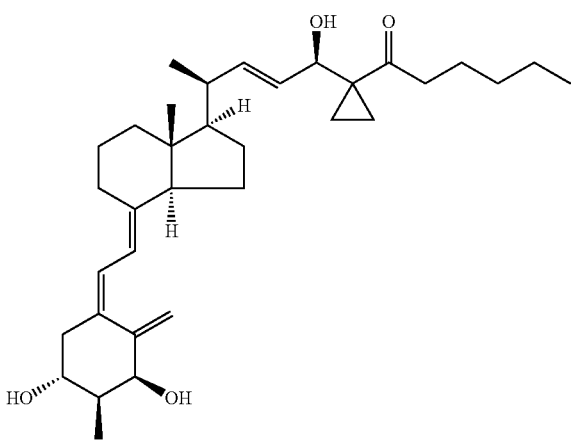

XVII

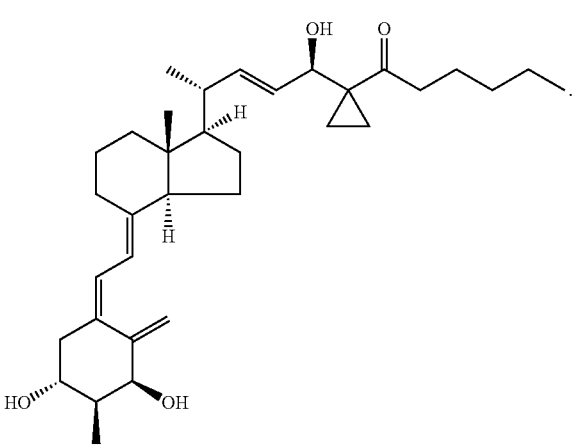

XVIII

Various vitamin D ester compounds are also tested and found to exhibit antagonistic activity with respect to the vitamin D receptor. Such compounds include compounds of formula XIX and XX

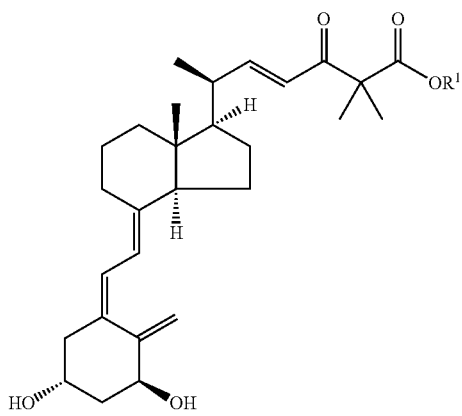

XIX

-continued

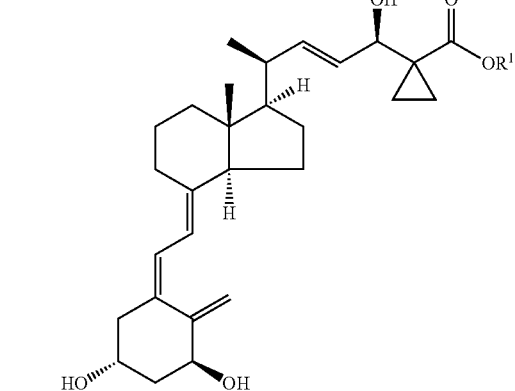

XX where $R^1$ is a straight or branched chain alkyl group having from 1 to 8 carbon atoms. In some embodiments of the compounds of formula XIX and XX, $R^1$ is a straight chain alkyl group selected from a methyl, ethyl, propyl, butyl, pentyl, hexyl, or heptyl group. In other such embodiments, $R^1$ is selected from an ethyl, propyl, butyl, pentyl, or hexyl group, and in still other embodiments is selected from a propyl, butyl, pentyl, or hexyl group.

Pharmaceutical formulations and medicaments may be prepared using any of the compounds of the invention. Such compositions typically include one or more compound of the invention and a pharmaceutically acceptable carrier.

Because the compounds of the invention antagonize the vitamin D receptor both in vitro and in vivo, the invention further provides methods for antagonizing the vitamin D receptor. Such methods typically include administering a compound or pharmaceutical composition that includes one or more compound of the invention to an animal subject. The compound or compounds administered to the subject antagonize the vitamin D receptor. The compounds and formulations of the invention may also be used to treat asthma or eczema in animal subjects. Such methods typically include administering an effective amount of a compound or pharmaceutical composition of the invention to the animal subject. Administration of the compound leads to a reduction in the symptoms associated with asthma or eczema. The compounds and pharmaceutical compositions of the invention may be administered by various methods such as orally, parenterally, transdermally, topically, or the like. Ketones such as compounds of formula I, IA, and IB in which X is an $R^1$ group, and compounds of formula X, XI, XII, XIII, XIV, XIVA, XIVB, XV, XVI, XVII, and XVIII are best suited for systemic administration, but may also be administered as an aerosol. Thus, each of the compounds of the invention is suitably administered as an aerosol using an inhaler or a nebulizer. Aerosols are particularly suitable for use in treating asthma with the compounds of the invention whereas topical administration may be more suitable for treatment of eczema and other skin conditions. Administration of ester compounds such as compounds of formula I, IA, and IB in which X is an —$OR^1$ group, compounds of formula II, III, IV, V, VI, VII, VII, and IX, and compounds of formula XIX and XX to subjects is best accomplished to asthmatic subjects when these compounds are administered as an aerosol because aerosol administration will deliver these compounds directly to a target tissue such as the lungs of an asthma patient. Aerosol formulations and medicaments may include a glycol compound such as ethylene glycol, propylene glycol, or the like.

The compounds and formulations of the invention may be administered to a wide variety of animal subjects. Examples of such subjects include mammals such as, but not limited to, rodents such as mice and rats, primates such as monkeys and humans, bovines such as cows, equines such as horses, canines such as dogs, felines such as cats, ursines such as bears, porcines such as pigs, rabbits, guinea pigs, and the like. In some embodiments, the compounds of the invention are administered to humans, and in other embodiments, the compounds are administered to rats or mice.

In some embodiments, a method of antagonizing the vitamin D receptor includes administering an effective amount of a compound of formula XXI or XXII to an animal subject. The compound administered to the subject antagonizes the vitamin D receptor. The compounds of formula XXI and XXII have the following structures

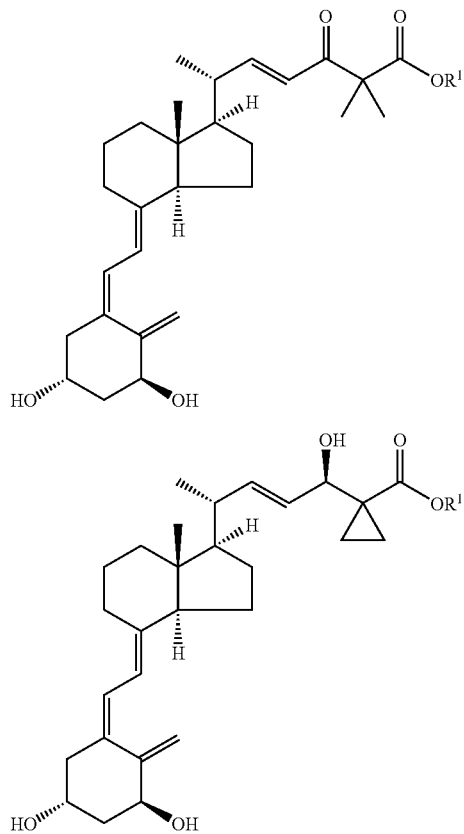

where $R^1$ is a straight or branched chain alkyl group having from 1 to 8 carbon atoms. In some embodiments, $R^1$ is selected from straight chain alkyl groups such as methyl, ethyl, propyl, butyl, pentyl, hexyl, heptyl, or octyl groups. In some such embodiments, the animal subject suffers from asthma or eczema and administration of the compound or a pharmaceutical formulation that includes the compound results in a reduction of symptoms associated with asthma or eczema in the subject. Compounds of formula XXI and XXII may be administered to subjects using the methods described above. However, such compounds are best administered for asthma treatment as an aerosol using an inhaler or nebulizer.

As used herein, the phrase "CN-67" refers to (22E)-(24R)-24-butoxy-25-carbobutoxy-2-methylene-26,27-cyclo-22-dehydro-1α-hydroxy-19-norvitamin $D_3$, a compound having the following formula:

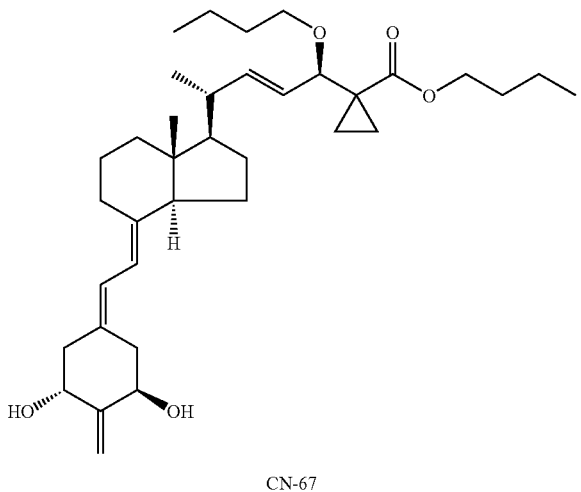

CN-67

As used herein, the phrase "OU-72" refers to (22E)-(24R)-25-carbobutoxy-2-methylene-26,27-cyclo-22-dehydro-1α,24-dihydroxy-19-norvitamin $D_3$, a compound having the following formula:

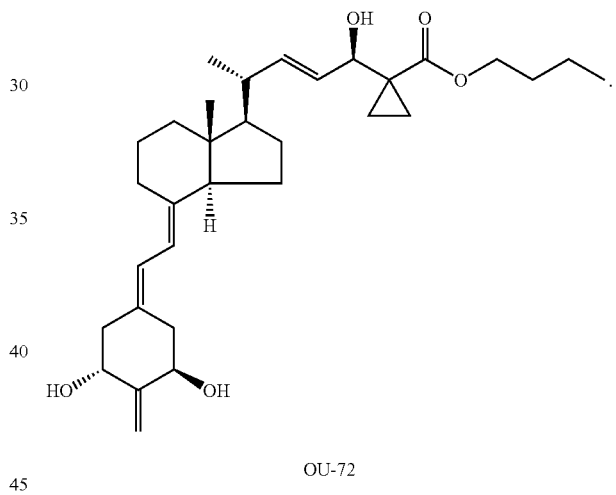

OU-72

As used herein, the phrases "straight and branched chain alkyl groups" and "straight or branched chain alkyl groups" refer to groups that include carbon and hydrogen atoms that only include carbon-carbon single bonds and carbon-hydrogen single bonds. These groups do not include any heteroatoms (atoms other than H or C). Thus, the phrases "straight and branched chain alkyl groups" and "straight or branched chain alkyl groups" include straight chain alkyl groups such as methyl, ethyl, propyl, butyl, pentyl, hexyl, heptyl, and octyl groups and branched chain isomers of straight chain alkyl groups, including but not limited to, the following which are provided by way of example only: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH(CH$_3$)CH$_2$CH(CH$_3$)$_2$, —CH(CH$_3$)CH(CH$_3$)CH(CH$_3$)$_2$, —CH$_2$CH$_2$CH$_2$C(CH$_3$)$_3$, —CH$_2$CH$_2$CH$_2$CH(CH$_3$)$_2$, —CH$_2$CH$_2$CH(CH$_3$)C(CH$_3$)$_3$, —CH$_2$CH$_2$CH(CH$_3$)CH(CH$_3$)$_2$, and the like.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

The compounds of the invention may be used to prepare pharmaceutical formulations and medicaments for antagonizing the vitamin D receptor and/or for use in treating asthma or eczema in an animal subject suffering from such maladies. For treatment purposes, the compounds of the invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. In some embodiments, the compounds are formulation as an aerosol and may be administered using an inhaler or nebulizer. Any formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference it its entirety and for all purposes as if fully set forth herein.

The compounds may be administered orally, topically, parenterally, transdermally, by aerosol, or by various other methods which will be apparent to those skilled in the art. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 µg to 1000 µg per day of the compounds are appropriate for treatment purposes, such doses being adjusted according to the degree of ailment to be treated, its severity, and the response of the subject as is well understood in the art. Since the compounds exhibit specificity of action, each may be suitably administered alone, or together with graded doses of another vitamin D receptor antagonist.

Compositions for use in antagonizing the vitamin D receptor and for use in treating asthma or eczema comprise an effective amount of a vitamin D analog of the invention as the active ingredient, and a suitable carrier. An effective amount of such compounds for use in accordance with some embodiments of the invention ranges from about 0.01 µg to about 1000 µg per gm of composition, and may be administered topically, transdermally, orally, parenterally, or as an aerosol in dosages of from about 0.1 µg/day to about 1000 µg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

In some embodiments, the compound is advantageously administered in amounts sufficient to lessen the symptoms associated with asthma or eczema. Dosages, as described above, are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

Formulations suitable for aerosol administration may include a glycol such as polyethylene glycol, polypropylene glycol, or the like. Such aerosol formulations may be administered using an inhaler or a nebulizer.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

Synthesis of Compounds

The synthesis and characteristics of various vitamin D analogs is described in numerous United States patents and United States patent applications including U.S. Pat. No. 5,843,928, U.S. Pat. No. 5,945,410, U.S. Pat. No. 6,627,622, U.S. Pat. No. 6,579,861, U.S. Pat. No. 5,086,191, U.S. Pat. No. 5,585,369, U.S. Pat. No. 6,537,981, U.S. patent application Ser. No. 09/871,227 filed on May 31, 2001 and published as U.S. 2003/0013691A1 on Jan. 16, 2003, and U.S. patent application Ser. No. 10/613,201 filed on Jul. 3, 2003. Each of the references in this paragraph is hereby incorporated by reference in its entirety and for all purposes as if fully set forth herein.

Preparation of vitamin D compounds such as those having the basic structure I, XIV, XIX, and XX may generally be accomplished utilizing the same convergent synthesis methodology, i.e., the condensation of an appropriate bicyclic Windaus-Grundmann type ketone (A or B) with an allylic phosphine oxide such as C followed by deprotection (removal of the $Y_1$ and $Y_2$ groups).

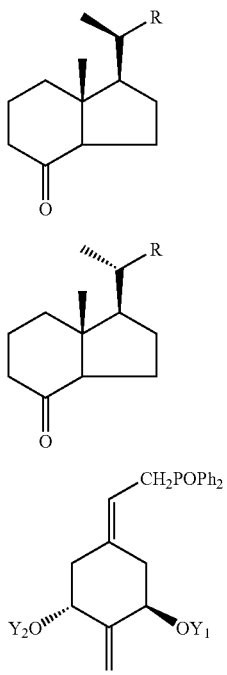

In the structures A, B, and C, R represents groups as defined above, and $Y_1$ and $Y_2$ are preferably hydroxy-protecting groups such as silyl protecting groups, it being also understood that any functionalities in R that might be sensitive, or that interfere with the condensation reaction, be suitably protected as is well-known in the art. For example, a hydroxyl functionality in an R group is suitably protected with a trialkylsilyl group such as a triethylsilyl group or as a THP (tetrahydropyranyl) group during the reaction of the compound of formula A or B with the compound of formula C. Similarly, a ketone group in an R group may be protected as a cyclic ketal by reaction with 1,3-dihydroxypropane or 1,2-dihydroxyethane using standard protection procedures. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Hydraindanones of the general structure A and B are known, or can be readily prepared using known or adapted methods as will be readily apparent to one of skill in the art. Specific important examples of bicyclic ketones are Grundmann's ketone analogs (a and b) (see Mincione et al., *Synth. Commun* 19, 723, 1989; Peterson et al., *J. Org. Chem.* 51, 1948, (1986)).

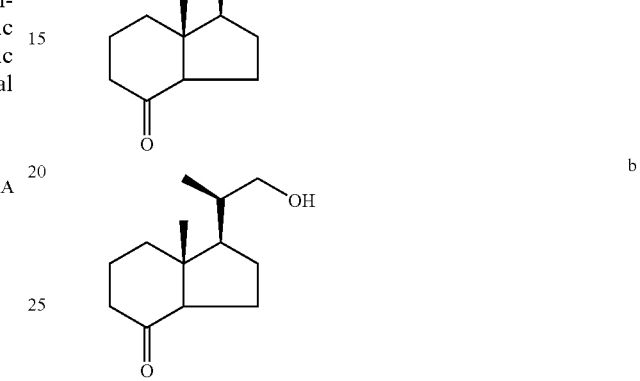

As shown in Scheme I, epimerization of aldehyde precursors (compounds D and E of Scheme I) of Grundmann type ketones can be readily accomplished with various reagents including tetrabutylammonium hydroxide to provide the 20R and 20S Grundmann ketones which may be coupled with phosphine oxides such as compound C to prepare 20R and 20S compounds of the invention. Separation of the epimers may be accomplished using standard procedures such as chromatography.

Scheme I

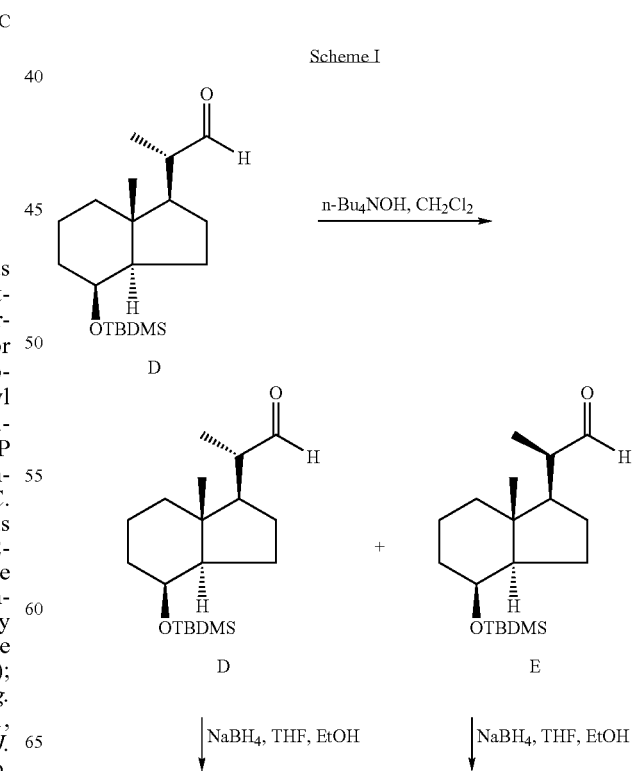

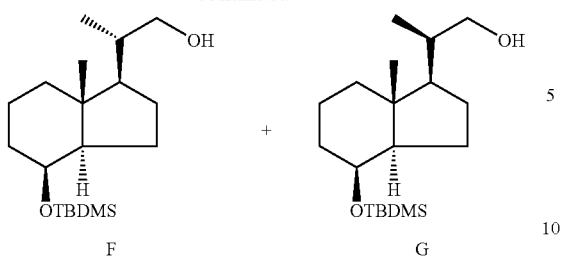

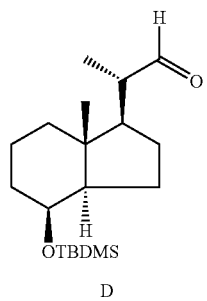

As shown in Scheme II, compounds such as D of Scheme I and Scheme II are readily obtainable from vitamin $D_2$. For example, ozonolysis of vitamin $D_2$ followed by reduction with a reducing agent such as sodium borohydride provides dihydroxy compound H. Selective protection of the two hydroxyl groups followed by deprotection of the side chain hydroxyl group and then oxidation provides aldehyde D which may be epimerized as depicted in Scheme I.

Scheme II

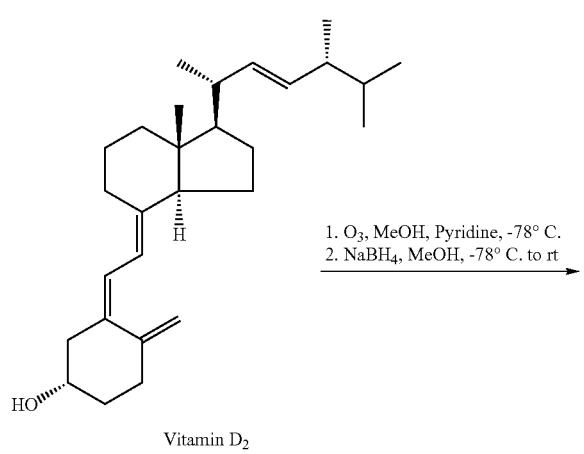

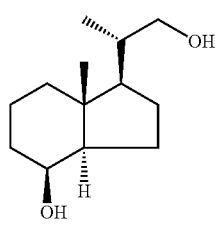

A synthetic route has been disclosed for the preparation of the required phosphine oxides of general structure C starting from a methyl quinicate derivative which is easily obtained from commercial (1R,3R,4S,5R)-(−)-quinic acid as described by Perlman et al., *Tetrahedron Lett.* 32, 7663 (1991) and DeLuca et al., U.S. Pat. No. 5,086,191 which are both hereby incorporated by reference in their entirety and for all purposes as if fully set forth herein.

As described above, various Grundmann ketones may be coupled with phosphine oxides such as C to produce the compounds of the inventions in a convergent synthesis approach. Phosphine oxides such as C may be prepared from quinic acid as shown in Scheme III. Scheme III shows the general procedure outlined in U.S. Pat. No. 5,843,928 which is hereby incorporated by reference in its entirety as if fully set forth herein. Modification of the method shown in Scheme III may also be used to produce a large number of vitamin D analogs for use in the present invention as will be apparent to those skilled in the art. For example, a wide variety of phosphonium compounds may be used in place of the $MePh_3P^+Br^-$ used to convert ketone J to alkene K. Examples of such compounds include $EtPh_3P^+Br^-$, $PrPh_3P^+Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in analogous manner to that used to prepare phosphine oxide P of Scheme III. The 2-alkenyl groups of suitable hydroxy-protected 2-alkene and 2-alkene compounds such as compounds 7 (Scheme VB) and 14 (Scheme VIIB) may be reduced with $H_2$ in the presence of $(Ph_3P)_3RhCl$ and then deprotected to provide 2α-alkyl compounds such as 2α-methyl compounds II, III, IV, V, X, and XI. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme III may be used or modified to prepare a wide variety of compounds of the present invention when coupled with an appropriate Grundmann ketone.

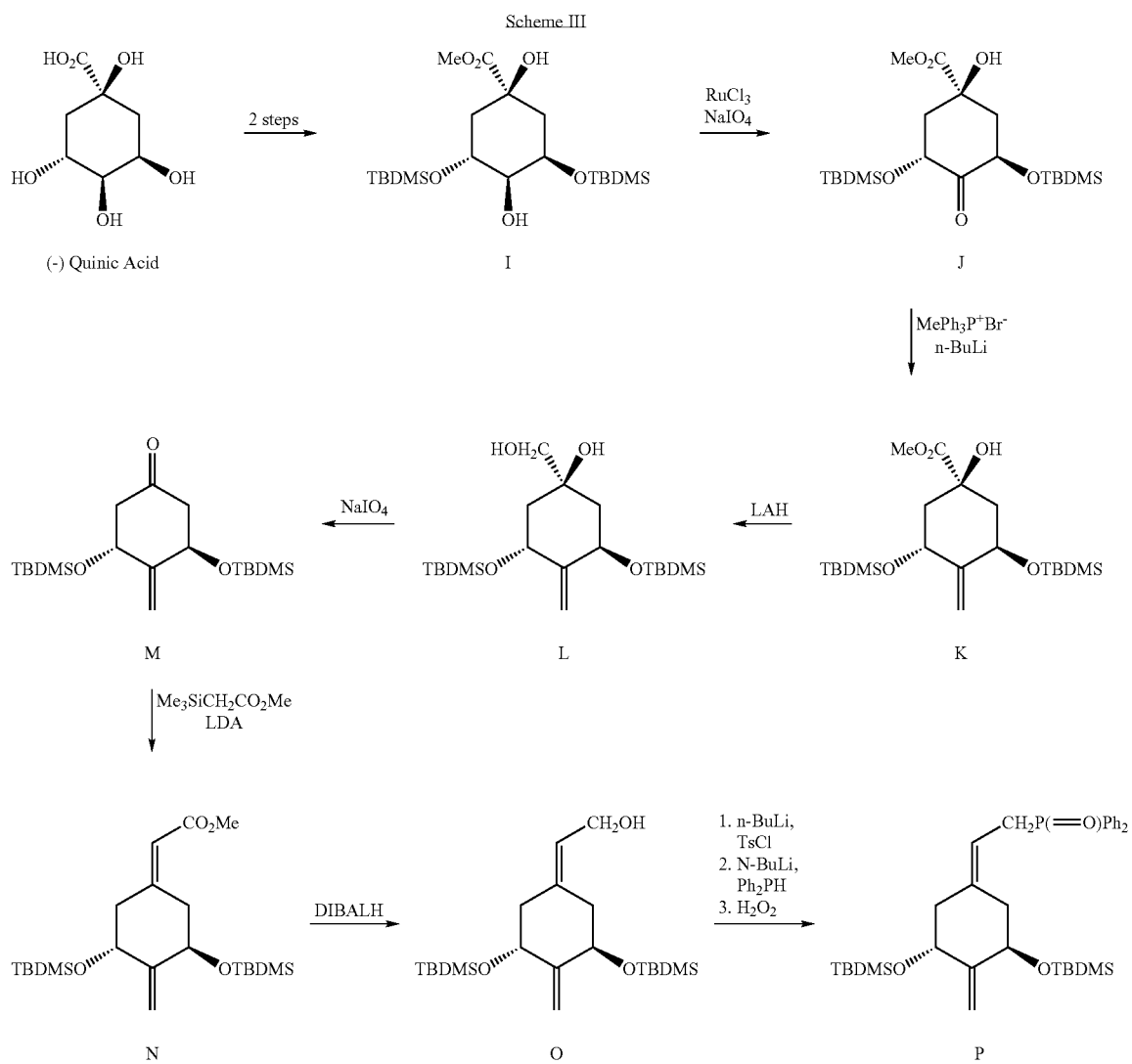

Scheme III

An example of another phosphine oxide useful in preparing the compounds of the invention includes compound Q shown in Scheme IVA. Compound Q is prepared starting from commercially available (Aldrich Chemical, Milwaukee, Wis.) d-carvone (compound R) using the method depicted in Scheme IVB and described by Baggiolini et al. See Baggiolini, E. G. et al., *J. Org. Chem.*, 51, 3098-3108 (1986); Baggiolini, E. G. et al., VITAMIN D: CHEMICAL BIOCHEMICAL AND CLINICAL ENDOCRINOLOGY OF CALCIUM METABOLISM, Proceedings of the Fifth Workshop on Vitamin D, Williamsburg, Va., USA February, 1982, edited by A. W. Norman, K. Schaefer, D. v. Herrath, and H.-G. Grigoleit (Walter de Gruyter, New York, N.Y. 1982); Klein, E. et al., *Tetrahedron*, 19, 1091-1099 (1963) (for stereospecific oxidation to provide compound S); and Martin, J. C. et al., *J. Am. Chem. Soc.*, 93, 2339-2341 (1971); Martin, J. C. et al., *J. Am. Chem. Soc.*, 93, 4327-4329 (1971); and Arhart, R. J. et al., *J. Am. Chem. Soc.*, 94, 4997-5010 (1972) (for synthesis of $Ph_2S(OC(CF_3)_2Ph)_2$) each of which is incorporated by reference in its entirety and for all purposes as if fully set forth herein. As shown in Scheme IVB and described by Baggiolini et al., d-carvone (R) may be stereospecifically epoxidized to provide compound S. Horner-Emmons chemistry is conducted using the carbanion produced from triethylphosphonoacetate to provide ester T. Cleavage of the epoxide ring of T with sodium acetate in acetic acid provides U. Acetylation and oxidative degradation of the side chain using $KIO_4/OsO_4$ followed by Bayer-Villiger oxidation with $CF_3CO_3H$ affords triacetate V1 as described by Baggiolini et al., Saponification of V1 provides V2 which is then selectively protected to provide the bis TBDMS-protected V3 (TBDMS is the t-butyldimethylsilyl protecting group). V3 is dehydrated with dialkoxy diarylsulfurane $Ph_2S(OC(CF_3)_2Ph)_2$ as described by Baggiolini et al. to provide bis TMDMS-protected W. Photoisomerization of W provides X. Allylic alcohol Y1 is produced by reducing X with diisobutylaluminum hydride. Y1 is converted to allylic chloride Y2 which is reacted with lithium diphenylphosphide and then oxidized to provide phosphine oxide Q. Phosphine Oxide Q is used to prepare analogs of 1α,25 dihydroxyvitamin $D_3$ such as compounds XIX, XX, XXI, and XXII by using Q in place of C in the appropriate reactions shown in the following schemes.

Scheme IVA

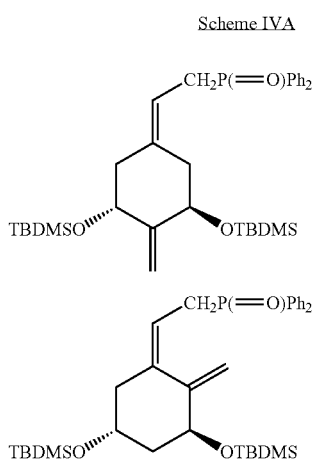

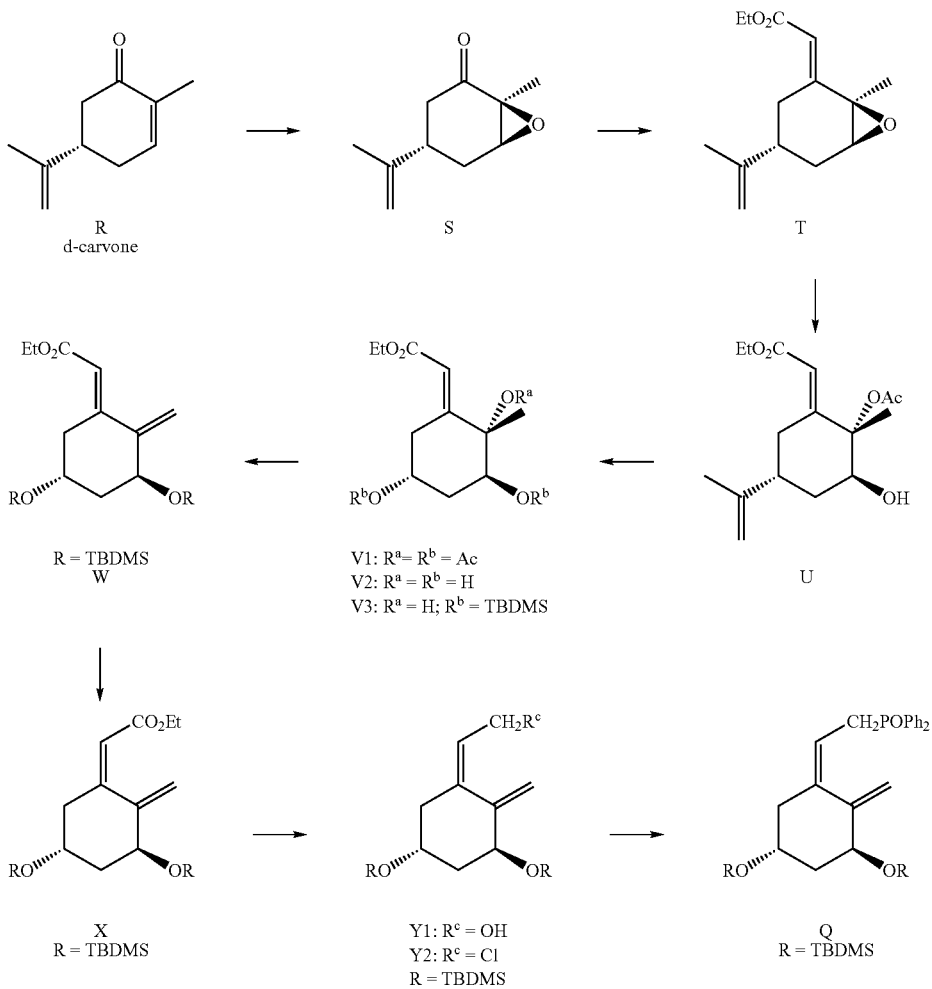

Various compounds of the invention may be prepared by coupling an appropriate Grundmann ketone with a phosphine oxide and then transforming the side chain to provide the desired product as shown in Scheme VA and Scheme VB.

Alternatively, a Grundmann ketone with a complete side chain may be coupled with a phosphine oxide to prepare the compounds of the invention as shown in Schemes VIIA and VIIB. For example, as shown in Scheme VA, ozonolysis of vitamin $D_2$ followed by reduction with sodium borohydride may be used to produce compound 1. Protection followed by oxidation affords Grundmann's ketone 2. Reaction of Grundmann's ketone 2 with phosphine oxide 3 using the conditions shown in Scheme VA provide vitamin D analog 4 which may be transformed into compound 8 using the procedure shown in Scheme VB. As shown in Scheme VB, removal of the protecting group followed by Swern oxidation (oxalyl chloride, DMSO, TEA, $CH_2Cl_2$, −60° C.) provides aldehyde 5. The side chain of a compound such as 5 may then be transformed to provide a variety of compounds of the invention employing standard chemistry such as shown in Scheme VB. For example, reaction of aldehyde 5 with an enolate produced by reaction of ketone 6 with a base such as lithium diisopropylamide in THF provides t-butyidimethylsilyl protected 7 which may then be deprotected to provide compound 8 (compound VII). It will be understood, that cycloalkyl analogs may be used in place of compound 6 to provide cycloalkyl compounds of the invention. The synthetic approach outlined in Schemes VA and VB is used or modified to prepare 24-oxo compounds of the invention including, but not limited to, compounds IV, V, VI, VII, X, XI, XII, and XIII.
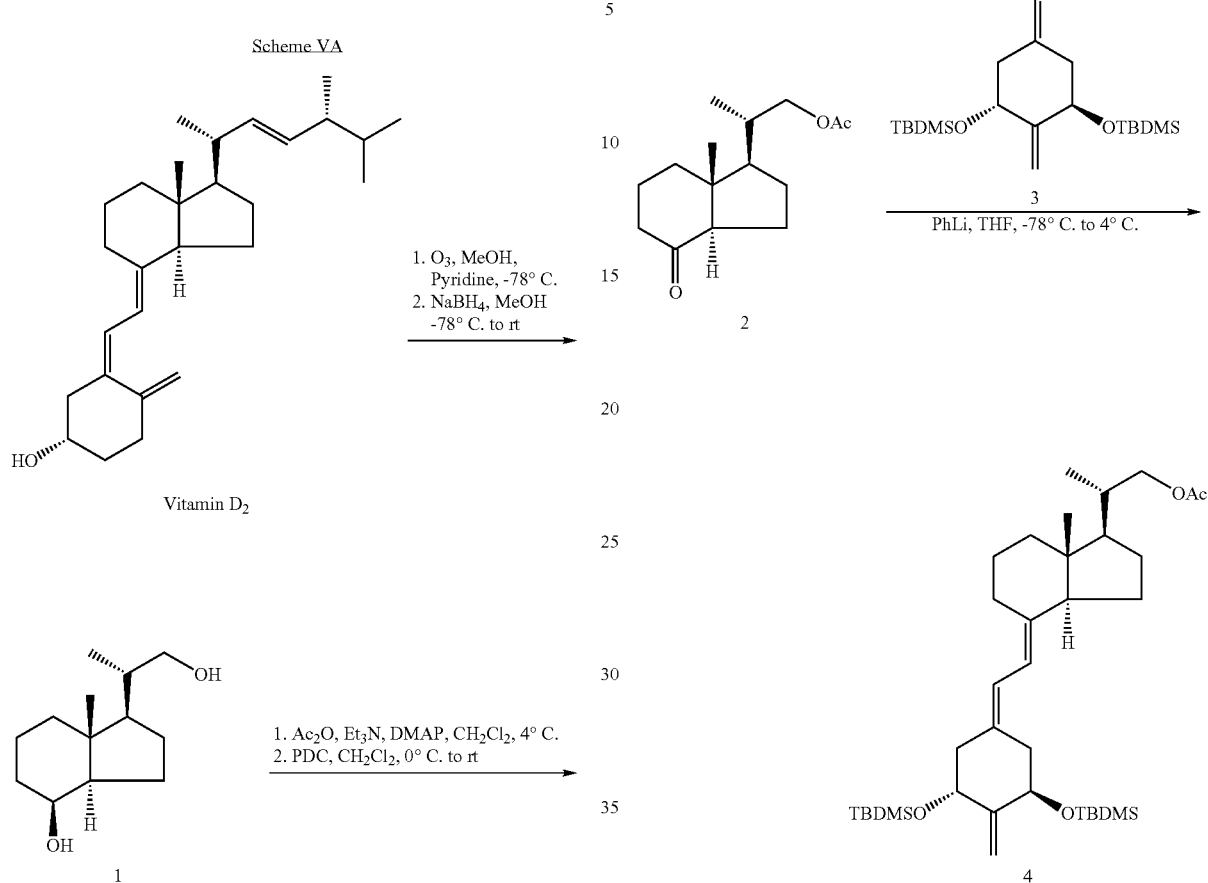

-continued

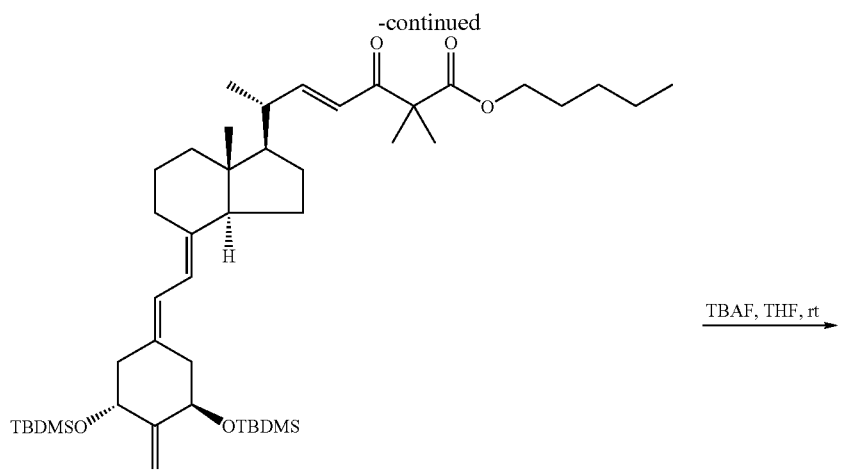

7

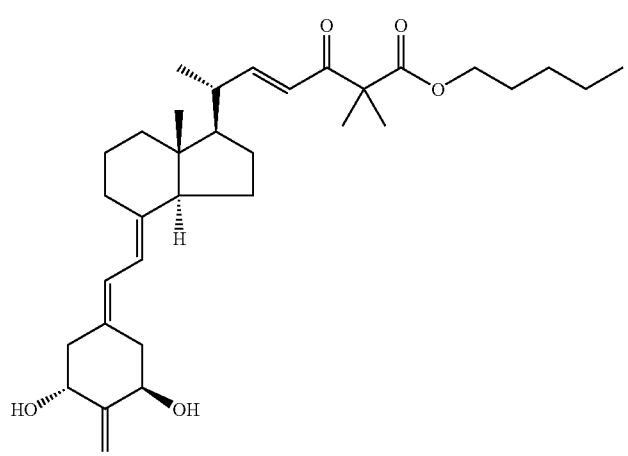

8

Scheme VI shows various methods that may be used to generate cyclopropyl and gem dimethyl compounds that may be used in accordance with Schemes VA and VB, Schemes VIIA and VIIB, Scheme X, and Scheme XI to prepare compounds of the invention.

Scheme VI

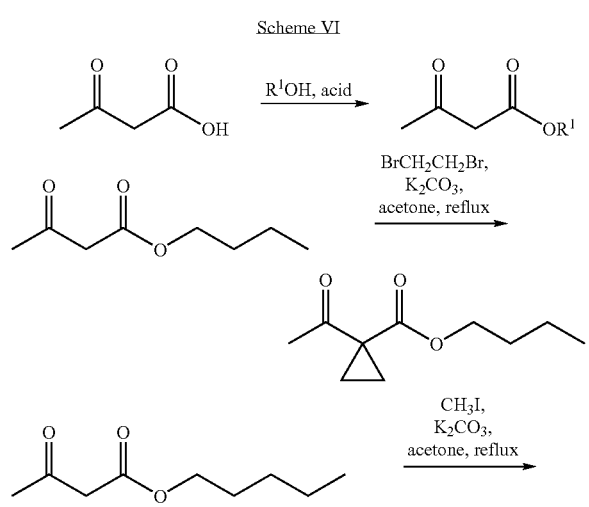

-continued

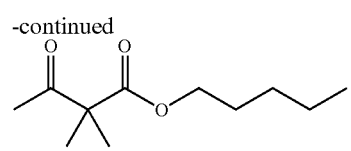

As noted above, various compounds of the invention are prepared by coupling a Grundmann's ketone with a finished side chain with an appropriate phosphine oxide. An example of such a synthetic approach may be used to synthesize compound 15 as shown in Schemes VIIA and VIIB and is used or modified to synthesize 24-hydroxy compounds of the invention including, but not limited to, compounds II, III, VII, and IX. As shown in Scheme VIIA, ozonolysis of vitamin $D_2$ followed by reduction with sodium borohydride may used to produce dihydroxy compound 1 as also shown in Scheme VA. Selective protection of the two hydroxyl groups followed by selective deprotection of the side chain hydroxyl group and oxidation affords triethylsilyl(TES)-protected aldehyde 9 which is suitable for further reaction to provide a Grundmann's ketone with a complete side chain. For example, aldehyde 9 may be reacted with the enolate produced by reaction of ketone 10 with lithium diisopropylamide in tetrahydrofuran (THF) to provide cyclopropyl compound 11. The ketone functional group of compound 11 may be protected to provide compounds with a 24-oxo group or may be reduced ($NaBH_4$, $CeCl_3$, THF, MeOH, 0° C.) to provide hydroxyl compound 12. Removal of the triethylsilyl group with tetrabutylammonium fluoride (TBAF) followed by selective protection of the side chain hydroxyl group using t-butyidimethylsilyl chloride (TBDMSCl) and then oxidation affords TBDMS-protected Grundmann's ketone 13. Reaction of Grundmann's ketone 13 with phosphine oxide 3 under the reaction conditions shown in Scheme VIIB provides TBDMS-protected compound 14 which, upon removal of the TBDMS groups with tetrabutylammonium fluoride (TBAF), affords compound 15 (compound IX). The synthetic route shown in Schemes VIIA and VIIB may also be used to prepare gem dimethyl compounds of the invention using a gem dimethyl compound in place of compound 10 which will be understood by one of skill in the art.

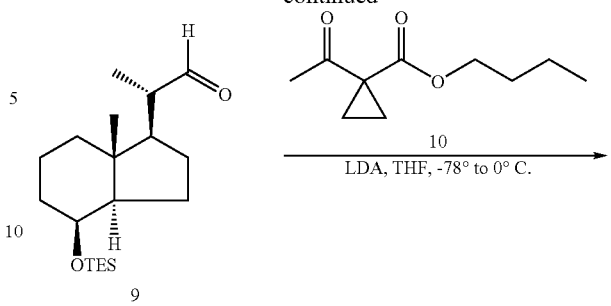

Scheme VIIA

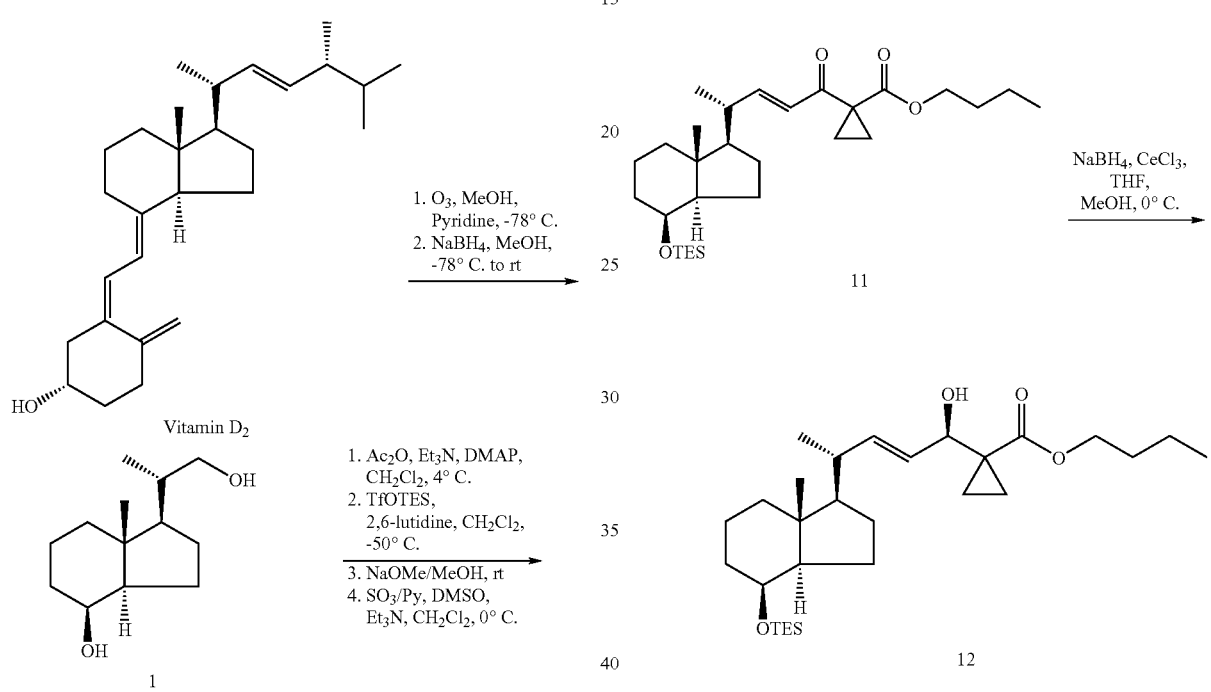

Scheme VIIB

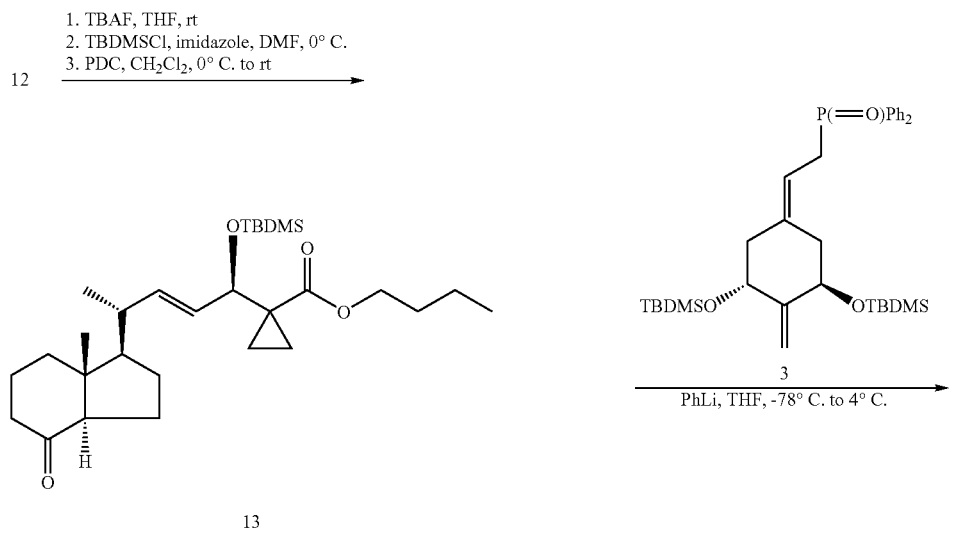

-continued

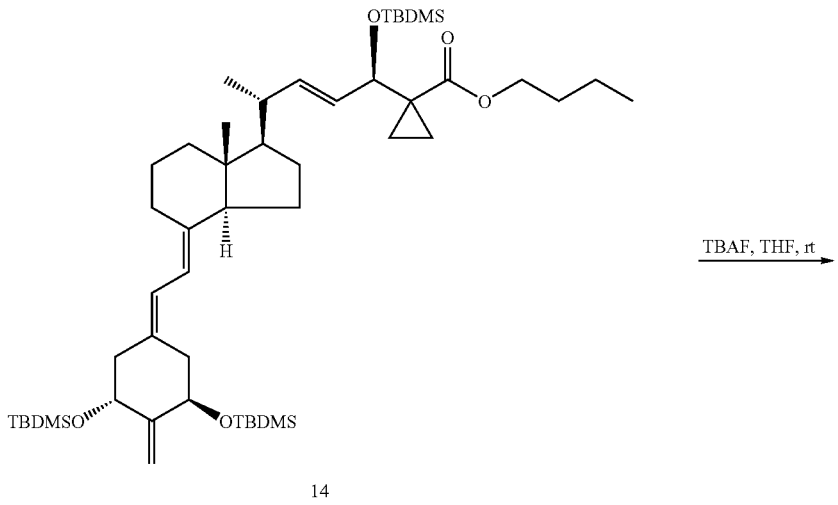

14

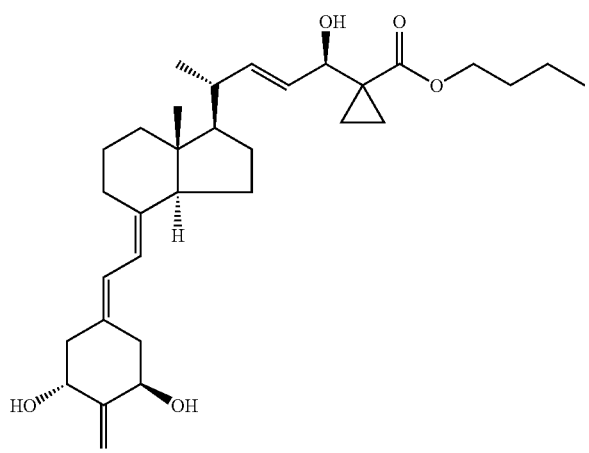

15

The methodology shown in Schemes VIIA and VIIB may also be used to prepare hydroxyketones such as compound 16 as shown in Scheme VIII. As shown in Scheme VIII, reaction of 14 (see Schemes VIIA and VIIB) with a Grignard reagent prepared from 1-chloropentane followed by deprotection provides the desired compound 16. The intermediate product obtained after reaction of the Grignard reagent may alternatively be reduced with $H_2$ in the presence of $(Ph_3P)_3RhCl$ and then deprotected to provide 2α-alkyl compounds such as 2α-methyl compounds of the invention. One skilled in the art will recognize that the procedure outlined in Schemes VIIA, VIIB, and VII may be used with phosphine oxides other than 3 such as, but not limited to, phosphine oxide Q to provide a wide range of compounds of the invention. One skilled in the art will also recognize that a wide range of organic halide compounds such as haloalkanes including, for example bromoalkanes and chloroalkanes may be used in place of 1-chloropentane to provide a wide variety of compounds of the invention.

Scheme VIII

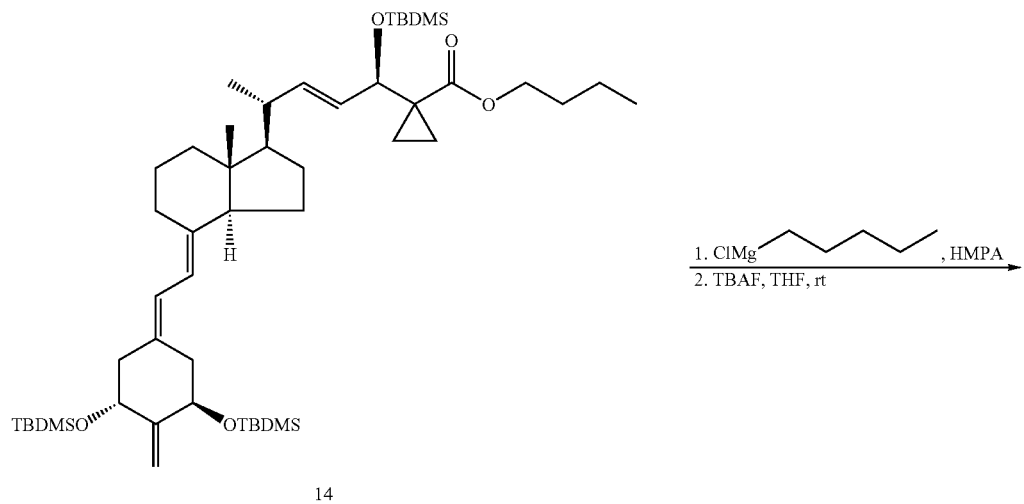

14

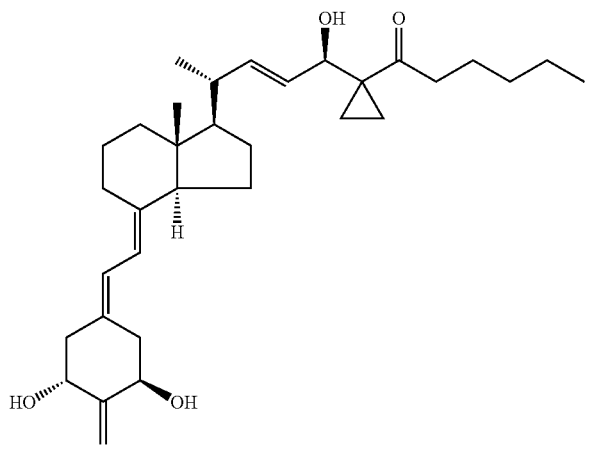

16

The methodology shown in Schemes VA and VB may also be used to prepare diketones such as compounds 18 and 19 as shown in Scheme IXA. As shown in Scheme IXA, reaction of aldehyde 5 (see Schemes VA and VB) with a phosphonate such as compound 17 (see Scheme IXB) provides protected diketone 18 which may be deprotected with tetrabutylammonium fluoride to provide 19 (compound XIII). Bis TBDMS-protected diketone 18 may alternatively be reduced with $H_2$ in the presence of $(Ph_3P)_3RhCl$ and then deprotected to provide 2α-alkyl compounds such as 2α-methyl compounds of the invention. One skilled in the art will recognize that the procedure outlined in Schemes VA, VB, and IXA may be used with phosphine oxides other than 3, for example phosphine oxide Q, to provide a wide range of compounds of the invention. One skilled in the art will also recognize that a wide range of phosphonates may be used in place of 17 to provide various compounds of the invention.

Scheme IXA

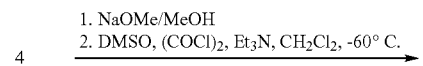

4

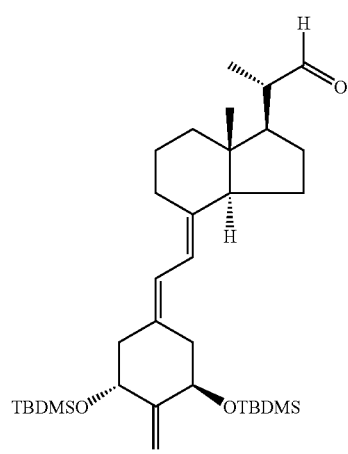

5

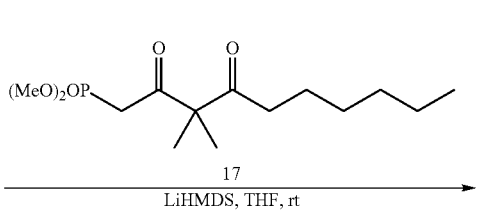

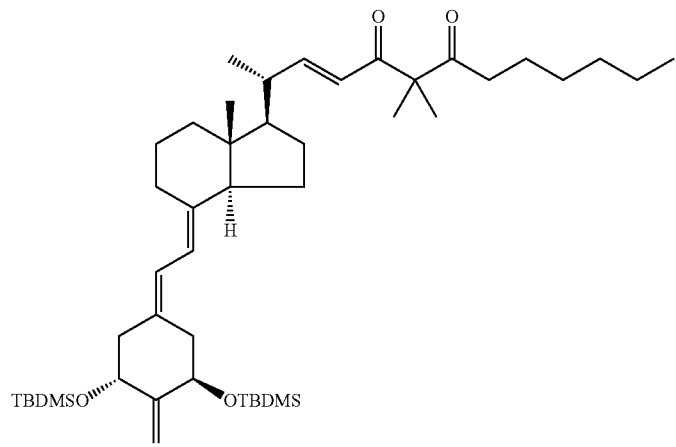

18

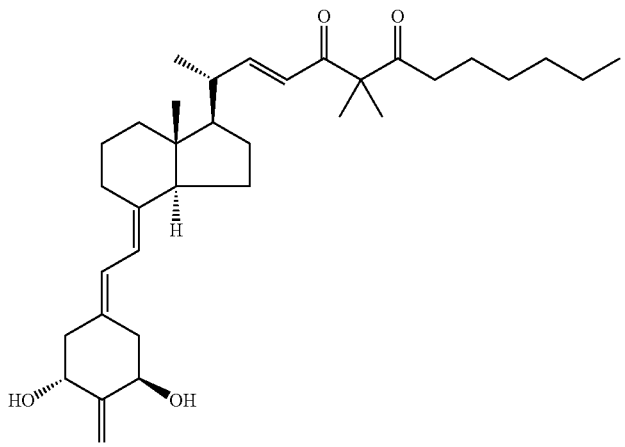

19

As described above, phosphonates such as compound 17 may be used to prepare various diketones of the invention by reaction with an aldehyde such as compound 5 as shown in Scheme IXA or an aldehyde such as compound 30 as shown in Scheme XII. Phosphonate 17 is prepared using standard Arbuzov chemistry such as by reaction of trimethylphosphite with the α-bromoketone shown in Scheme IXB in refluxing solvent.

Scheme IXB

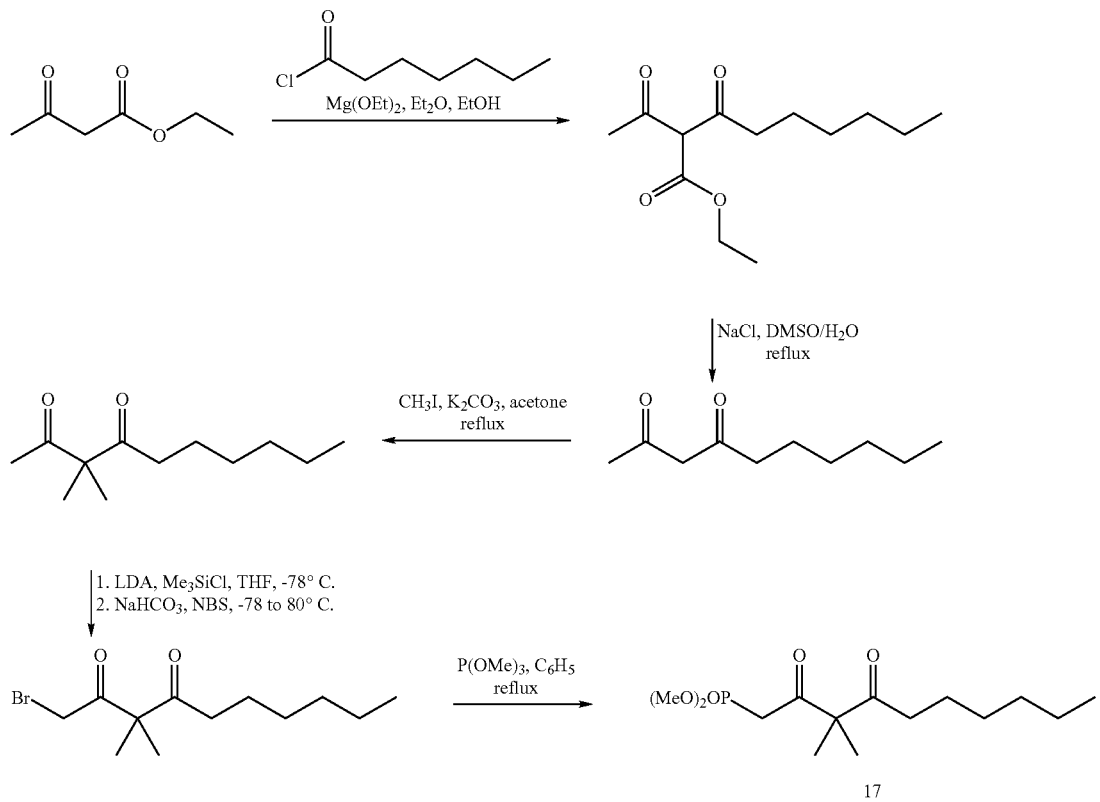

Scheme X sets forth a synthetic route recently disclosed by Fujishima that depicts a method for synthesizing a vitamin D analog where $R^1$ is an n-butyl group. See Fujishima, T. et al. *Bioorg. Med. Chem.*, 11, 3621-3631, (2003) which is hereby incorporated by reference in its entirety and for all purposes as if fully set forth herein. This Scheme is modified and used to synthesize various compounds of the invention.

Scheme X

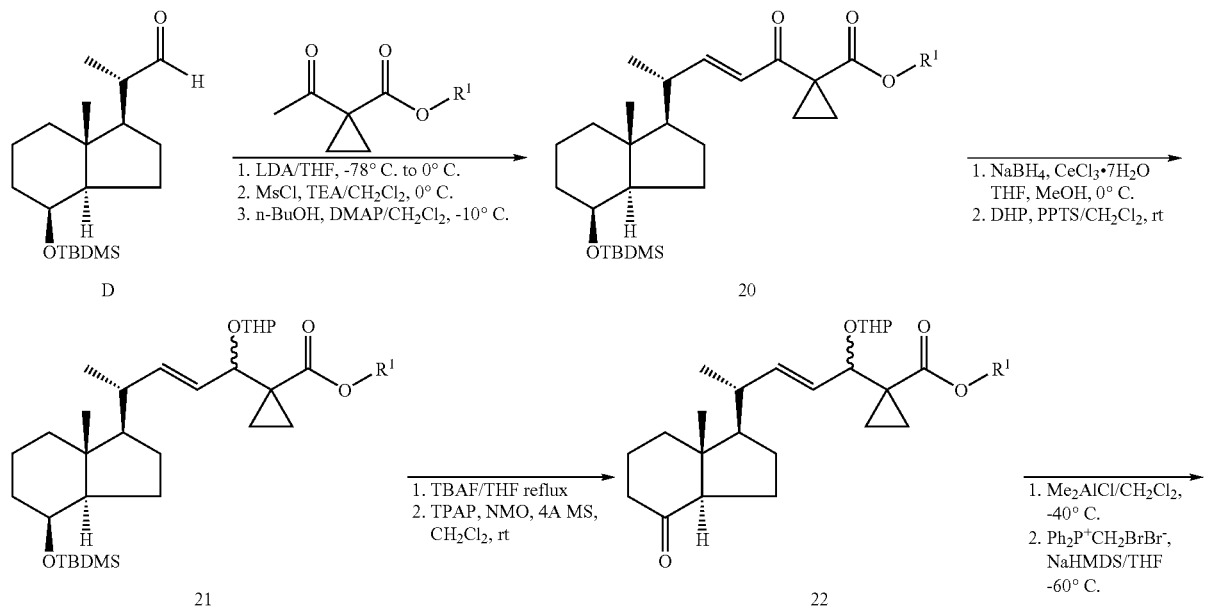

-continued

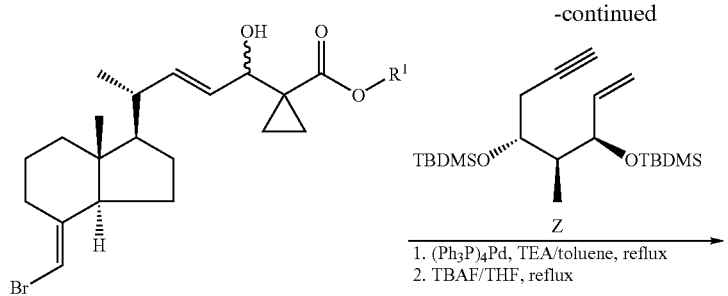

23

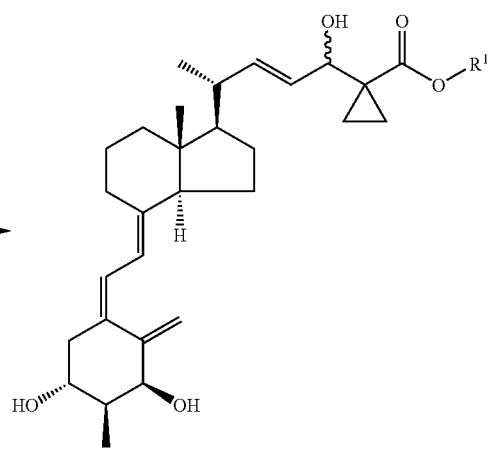

24

$R^1$ = n-butyl.
Fujishima, T. et al. *Bioorganic & Medicinal Chemistry*, 11, 3621–3631 (2003).

Enyne Z is prepared as described in the following references which are all hereby incorporated by reference in their entirety and for all purposes as if fully set forth herein: Konno, K. et al., *Bioorg. Med. Chem. Lett.*, 8, 151 (1998); Fujishima, T, et al., *Bioorg. Med. Chem. Lett.*, 8, 2145 (1998); Konno, K, et al. *J. Med. Chem.*, 43, 4247 (2000); Fujishima, T. et al. *Bioorg. Med. Chem.*, 8, 123 (2000); Nakagawa, K. et al. *Biochem. Pharmacol.*, 59, 691 (2000); and Nakagawa, K. et al. *Biochem. Pharmacol.*, 60, 1937 (2000). Enyne Z may be used to prepare various compounds of the invention such as, but not limited to, compounds XV, XVI, XVII, and XVIII.

Z

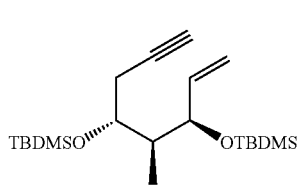

Modification of the synthetic route set forth in Scheme X may be used to prepare various compounds of the invention such as compounds of formula XV, XVI, XVII, and XVIII. For example, as shown in Scheme XI, compound 23 may be prepared using the procedure of Scheme X and described by Fujishima, T. et al. Compound 23 may then be protected using TBDMSCl and then converted to compound 25 by reaction with enyne Z following the procedure shown in Scheme XI. Reaction of 25 with the Grignard reagent prepared from 1-chloropentane using HMPA (hexamethylphosphoramide) followed by deprotection with tetrabutylammonium fluoride (TBAF) affords compounds 26 (compound XVIII).

Scheme XI

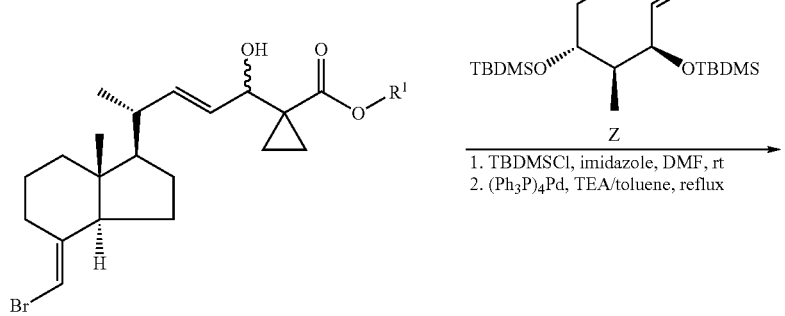

23
$R^1$ = n-butyl.

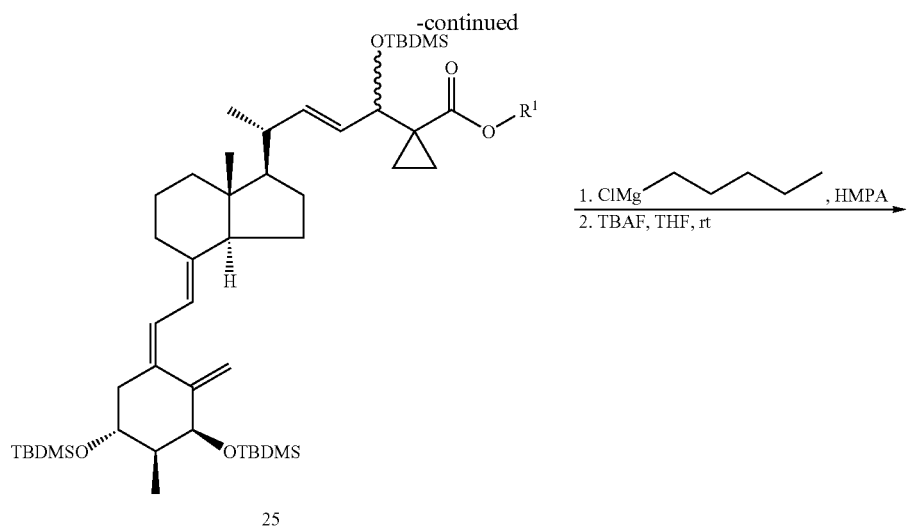

25

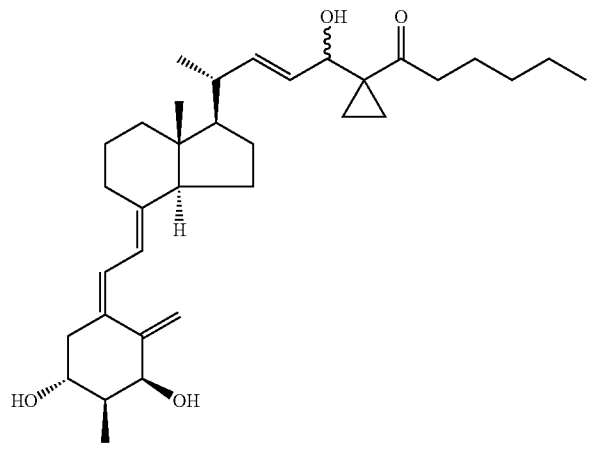

26

Enyne Z may also be used to synthesize various compounds of the invention, including, but not limited to compounds XV and XVI. For example, Scheme XII shows a synthetic route that may be employed to prepare compound XVI. Compound 2 is first prepared as shown in Scheme VA. Reaction of ketone 2 with the ylid prepared from Ph₃P⁺CH₂Br Br⁻ using the sodium salt of hexamethyldisilazane (HMDS or (CH₃)₃SiNHSi(CH₃)₃) in THF at −60° C. provides vinyl bromide 27. Reaction of vinyl bromide 27 with enyne Z using the method described in Fujishima, T. et al. for the synthesis of compound 24 of Scheme X affords compound 28. Removal of the protecting group followed by Swern oxidation provides aldehyde 29. Aldehyde 29 may be used to prepare many compounds of the present invention. For example, as shown in Scheme XII, aldehyde 29 reacts with the anion of phosphonate 17, prepared as shown in Scheme IXB, to produce the diketone intermediate. Removal of the TBDMS protecting groups with TBAF in THF at room temperature affords compound 30 (compound XVI).

Scheme XII

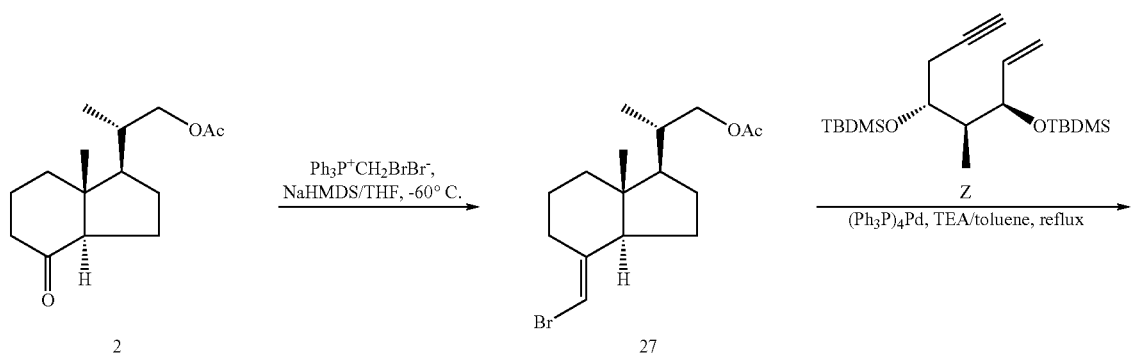

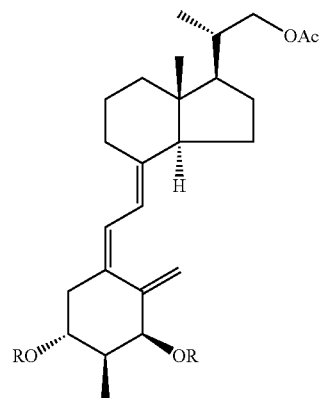

R = TBDMS  28

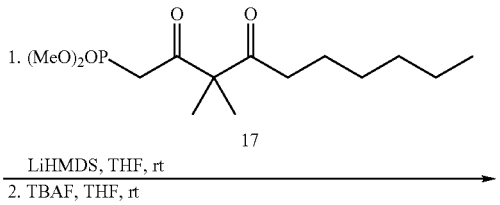

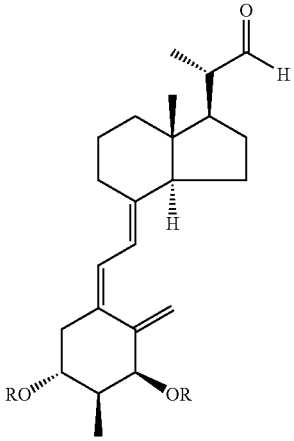

R = TBDMS  29

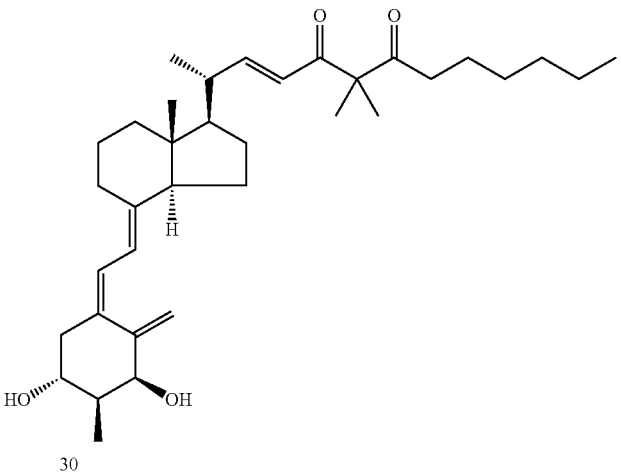

30

EXAMPLES

Synthesis of Specific Vitamin D Analogs

Synthesis of (22E)-(20S,24R)-25-carbobutoxy-2α-methyl-26,27-cyclo-22-dehydro-1α,24-dihydroxy-19-norvitamin $D_3$ (II)

Compound II is prepared using the same procedure used to prepare compound VIII except that the 20-epi compound 14 of Scheme VIIB is reduced with $H_2$ in the presence of $(Ph_3P)_3RhCl$ and is then deprotected to afford the title compound.

Synthesis of (22E)-(24R)-25-carbobutoxy-2α-methyl-26,27-cyclo-22-dehydro-1α,24-dihydroxy-19-norvitamin $D_3$ (III)

Compound III is prepared using the same procedure used to prepare compound IX except that compound 14 of Scheme VIIB is reduced with $H_2$ in the presence of $(Ph_3P)_3RhCl$ and is then deprotected to afford the title compound.

Synthesis of (22E)-(20S)-25-carbopentoxy-2α-methyl-24-oxo-22-dehydro-1α-hydroxy-19-norvitamin D₃ (IV)

Compound IV is prepared using the same procedure used to prepare compound VI except that the 20-epi compound 7 of Scheme VB reduced with H₂ in the presence of (Ph₃P)₃RhCl and is then deprotected to afford the title compound.

Synthesis of (22E)-25-carbopentoxy-2α-methyl-24-oxo-22-dehydro-1α-hydroxy-19-norvitamin D₃ (V)

Compound V is prepared using the same procedure used to prepare compound VII except that compound 7 of Scheme VB reduced with H₂ in the presence of (Ph₃P)₃RhCl and is then deprotected to afford the title compound.

Synthesis of (22E)-(20S)-25-carbopentoxy-2-methylene-24-oxo-22-dehydro-1α-hydroxy-19-norvitamin D₃ (VI)

Compound VI is prepared using the synthetic route depicted in Schemes VA and VB with the modification that compound 1 of Scheme VA is epimerized by reaction with tetrabutylammonium hydroxide using a procedure similar to that shown in Scheme I and Scheme II. After silyl group removal, the diastereomers are separated by chromatography, and the 20-epi compound 1 is used in place of compound 1 in Scheme VA.

Synthesis of (22E)-25-carbopentoxy-2-methylene-24-oxo-22-dehydro-1α-hydroxy-19-norvitamin D₃ (VII)

Compound VII is prepared using the synthetic route depicted in Schemes VA and VB.

Synthesis of (22E)-(20S,24R)-25-carbobutoxy-2-methylene-26,27-cyclo-22-dehydro-1α,24-dihydroxy-19-norvitamin D₃ (VII)

Compound VII is prepared using the synthetic route depicted in Schemes VIIA and VIIB with the modification that compound 9 of Scheme VIIA is epimerized by reaction with tetrabutylammonium hydroxide using a procedure similar to that shown in Scheme I. The epimers are separated by chromatography, and the 20-epi compound 9 is used in place of compound 9 in Schemes VIIA and VIIB.

Synthesis of (22E)-(24R)-25-Carbobutoxy-2-methylene-26,27-cyclo-22-dehydro-1α,24-dihydroxy-19-norvitamin D₃ (IX) (OU-72) and (22E)-(24R)-24-Butoxy-25-carbobutoxy-2-methylene-26,27-cyclo-22-dehydro-1α-hydroxy-19-norvitamin D₃ (CN-67)

Compound IX is prepared using the same basic synthetic route depicted in Schemes VIIA and VIIB as described and specifically shown in Schemes XII and XIV.

Des-A,B-23,24-dinorcholane-8β,22-diol (1)

A solution of vitamin D₂ (10 g, 25.4 mmol) in methanol (600 mL) and pyridine (7 mL) was cooled to −78° C. while purging with argon. The argon stream was stopped and a stream of ozone was passed until a blue color appeared. The solution was purged with oxygen until the blue color disappeared and was then treated with NaBH₄ (2.4 g, 64 mmol). After 20 minutes, the second portion of NaBH₄ (2.4 g, 64 mmol) was added, and the reaction was allowed to warm to room temperature. The third portion of NaBH₄ (2.4 g, 64 mmol) was added, and the reaction mixture was stirred at room temperature overnight. The reaction was quenched with 100 mL of water and concentrated under vacuum. The residue was extracted with methylene chloride (3×150 mL). The organic phase was washed with a 1 M aqueous solution of HCl (2×150 mL), saturated aqueous solution of NaHCO₃ (100 mL), dried over anhydrous MgSO₄ and concentrated under vacuum. The residue was purified by flash chromatography (20-30% ethyl acetate/hexane) to yield 4.11 g (19.4 mmol, 76% yield) of 1 as white crystals. [α]$_D$=+56.0 (c 0.95, CHCl₃); mp 110-111° C.; ¹H NMR (400 MHz, CDCl₃) δ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); ¹³C NMR (100 MHz, CDCl₃) δ 13.6, 16.6, 17.4, 22.6, 26.6, 33.5, 38.2, 40.2, 41.3, 52.3, 52.9, 67.8, 69.2; MS (EI) m/z 212 (2, M⁺), 194 (17), 179 (18), 163 (10), 135 (19), 125 (34), 111 (100); exact mass calculated for C₁₃H₂₂O ([M-H₂O]⁺) 194.1671, found 194.1665.

Des-A,B-22-(acetoxy)-23,24-dinorcholane-8β-ol (2)

To a stirred solution of 1 (3.50 g, 16.5 mmol) and DMAP (100 mg) in triethylamine (3.00 mL, 1.67 g, 21.6 mmol) and methylene chloride (300 mL) was added dropwise acetic anhydride (1.54 mL, 2.18 g, 16.5 mmol) at 0° C. The reaction mixture was kept at 4° C. overnight. Solvents were removed under reduced pressure, and the residue was redissolved in methylene chloride (200 mL), washed with 10% aqueous solution of HCl (50 mL), saturated aqueous solution of NaHCO₃ (50 mL) and water (50 mL). The organic phase was dried over anhydrous Na₂SO₄ and concentrated under reduced pressure to give 4.06 g (16.0 mmol; 97% yield) of 2 as white crystals. [α]$_D$=+33.7 (c 0.90), CHCl₃); mp 78-80° C.; ¹H NMR (500 MHz, CDCl₃) δ 0.96 (3H, s), 1.00 (3H, d, J=6.6 Hz), 2.05 (3H, s), 3.77 (1H, dd, J=10.6 Hz, J=7.7 Hz), 4.06 (1H, dd, J=10.6 Hz, J=3.3 Hz), 4.11 (1H, br s); ¹³C NMR (100 MHz, CDCl₃) 613.5, 17.0, 17.4, 21.0, 22.5, 26.6, 33.5, 35.3, 40.2, 41.9, 52.3, 53.2, 69.1, 69.4, 171.4; MS (EI) m/z 254 (M⁺, 2), 236 (5), 205 (2), 194 (12), 176 (22), 161 (14), 135 (16), 125 (34), 111 (100); exact mass (ESI) calculated for C₁₅H₂₃O₃Na ([M+Na]⁺) 277.1780, found 277.1791.

Des-A,B-22-(acetoxy)-8β-[(triethylsilyl)oxy]-23,24-dinorcholane (3)

To a stirred solution of 2 (4.00 g, 16.6 mmol) in methylene chloride (40 mL) and 2,6-lutidine (2.67 mL, 2.46 g, 23.0 mmol), was added dropwise triethylsilyl trifluoromethanesulfonate (4.52 mL, 5.28 g, 20.0 mmol) under argon at −50° C. After 30 minutes, wet methylene chloride (5 mL) and water (80 mL) were added. The reaction mixture was extracted with methylene chloride (3×120 mL) and organic phase was washed with a saturated aqueous solution, of CuSO₄ (50 mL), dried over anhydrous Na₂SO₄ and concentrated under reduced pressure to give crude 3 as an oil. [α]D+42.2 (c 1.25, CHCl₃); ¹H NMR (500 MHz, CDCl₃) δ 0.55 (6H, q, J=7.9 Hz), 0.93 (3H, s), 0.95 (9H, t, J=8.0 Hz), 0.98 (3H, d, J=6.6 Hz), 2.05 (3H, s), 3.77 (1H, dd, J=10.6 Hz, J=7.5 Hz), 4.04-4.07 (2H, m); ¹³C NMR (125 MHz, CDCl₃) δ 4.9, 6.9, 13.5, 17.1, 17.6, 21.0, 23.0, 26.8, 34.6, 35.4, 40.6, 42.2, 52.8, 53.4, 69.2, 69.6, 171.4; MS (EI) m/z 368 (M⁺, 4), 339 (30), 325 (15), 177 (89), 145 (100); exact mass calculated for C₂,H₄₀O₃Si 368.2747, found 368.2748.

Des-A,B-8β-[(triethylsilyl)oxy]-23,24-dinorcholane-22-ol (4)

To a stirred solution of crude 3 in methanol (100 mL) 10% solution of sodium methanolate in methanol (20 mL) was added dropwise. After 2 hours, a saturated aqueous solution of NH$_4$Cl (20 mL) and water (60 mL) were added, and the mixture was extracted with CH$_2$Cl$_2$ (5×100 mL). The organic phase was dried over anhydrous Na$_2$SO$_4$, concentrated under reduced pressure, and the residue was purified on silica gel column (10-20% ethyl acetate/hexane) to give 5.25 g (16.1 mmol; 97% from 2) of 4. [α]D=+40.3 (c 1.00, CHCl$_3$); $^1$H NMR δ 0.55 (6H, q, J=7.9 Hz), 0.93-0.97 (12H, m), 1.02 (3H, d, J=6.6 Hz), 3.37 (1H, dd, J=10.4 Hz, J=6.8 Hz), 3.63 (1H, dd, J=10 Hz, J=3.0 Hz), 4.04 (1H, d, J=1.8 Hz); $^{13}$C NMR (100 MHz, CDCl$_3$) δ 4.9, 6.9, 13.6, 16.6, 17.6, 23.0, 26.8, 34.6, 38.3, 40.6, 42.1, 52.8, 53.1, 68.0, 69.3; MS (EI) m/z 326 (M$^+$, 10), 311 (2), 297 (93), 283 (36), 225 (16), 193 (21), 177 (100); exact mass calculated for C$_{19}$H$_{38}$O$_2$Si 326.2641, found 326.2639.

Des-A,B-8β-[(triethylsilyl)oxy]-23,24-dinorcholane-22-al (5)

Sulfur trioxide pyridine complex (3.71 g, 23.3 mmol) was added to the stirred solution of 4 (1.16 g, 3.56 mmol) in triethylamine (2.73 mL, 1.97 g, 19.5 mmol), anhydrous DMSO (4.0 mL) and anhydrous CH$_2$Cl$_2$ (20 mL) at 0° C. under argon. After 20 minutes, methylene chloride (80 mL) was added and the reaction mixture was washed with a saturated aqueous solution of CuSO$_4$ (20 mL) and water (20 mL). The organic phase was dried over anhydrous Na$_2$SO$_4$, concentrated under reduced pressure, and the residue was purified on silica gel (0.5-2% ethyl acetate/hexane) to give 900 mg (2.78 mmol; 78% yield) of 5. [α]$_D$=+42.6 (c 1.15, CHCl$_3$); $^1$H NMR (400 MHz, CDCl$_3$) δ 0.57 (6H, q, J=7.9 Hz), 0.94-0.98 (12H, m), 1.10 (3H, d, J=6.8 Hz), 2.35 (1H, m), 4.07 (1H, d, J=2.5 Hz), 9.58 (1H, d, J=3.2 Hz); $^{13}$C NMR MHz, CDCl$_3$) δ 5.0, 6.9, 13.4, 13.9, 17.6, 23.3, 26.2, 34.6, 40.6, 42.7, 49.1, 51.8, 52.5, 53.2, 69.1, 205.3; MS (EI) m/z 324 (M$^+$, 4), 311 (12), 295 (100); exact mass calculated for C$_{17}$H$_{31}$O$_2$Si ([M-C$_2$H$_5$]$^+$) 295.2093, found 295.2086.

(22E)-Des-A,B-25-carbobutoxy-24-oxo-8β-[(triethylsilyl)oxy]-26,27-cyclo-22-dehydrocholestan (6)

To a stirred solution of 1-[2-(Dimetoxy-phosphoryl)-acetyl]-cyclopropanecarboxylic acid n-butyl ester (17) (520 mg; 1.78 mmol) in THF (4 mL), was added dropwise 1 M LiHMDS in THF (1.60 mL; 1.60 mmol). After 1 hour, a solution of 5 (470 mg; 1.45 mmol) in THF (4 mL) was added via cannula. The reaction mixture was stirred for 27 hours. A saturated aqueous solution of NH$_4$Cl (5 mL), brine (5 mL), and water (10 mL) were then added at 0° C., and the resulting mixture was extracted with diethyl ether (3×50 mL). The organic phase was dried over anhydrous MgSO$_4$, concentrated under reduced pressure, and the residue was purified by column chromatography (1-8% ethyl acetate/hexane) to give 632.2 mg (1.29 mmol; 89% yield) of 6. [α]D=+65.2 (c 1.10, CHCl$_3$); UV (hexane) λ$_{max}$=229 nm, ε$_{max}$=15000; $^1$H NMR MHz, CDCl$_3$) δ 0.54 (6H, q, J=7.9 Hz), 0.90-0.95 (15H, m), 1.06 (3H, d, J=6.6 Hz), 4.03 (1H, br d, J=2.3 Hz), 4.12 (2H, m), 6.40 (1H, d, J=15.5 Hz), 6.72 (1H, dd, J=15.5 Hz, J=8.9 Hz); $^{13}$C NMR (125 MHz, CDCl$_3$) δ 4.9, 6.9, 13.6, 13.8, 17.3, 17.4, 17.6, 19.0, 19.2, 23.0, 27.3, 30.6, 34.1, 34.5, 39.5, 40.6, 42.5, 52.9, 55.6, 65.2, 69.2, 126.1, 153.2, 171.7, 194.3; MS (EI) m/z 490 (M$^+$, 32), 461 (72), 447 (21), 417 (11), 405 (17), 387 (25), 358 (37), 295 (66), 225 (49), 175 (100); exact mass (ESI) calculated for C$_{29}$H$_{50}$O$_4$SiNa ([M+Na]$^+$) 513.3376, found 513.3370.

(22E)-Des-A,B-25-carbobutoxy-24-oxo-26,27-cyclo-22-dehydrocholestan-8β-ol (7)

To a stirred solution of 6 in n-butyl alcohol (25 mL), was added (1S)-(+)-10-camphorsulfonic acid at 0° C. The reaction mixture was kept at room temperature for 30 hours. A saturated aqueous solution of NaHCO$_3$ (10 mL) and water (10 mL) were then added, and the mixture was extracted with diethyl ether (3×40 mL). The organic phase was dried over anhydrous MgSO$_4$, concentrated under reduced pressure, and the residue was purified on silica gel Sep-Pack cartridge (5-25% ethyl acetate/hexane) to give 461 mg (1.23 mmol; 96% yield) of 7. [α]$_D$=+49.2 (c 0.75, CHCl$_3$); $^1$H NMR (400 MHz, CDCl$_3$) δ 0.93 (3H, t, J=7.4 Hz), 0.98 (3H, s), 1.08 (3H, d, J=6.6 Hz), 4.09 (1H, s), 4.13 (2H, t, J=6.6 Hz), 6.44 (1H, d, J=15.5 Hz), 6.75 (1H, dd, J=15.5 Hz, J=8.9 Hz); $^{13}$C NMR (100 MHz, CDCl$_3$) δ 13.7, 13.8, 17.4, 17.5, 19.0, 19.1, 22.5, 27.2, 30.5, 33.6, 33.8, 39.5, 40.3, 42.2, 52.4, 55.5, 65.2, 69.1, 126.2, 152.7, 171.6, 194.2; MS (EI) m/z 376 (M$^+$, 76), 358 (5), 303 (10), 251 (16), 224 (100); exact mass calculated for C$_{23}$H$_{36}$O$_4$ 376.2614, found 376.2613.

(22E)-(24R)-Des-A,B-25-carbobutoxy-26,27-cyclo-22-dehydrocholestan-8β,24-diol (8)

To a stirred solution of 7 in THF (2.5 mL), were added EtOH (7.5 mL), CeCl$_3$x7H$_2$O (710 mg, 1.90 mmol), and NaBH$_4$ (130 mg, 3.44 mmol). After 20 minutes, a saturated aqueous solution of NH$_4$Cl (5 mL) and water (5 mL) were added, and the mixture was extracted with ethyl acetate (3×40 mL). The organic phase was dried over anhydrous MgSO$_4$, concentrated under reduced pressure, and the residue was purified by column chromatography (5-30% ethyl acetate/hexane) to give 104 mg (0.28 mmol, 23% yield) of 8 and 235 mg (0.62 mmol, 51% yield) of the 24S isomer. [α]D=+36.0 (c 1.05, CHCl$_3$); $^1$H NMR (500 MHz, CDCl$_3$) δ 0.93 (3H, t, J=7.3 Hz), 0.95 (3H, s), 1.01 (3H, d, J=6.6 Hz), 3.16 (1H, d, J=7.1 Hz), 3.96 (1H, t, J=6.7 Hz), 4.09 (2H, t, J=6.6 Hz), 5.41 (1H, dd, J=15.4 Hz, J=6.7 Hz), 5.48 (1H, dd, J=15.4 Hz, J=8.4 Hz); $^{13}$C NMR (125 MHz, CDCl$_3$) δ 11.7, 13.7, 14.7, 17.8, 19.1, 20.1, 22.5, 27.5, 28.4, 29.7, 30.5, 33.5, 39.5, 40.2, 41.8, 52.6, 56.0, 64.5, 69.3, 126.3, 139.8, 174.8. MS (EI) m/z 378 (M$^+$, 3), 360 (7), 342 (2), 287 (7), 197 (100); exact mass (ESI) calculated for C$_{23}$H$_{38}$O$_4$Na ([M+Na]$^+$) 401.2668, found 401.2648.

(22E)-Des-A,B-25-carbobutoxy-24-[(triethylsilyl)oxy]-26,27-cyclo-22-dehydrocholestan-8β-ol (9)

To a stirred solution of 8 (54 mg. 140 mmol) in triethylamine (60 μL, 44 mg, 0.43 mmol) and methylene chloride (2 mL), was added dropwise triethylsilyl chloride (45 μL, 40 mg, 27 mmol) at 0° C. The reaction mixture was stirred at room temperature for 22 hours and purified on silica gel Sep-Pack cartridge (2-30% ethyl acetate/hexane) to give 36 mg (73 μmol, 52% yield), 10 mg (17 μmol, 12% yield) of (22E)-des-A,B-25-carbobutoxy-8β,24-di[(triethylsilyl)oxy]-26,27-cyclo-22-dehydrocholestan, 9 mg (24 μmol, 17% yield) of 8 and traces of (22E)-(24R)-des-A,B-25-carbobutoxy-8β-[(triethylsilyl)oxy]-26,27-cyclo-22-dehydrocholestan-24-ol. [α]$_D$=−2.4 (c 0.85, CHCl$_3$); $^1$H NMR (400 MHz, CDCl$_3$) δ 0.57 (6H, q, J=7.9 Hz), 0.93 (9H, t, J=7.9 Hz), 0.95 (3H, s), 1.00 (3H, d, J=6.6 Hz), 4.04 (2H, m), 4.11 (1H, s), 4.68 (1H, d, J=7.2 Hz), 5.26 (1H, dd, J=15.3 Hz, J=7.2 Hz), 5.43 (1H, dd, J=15.3 Hz, J=8.6 Hz); $^{13}$C NMR (100 MHz, CDCl$_3$) δ 5.0, 6.8, 10.2, 11.9, 13.6, 13.7, 17.4, 19.2, 19.9, 22.5, 27.4, 29.2, 30.7, 33.5, 39.5, 40.3, 41.8, 52.6, 56.1, 64.1, 69.3, 70.5, 128.5, 138.0, 174.0. MS (EI) m/z 492 (M$^+$, 2), 463 (100), 389 (14), 311 (58); exact mass (ESI) calculated for C$_{29}$H$_{52}$O$_4$SiNa ([M+Na]$^+$) 515.3533, found 515.3549.

(22E)-Des-A,B-25-carbobutoxy-24-[(triethylsilyl)oxy]-26,27-cyclo-22-dehydrocholestan-8β-one (10)

To a stirred solution of 9 (36 mg, 73 μmol) and PPTS (5 crystals), was added PDC (70 mg, 186 μmol) at 0° C. The cooling bath was then removed, and the reaction mixture was stirred for 2 hours. Solvent was then removed under reduced pressure, and the residue was purified on silica gel Sep-Pack cartridge (5-10% ethyl acetate/hexane) to give 30 mg (61 μmol, 84% yield) of 10. [α]$_D$=−23.5 (c 1.45, CHCl$_3$); $^1$H NMR (400 MHz, CDCl$_3$) δ 0.56 (6H, q, J=7.8 Hz), 0.63 (3H, s), 0.92 (9H, t, J=7.8 Hz), 1.04 (3H, d, J=6.6 Hz), 4.02 (2H, td, J=6.6 Hz, J=2.4 Hz), 4.7 (1H, d, J=7.0 Hz), 5.29 (1H, dd, J=15.3 Hz, J=7.0 Hz), 5.45 (1H, dd, J=15.3 Hz, J=8.7 Hz); $^{13}$C NMR MHz, CDCl$_3$) δ 5.0, 6.8, 10.1, 12.1, 12.7, 13.7, 19.1, 19.2, 20.2, 24.0, 27.6, 30.7, 38.8, 39.6, 41.0, 49.8, 56.1, 62.0, 64.1, 70.2, 129.2, 137.1, 173.9, 211.9; MS (EI) m/z 490 (M$^+$, 3), 461 (100), 405 (14), 387 (21), 311 (43); exact mass calculated for C$_{29}$H$_{50}$O$_4$SiNa ([M+Na]$^+$) 513.3376, found 513.3391.

(22E)-(24R)-25-Carbobutoxy-2-methylene-26,27-cyclo-22-dehydro-1α,24-dihydroxy-19-norvitamin D$_3$ (13)

To a stirred solution of 11 (75 mg, 125 μmol) in THF (1 mL), was added a 1.2 M solution of PhLi in cyclohexane/ether 7:3 (20 μL) at −25° C. until a deep orange color was stable. A second portion of PhLi solution (95 μL, 115 μmol) was added, and the mixture was stirred for 30 minutes. The mixture was then cooled to −78° C. and a precooled solution of 10 (26 mg, 53 μmol) in THF (400 μL) was added via cannula. The reaction mixture was stirred for 3 hours and then warmed to 4° C. and stirred overnight. Ethyl acetate (20 mL) was added and organic phase was washed with brine (5 mL), dried over anhydrous MgSO$_4$, and concentrated under reduced pressure. The residue was purified on silica gel Sep-Pack cartridge (hexane—2% ethyl acetate/hexane) to give 49 mg of crude 12. Unreacted 11 (21 mg) was recovered washing Sep-Pack cartridge with 5-10% isopropanol/hexane.

To a stirred solution of 12 (10 mg) in THF (3.5 mL), was added dropwise a 1 M solution of TBAF in THF (105 μL, 105 μmol) followed by addition of activated molecular sieves 4A (ca. 100 mg). After 2 hours, the reaction mixture was purified on silica gel Sep-Pack cartridge (5-15% isopropanol/hexane) to give 3 mg of crude 13 that was purified on HPLC (Zorbax-Sil column, 250×10 mm, 13% isopropanol/hexane, 4 mL/min., R$_f$=7.42 min.) to give 2.5 mg (4.9 μmol, 46% yield from 10) of 13. UV (EtOH) λ$_{max}$=243, 251, 261 nm; ε$_{max}$=42,000; $^1$H NMR (500 MHz, CDCl$_3$) δ 0.56 (3H, s), 0.94 (3H, t, J=7.4 Hz), 1.04 (3H, d, J=6.6 Hz), 2.27-2.35 (2H, m), 2.57 (1H, dd, J=13.5 Hz, J=3.6 Hz), 2.83 (2H, m), 3.17 (1H, d, J=7.3 Hz), 3.96 (1H, t, J=6.8 Hz), 4.09 (2H, t, J=6.6 Hz), 4.44-4.53 (2H, m), 5.09 (1H, s), 5.11 (1H, s), 5.43 (1H, dd, J=15.4 Hz, J=6.6 Hz), 5.51 (1H, dd, J=15.4 Hz, J=8.4 Hz), 5.87 (1H, d, J=11.2 Hz), 6.35 (1H, d, J=11.2 Hz); MS (EI) 512 (M$^+$, 43), 494 (11), 476 (2), 409 (10), 285 (32), 251 (42), 208 (57), 135 (100); exact mass (ESI) calculated for C$_{32}$H$_{48}$O$_5$Na ([M+Na]$^+$) 535.3399, found 535.3399.

(22E)-(24R)-24-Butoxy-25-carbobutoxy-2-methylene-26,27-cyclo-22-dehydro-1α-hydroxy-19-norvitamin D$_3$ (14)

To a stirred solution of crude 12 (18 mg) in anhydrous n-butanol (1 mL), was added (1S)-(+)-10-camphorsulfonic acid (10 mg, 43 mmol) at 0° C. The reaction mixture was then warmed to room temperature and stirred for 3 days. A saturated aqueous solution of NaHCO$_3$ (1 mL) and water (2 mL) were then added, and the mixture was extracted with ethyl acetate (3×10 mL). The organic phase was dried over anhydrous MgSO$_4$, concentrated under reduced pressure, and the residue was purified on silica gel Sep-Pack cartridge (5-10% isopropanol/hexane) to give 9 mg of crude 14 that was purified on HPLC (Zorbax-Sil column, 250×10 mm, 10% isopropanol/hexane), 4 mL/min., R$_f$=6.52 min.) to give 8.5 mg (15 μmol, 77% yield from 10) of 14. UV (EtOH) λ$_{max}$=243, 251, 261 nm; ε$_{max}$=42,000; $^1$H NMR (400 MHz, CDCl$_3$) δ 0.56 (3H, s), 2.57 (1H, dd, J=13.3 Hz, J=3.5 Hz), 3.25-3.33 (1H, m), 3.42-3.49 (1H, m), 4.00-4.12 (2H, m), 4.23 (1H, dd, J=7.4 Hz, J=5.7 Hz), 4.48 (2H, m), 5.09 (1H, s), 5.11 (1H, s), 5.50 (1H, ddd, J=15.3 Hz, J=8.7 Hz, J=2.0 Hz), 5.88 (1H, d, J=11.2 Hz), 6.35 (1H, d, J=11.2 Hz); $^{13}$C NMR (100 MHz, CDCl$_3$) δ 10.7, 12.3, 12.5, 12.5, 13.8, 14.0, 19.2, 19.5, 20.8, 20.8, 22.3, 23.5, 27.8, 27.8, 28.9, 30.7, 31.9, 31.9, 38.2, 40.2, 40.3, 45.8, 56.0, 56.3, 64.4, 68.5, 68.6, 70.7, 71.8, 78.4, 78.5, 107.8, 115.4, 124.2, 124.9, 125.0, 130.6, 141.1, 141.3, 143.1, 152.0, 174.1; MS (EI) m/z 568 (M$^+$, 14), 512 (2), 494 (9), 477 (2), 409 (5), 285 (19), 253 (100); exact mass calculated for C$_{36}$H$_{56}$O$_5$Na ([M+Na]$^+$) 591.4025, found 591.4043.

1-Acetyl-cyclopropanecarboxylic acid n-butyl ester (15)

A mixture of acetoacetic acid n-butyl ester (8.1 mL, 7.9 g, 50 mmol), 1,2-dibromoethane (6.5 mL, 14.2 g, 75 mmol) and anhydrous potassium carbonate (20.0 g, 150 mmol) in acetone (50 mL) was stirred and refluxed for 20 hours. The mixture was filtered, and the filtrate was concentrated in vacuo. The residue was distilled under reduced pressure (oil pump) collecting fraction of 15 (6.92 g; 37.6 mmol; 75%) at 54-61° C. $^1$H NMR (400 MHz, CDCl$_3$) δ 0.95 (3H, t, J=7.4 Hz), 1.39 (2H, m), 1.47 (3H, s), 1.64 (2H, m), 2.47 (3H, s), 4.15 (2H, d, J=6.7 Hz); $^{13}$H NMR (100 MHz, CDCl$_3$) δ 13.6, 19.2, 29.9, 30.5, 35.1, 65.1, 171.1, 203.1; MS (EI) m/z 184 (M$^+$, 4), 169 (7), 128 (39), 111 (100); exact mass (ESI) calculated for C$_{10}$H$_{16}$O$_3$Na ([M+Na]$^+$) 207.0997, found 207.1007.

1-(2-Bromo-acetyl)-cyclopropanecarboxylic acid n-butyl ester (16)

To a stirred solution of 15 (3.30 g, 17.9 mmol) in methylene chloride (150 mL) and triethylamine (5.01 mL, 3.61 g, 35.7 mmol), was added dropwise triethylsilyl trifluoromethanesulphonate (4.07 mL, 4.72 g 17.9 mmol) at 0° C. After 20 minutes, N-bromosuccinimide (3.53 g, 19.8 mmol) was added, and the cooling bath was removed. Water (50 mL) was then added, and the mixture was extracted with methylene chloride (3×100 mL). The organic phase was dried over anhydrous MgSO$_4$, concentrated under reduced pressure, and the residue was purified by column chromatography (3-10% ethyl acetate/hexane) to give 3.42 g (13.0 mmol; 73% yield) of 16. $^1$H NMR MHz, CDCl$_3$) δ 0.96 (3H, t, J=7.4 Hz), 1.47

(2H, m), 1.60-1.66 (6H, m), 4.16 (2H, t, J=6.7 Hz), 4.50 (2H, s). $^{13}$C NMR (100 MHz, CDCl$_3$) δ 13.7, 19.2, 21.2, 30.5, 33.2, 35.1, 65.5, 170.4, 197.6. MS (EI) m/z 264 (40, M$^+$), 262 (39, M$^+$), 208 (20), 206 (20), 190 (56), 188 (54), 183 (71), 169 (100); exact mass (ESI) calculated for C$_{10}$H$_{15}$O$_3$BrNa ([M+Na]$^+$) 285.0102, found 285.0114.

1-[2-(Dimethoxy-phosphoryl)-acetyl]-cyclopropan-ecarboxylic acid n-butyl ester (17)

A solution of 16 3.42 g (13.0 mmol) and trimethylphosphite (1.95 mL, 2.05 g, 16.5 mmol) in toluene (45 mL) was refluxed for 15 hours. The solvent and remaining trimethyl phosphite were then distilled off, and the residue was purified by column chromatography (2-10% isopropanol/hexane) to give 2.26 g (7.74 mmol; 59% yield) of 17. $^1$H NMR (500 MHz, CDCl$_3$) δ 0.95 (3H, t, J=7.3 Hz), 1.39 (2H, m), 1.57-1.67 (6H, m), 3.75 (2H, d, J$_{H\text{-}P}$=22.1 Hz), 3.78 (6H, d, J$_{H\text{-}P}$=11.1 Hz), 4.15 (2H, t, J=6.7 Hz). $^{13}$C NMR (125 MHz, CDCl$_3$) δ 13.7, 19.2, 20.6, 30.5, 35.3, 39.8, 40.8, 52.9 (d, J$_{C\text{-}P}$=6.0 Hz), 170.8, 197.0 (d, J$_{C\text{-}P}$=6.3 Hz). MS (EI) m/z 292 (15, M$^+$), 264 (17), 236 (21), 218 ((45), 191 (18), 163 (22), 150 (59), 126 (100); exact mass (ESI) calculated for C$_{12}$H$_{21}$O$_6$PNa ([M+Na]$^+$) 315.0973, found 315.0963.

Scheme XIII

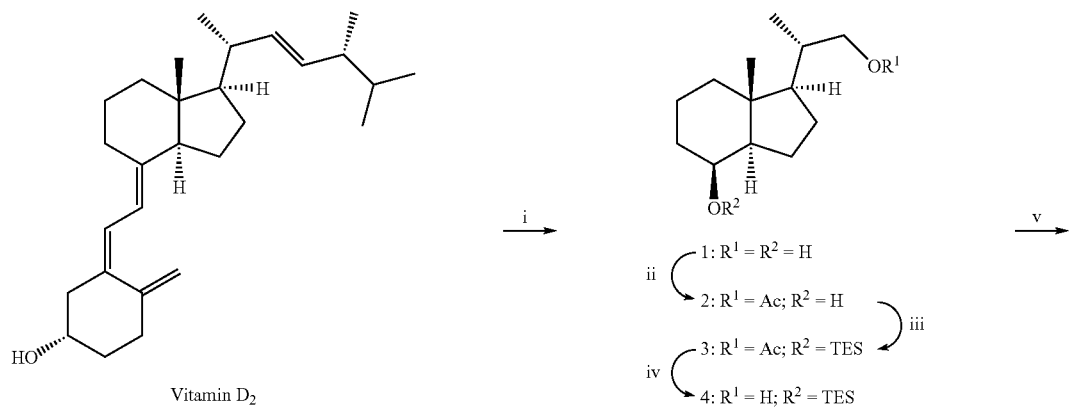

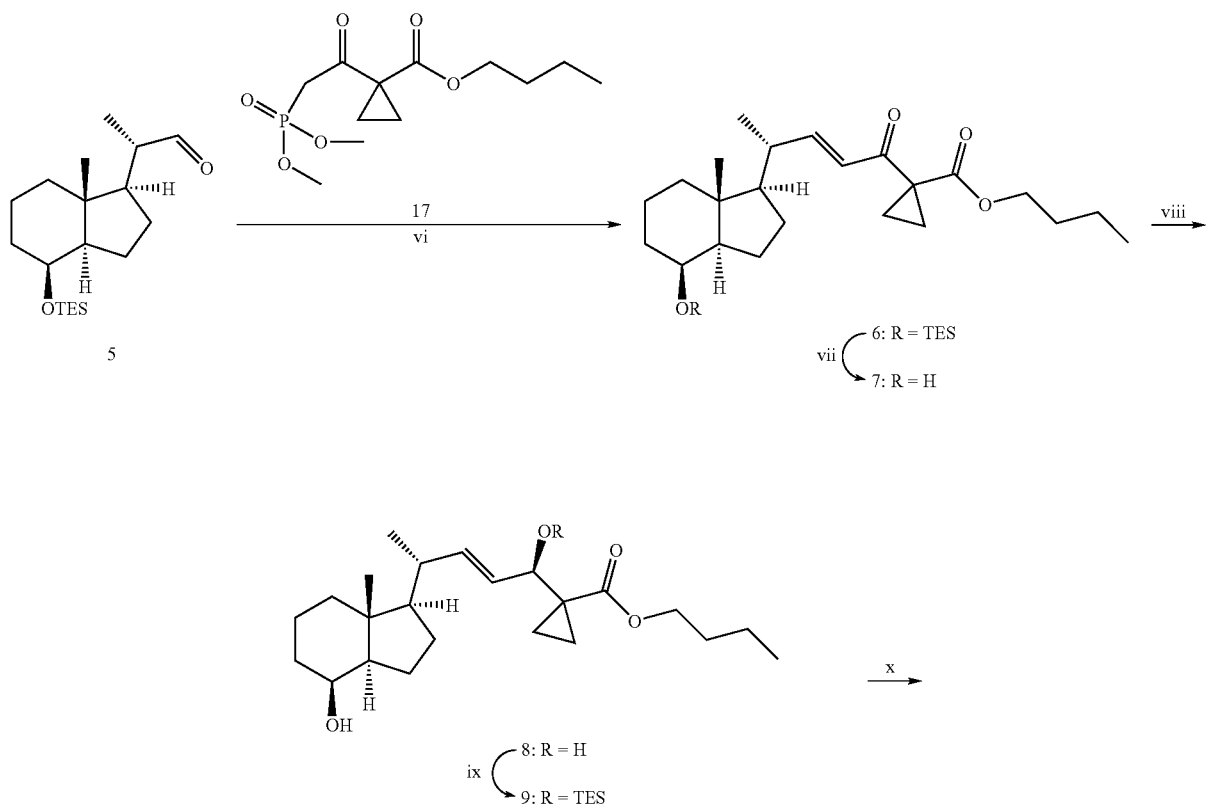

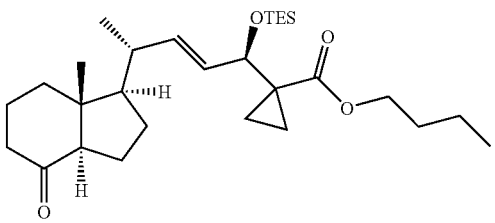

10

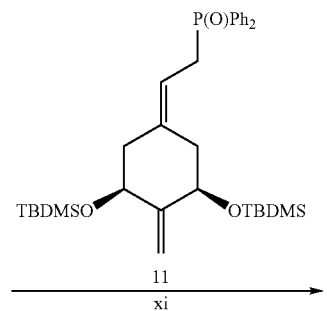

11

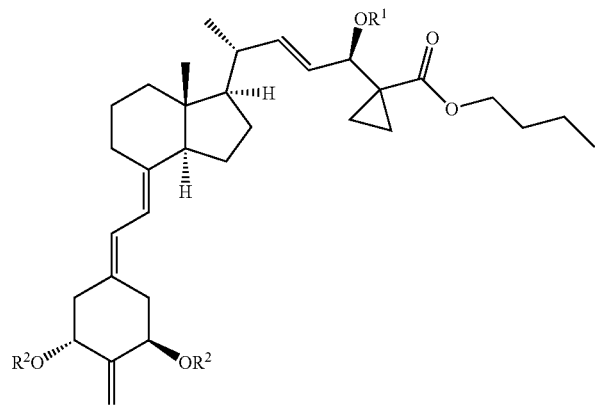

12: $R^1$ = TES, $R^2$ = TBS xii → 13: $R^1 = R^2$ = H xiii → 14: $R^1$ = n-Bu; $R^2$ = H (i) $O_3$, MeOH, py; $NaBH_4$, 76%. (ii) $Ac_2O$, $Et_3N$, DMAP, $CH_2Cl_2$, 97%. (iii) TESOTf, 2,6-lutidine, $CH_2Cl_2$.
(iv) MeONa/MeOH, 97% from 2. (v) $SO_3$/py, DMSO, $Et_3N$, $CH_2Cl_2$, 78%. (vi) 17, LiHMDS, THF, 89%.
(vii) CSA, n-BuOH, 96%. (viii) $NaBH_4$, $CeCl_3 \times 7H_2O$, EtOH/THF, 23%. (ix) TESCl, $Et_3N$, $CH_2Cl_2$, 52%.
(x) PDC, PPTS, $CH_2Cl_2$, 81%. (xi) 11, PhLi, THF. (xii) TBAF, molecular sieves 4 A, THF, 46% from 10.
(xiii) CSA, n-BuOH, 77% from 10.

Scheme XIV

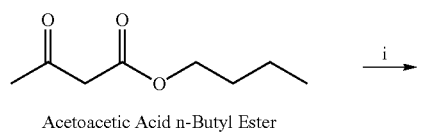

Acetoacetic Acid n-Butyl Ester i →

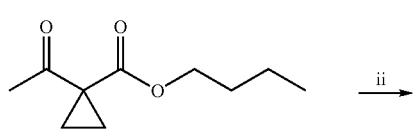

15 ii →

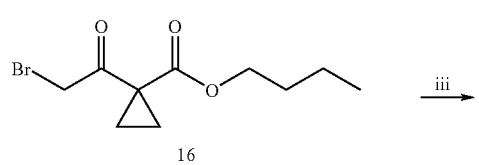

16 iii →

-continued

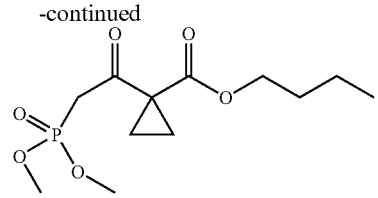

17

(i) $BrCH_2CH_2Br$, $K_2CO_3$, acetone, 75%. (ii) TESOTf, $Et_3N$, $CH_2Cl_2$; NBS, 73%.
(iii) $P(OMe)_3$, PhMe, 59%.

Synthesis of (22E)-(20S)-25-heptanoyl-2α-methyl-24-oxo-22-dehydro-1α-hydroxy-19-norvitamin $D_3$ (X)

Compound X is prepared using the same procedure used to prepare compound XII except that 20-epi compound 18 of Scheme IXA is reduced with $H_2$ in the presence of $(Ph_3P)_3RhCl$ and is then deprotected to afford the title compound.

Synthesis of (22E)-25-heptanoyl-2α-methyl-24-oxo-22-dehydro-1α-hydroxy-19-norvitamin $D_3$ (XI)

Compound XI is prepared using the same procedure used to prepare compound XIII except that compound 18 of Scheme IXA is reduced with $H_2$ in the presence of $(Ph_3P)_3RhCl$ and is then deprotected to afford the title compound.

Synthesis of (22E)-(20S)-25-heptanoyl-2-methylene-24-oxo-22-dehydro-1α-hydroxy-19-norvitamin $D_3$ (XII)

Compound XII is prepared using the synthetic route depicted in Scheme IXA using the phosphonate prepared as shown in Scheme IXB and compound 4 which is synthesized using the synthetic route shown in Scheme VA with the modification that compound 1 of Scheme VA is epimerized by reaction with tetrabutylammonium hydroxide using a procedure similar to that shown in Scheme I and Scheme II. After silyl group removal, the diastereomers are separated by chromatography, and the 20-epi compound 1 is used in place of compound 1 in Scheme VA.

Synthesis of (22E)-(20S)-25-heptanoyl-2-methylene-24-oxo-22-dehydro-1α-hydroxy-19-norvitamin $D_3$ (XIII)

Compound XIII is prepared using the synthetic route depicted in Scheme IXA using the phosphonate prepared as shown in Scheme IXB and compound 4 which is synthesized using the synthetic route shown in Scheme VA.

Synthesis of (22E)-(20S)-25-heptanoyl-2α-methyl-24-oxo-22-dehydro-1α-hydroxyvitamin $D_3$ (XV)

Compound XV is prepared using the synthetic route depicted in Scheme XII for the synthesis of compound XVI with the modification that 20-epi compound 2 (see Schemes I and VA) is used in place of compound 2 in Scheme XII.

Synthesis of (22E)-25-heptanoyl-2α-methyl-24-oxo-22-dehydro-1α-hydroxyvitamin $D_3$ (XVI)

Compound XVI is prepared using the synthetic route depicted in Scheme XII using compound 2 prepared as shown in Scheme VA and the phosphonate prepared as shown in Scheme IXB.

Synthesis of (22E)-(20S,24R)-25-hexanoyl-2α-methyl-26,27-cyclo-22-dehydro-1α,24-dihydroxyvitamin $D_3$ (XVII)

Compound XVII is prepared using the synthetic routes depicted in Schemes X and XI with the modification that compound D of Scheme X is epimerized by reaction with tetrabutylammonium hydroxide using the procedure shown in Scheme I. The diastereomers are separated by chromatography, and the 20-epi compound D (E) is used in place of compound D in Schemes X and XI.

Synthesis of (22E)-(24R)-25-hexanoyl-2α-methyl-26,27-cyclo-22-dehydro-1α,24-dihydroxyvitamin $D_3$ (XVIII)

Compound XVIII is prepared using the synthetic schemes shown in Schemes X and XI.

Biological Activity of Vitamin D Analogs

Each of the compounds of the invention is or was tested using the assay methodologies described below and exhibits or exhibited affinity for the vitamin D receptor and antagonist activity to inhibit HL-60 cell differentiation induced by the natural hormone 1α,25-dihydroxyvitamin $D_3$.

When any of the above listed compounds is prepared with appropriate physical data to support the structure, the following tests are applied.

Vitamin D Receptor Binding Assays
  Protein Source
    Full-length recombinant rat receptor is/was expressed in *E. coli* BL21(DE3) Codon Plus RIL cells and purified to homogeneity using two different column chromatography systems. The first system is/was a nickel affinity resin that utilizes the C-terminal histidine tag on this protein. The protein that is/was eluted from this resin is/was further purified using ion exchange chromatography (S-Sepharose Fast Flow). Aliquots of the purified protein are/were quick frozen in liquid nitrogen and stored at −80° C. until use. For use in binding assays, the protein is/was diluted in $TEDK_{50}$ (50 mM Tris, 1.5 mM EDTA, pH 7.4, 5 mM DTT, 150 mM KCl) with 0.1% Chaps detergent. The receptor protein and ligan concentration is/was optimized such that no more than 20% of the added radiolabeled ligand is/was bound to the receptor.
  Study Drugs
    Unlabeled ligands are/were dissolved in ethanol and the concentrations determined using UV spectrophotometry $(1,25(OH)_2D_3$: molar extinction coefficient=18,200 and $\lambda_{max}$=265 nm; Analogs: molar extinction coefficient=42,000 and $\lambda_{max}$=252 nm). Radiolabeled ligand (3H-1,25(OH)$_2D_3$, ~159 Ci/mmole) was added in ethanol at a final concentration of 1 nM.
  Assay Conditions
    Radiolabeled and unlabeled ligands are/were added to 100 mcl of the diluted protein at a final ethanol concentration of ≦10%, mixed and incubated overnight on ice to reach binding equilibrium. The following day, 100 mcl of hydroxylapatite slurry (50%) is/was added to each tube and mixed at 10-minute intervals for 30 minutes. The hydroxylapaptite is/was collected by centrifugation and then washed three times with Tris-EDTA buffer (50 mM Tris, 1.5 mM EDTA, pH 7.4) containing 0.5% Titron X-100. After the final wash, the pellets was/were transferred to scintillation vials containing 4 mL of Biosafe II scintillation cocktail, mixed and placed in a scintillation counter. Total binding is/was determined from the tubes containing only radiolabeled ligand.

HL-60 Cellular Differentiation Tests
  Solution Preparation
    The compounds of the invention are/were dissolved in ethanol and the concentrations are/were determined using UV spectrophotometry. Serial dilutions are/were prepared so that a range of drug concentrations can be tested without changing the final concentration of ethanol (≦0.2%) present in the cell cultures.
    Antagonism is/was tested by adding a combination of 1,25 (OH)$_2D_3$ and the putative antagonist in the same well keeping the final ethanol concentration the same.
  Cells
    Human promyelocytic leukemia (HL60) cells are/were grown in RPMI-1640 medium containing 10% fetal bovine serum. The cells are/were incubated at 37° C. in the presence of 5% $CO_2$.
  Assay Conditions
    HL60 cells are/were plated at 1.2×10$^5$ cells/mL. Eighteen hours after plating, cells in duplicate are/were treated with compound of the invention in ethanol. Four days post-dose, the cells are/were harvested and a nitro blue tetrazolium reduction assay is/was performed (Collins et al., *J. Exp. Med.* 149, 969-974, Appendix A (1979)). The percentage of differentiated cells is/was determined by counting a total of 200 cells and recording the number that contained intracellular black-blue formazan deposits. Verification of differentiation to monocytic cells is/was determined by measuring phagocytic activity. All drug concentrations are/were tested in duplicate.

Reporter Gene Assay

A reporter gene assay is/was used in which the promoter to the vitamin D 24-hydroxylase, i.e. CYP24 is/was placed in front of a luciferase reporter and is/was permanently transfected into ROS-17/2.8 osteoblast cell cultures as previously described (see Arbour, N. C., T. K. Ross, C. Zierold, J. M. Prahl, and H. F. DeLuca. A Highly Sensitive Method for Large-Scale Measurements of 1,25-Dihydroxyvitamin D. *Analyt. Biochem.* 255, 148-154, (1998) which is hereby incorporated by reference in its entirety and for all purposes as if fully set forth herein). These cells are/were grown to almost confluency at which time the analog or the standard 1α,25-(OH)$_2$D$_3$ is/was added. After 4 hours of incubation, the cells are/were ruptured and luciferase is/was measured by the methods provided by the Promega Kit. These experiments show the level of activity of the vitamin D analogs of the invention at transcription. The ideal inhibitor is/was relatively inactive in transcription, but is/was very active in binding to the soluble receptor.

Antagonism is/was tested by adding a combination of 1,25 (OH)$_2$D$_3$ and the putative antagonist in the same well keeping the ethanol concentration the same.

The phrase "RLU" refers to relative luciferase units.

Competition for Transcription Activity

The third test that is performed is competition for transcription activity. Again, the ROS-17/2.8 osteoblast cells that contain the reporter gene system described above are employed. A dose-response curve is constructed with 1α,25-(OH)$_2$D$_3$ and another 1α,25-(OH)$_2$D$_3$ dose response curve is prepared with increasing concentrations of antagonist or analogs of the invention. Analogs that prevent 1α,25-(OH)$_2$D$_3$-induced transcription, are defined using this technique as either weak agonist or a complete antagonist of the VDR for 1α,25-(OH)$_2$D$_3$.

Intestinal Calcium Transport and Bone Calcium Mobilization

Male, weanling Sprague-Dawley rats are/were placed on Diet 11 (0.47% Ca) diet +AEK for one week followed by Diet 11 (0.02% Ca) +AEK for 3 weeks. The rats are/were then switched to a diet containing 0.47% Ca for one week followed by two weeks on a diet containing 0.02% Ca. Dose administration began during the last week on 0.02% calcium diet. Four consecutive ip doses are/were given approximately 24 hours apart. Twenty-four hours after the last dose, blood is/was collected from the severed neck, and the concentration of serum calcium is/was determined as a measure of bone calcium mobilization. The first 10 cm of the intestine is/was also collected for intestinal calcium transport analysis using the everted gut sac method.

Antagonism is/was tested by administering a combination of 1,25(OH)$_2$D$_3$ and the putative antagonist to the animal simultaneously.

Figure 2:
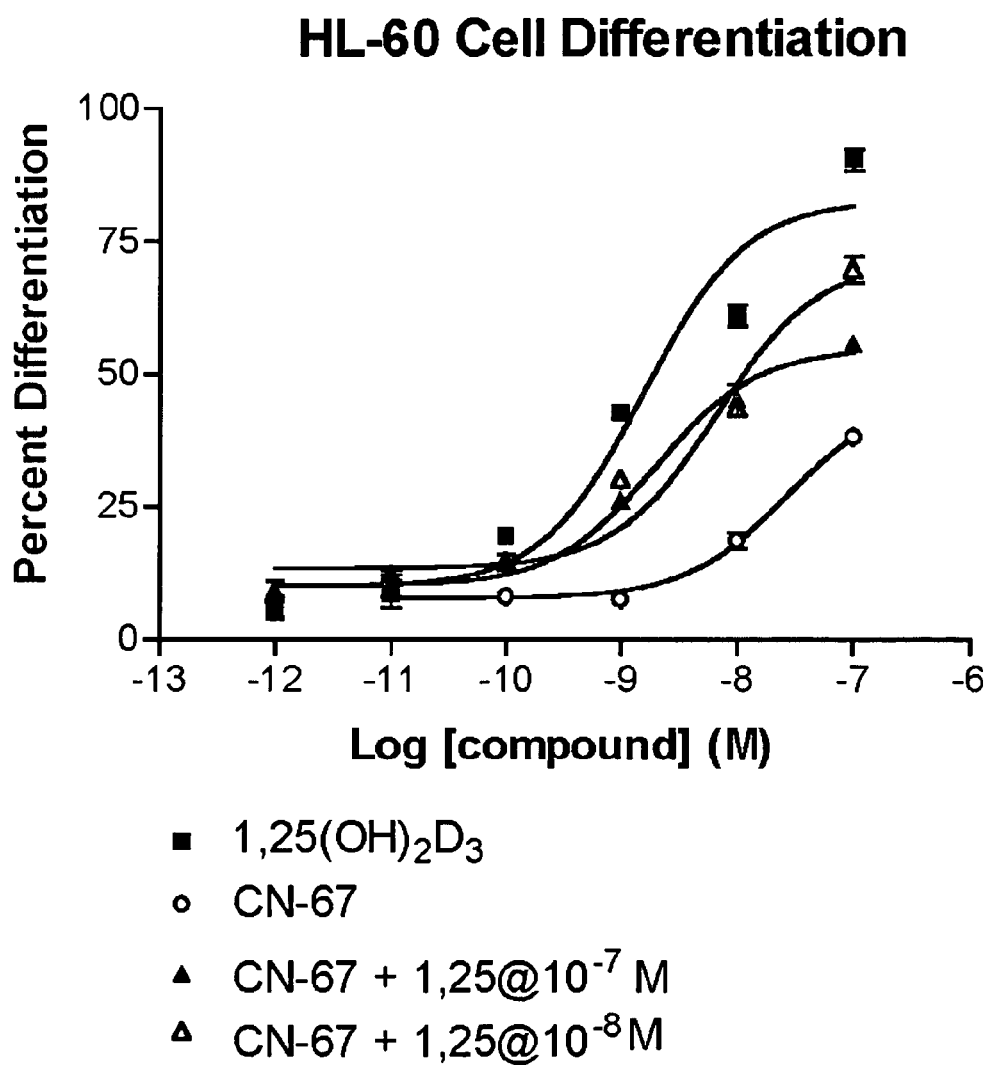
Figure 4:
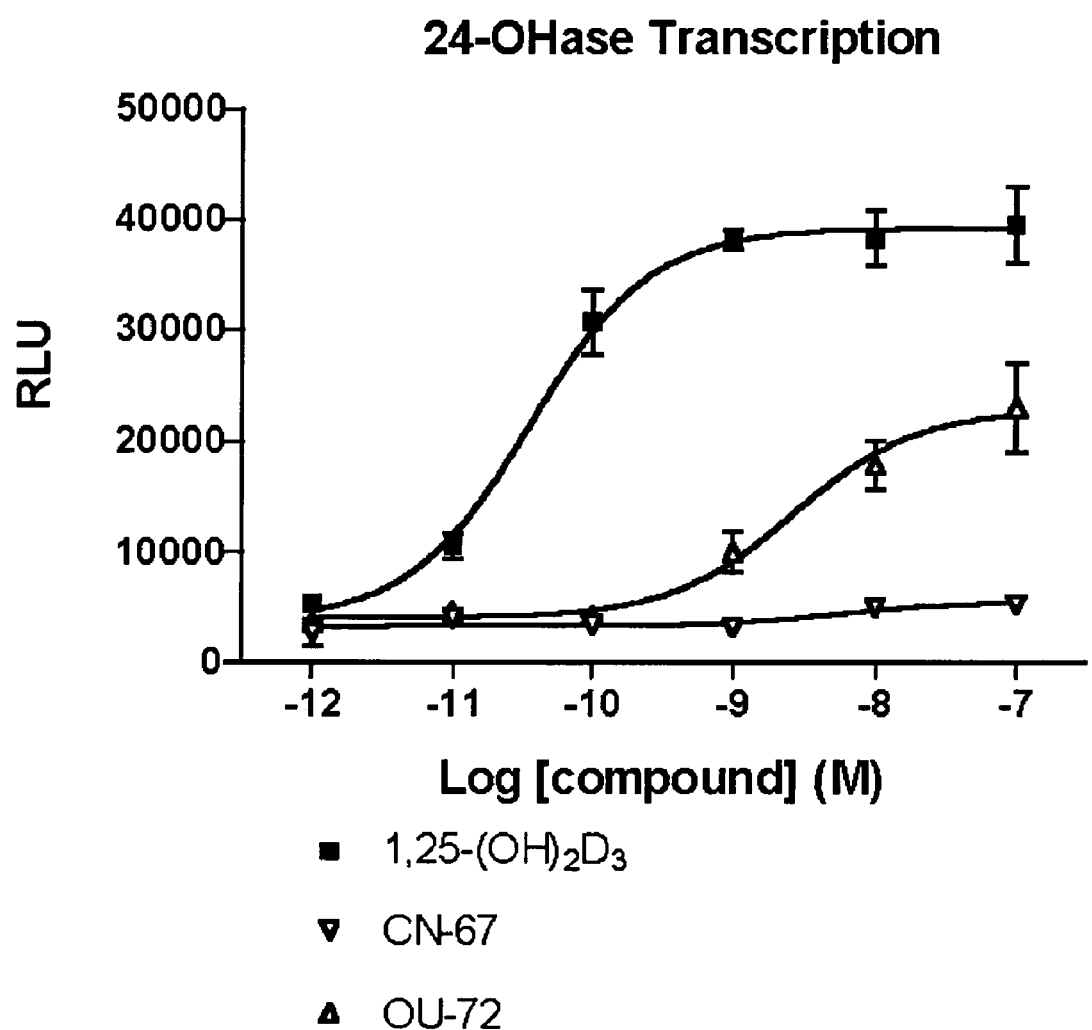
Figure 5:
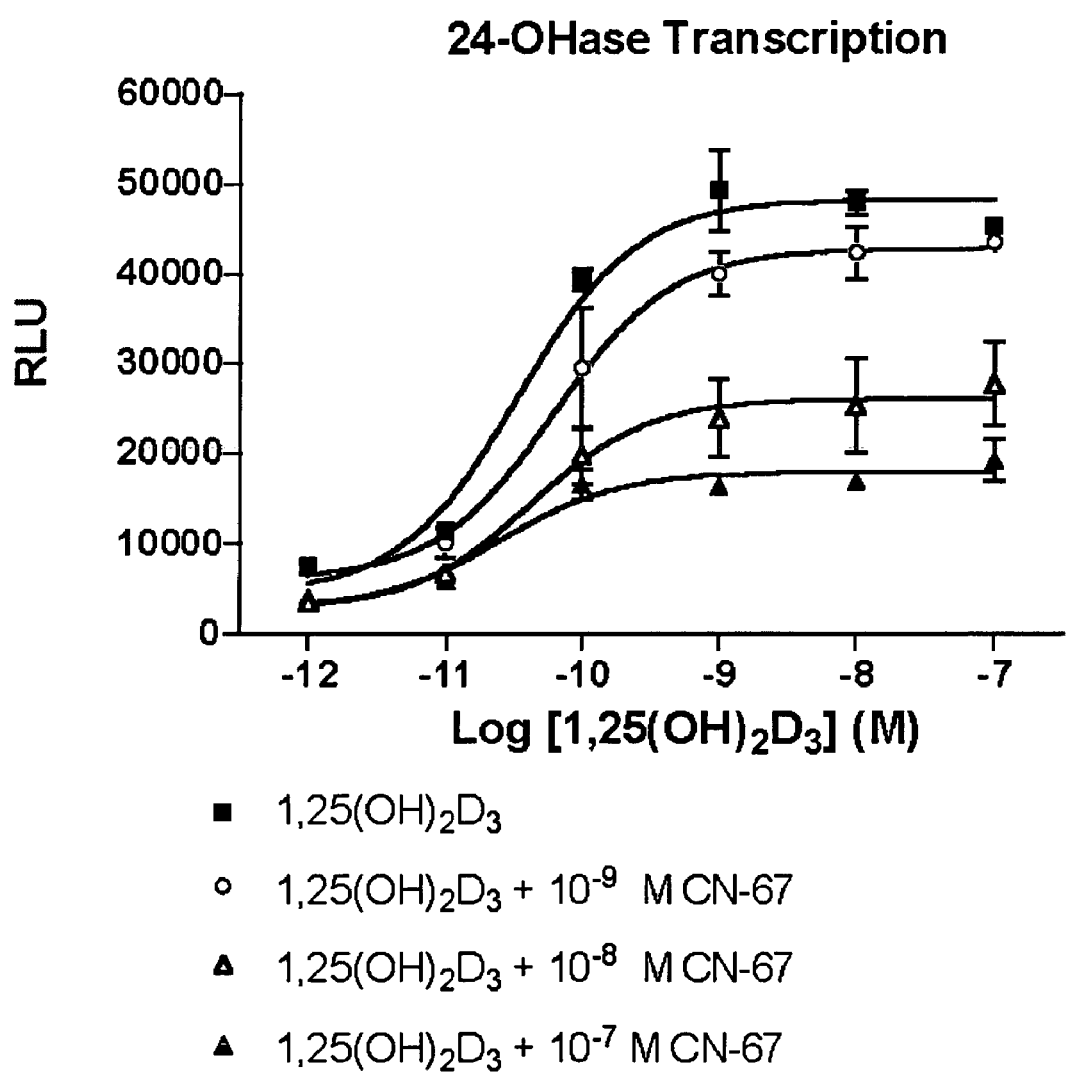

(22E)-(24R)-24-Butoxy-25-carbobutoxy-2-methylene-26,27-cyclo-22-dehydro-1α-hydroxy-19-norvitamin D$_3$ (CN-67) binds to the recombinant vitamin D receptor, but is significantly less active than 1α,25-dihydroxyvitamin D$_3$ is in this respect (see FIG. 1). CN-67 is less active than 1α,25-dihydroxyvitamin D$_3$ in inducing differentiation of HL-60 cells (see FIG. 2). CN-67 does not appear to be active in causing transcription, as shown in FIG. 4. However, as shown in FIG. 5, CN-67 appears to exhibit antagonistic activity when administered along with the native hormone (1α,25-dihydroxyvitamin D$_3$). This compound will find use as an effective therapy for treating asthma, hypercalcemia, eczema, hyperparathyroidism, sarcoidosis, and vitamin D intoxication.

Figure 3:
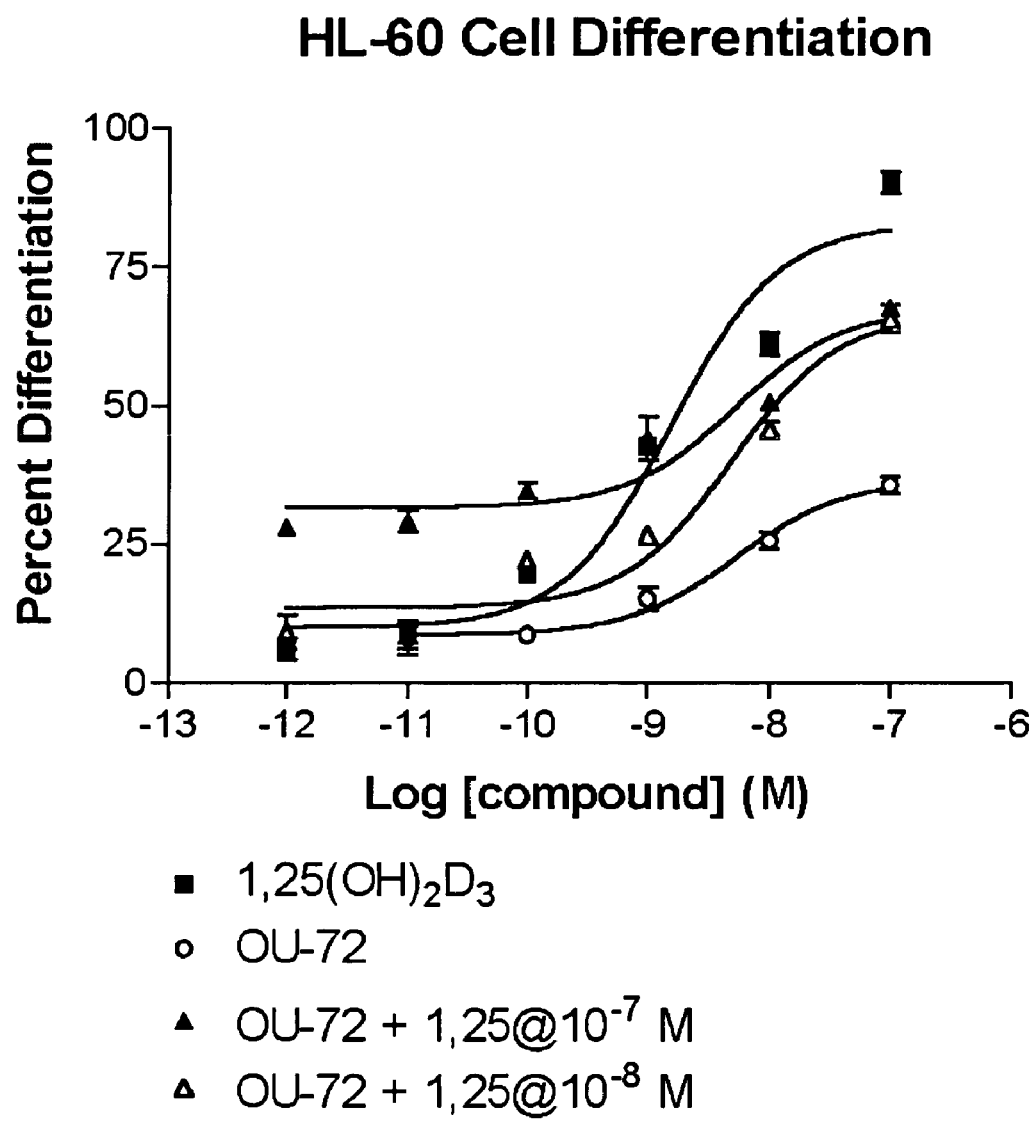
Figure 6:
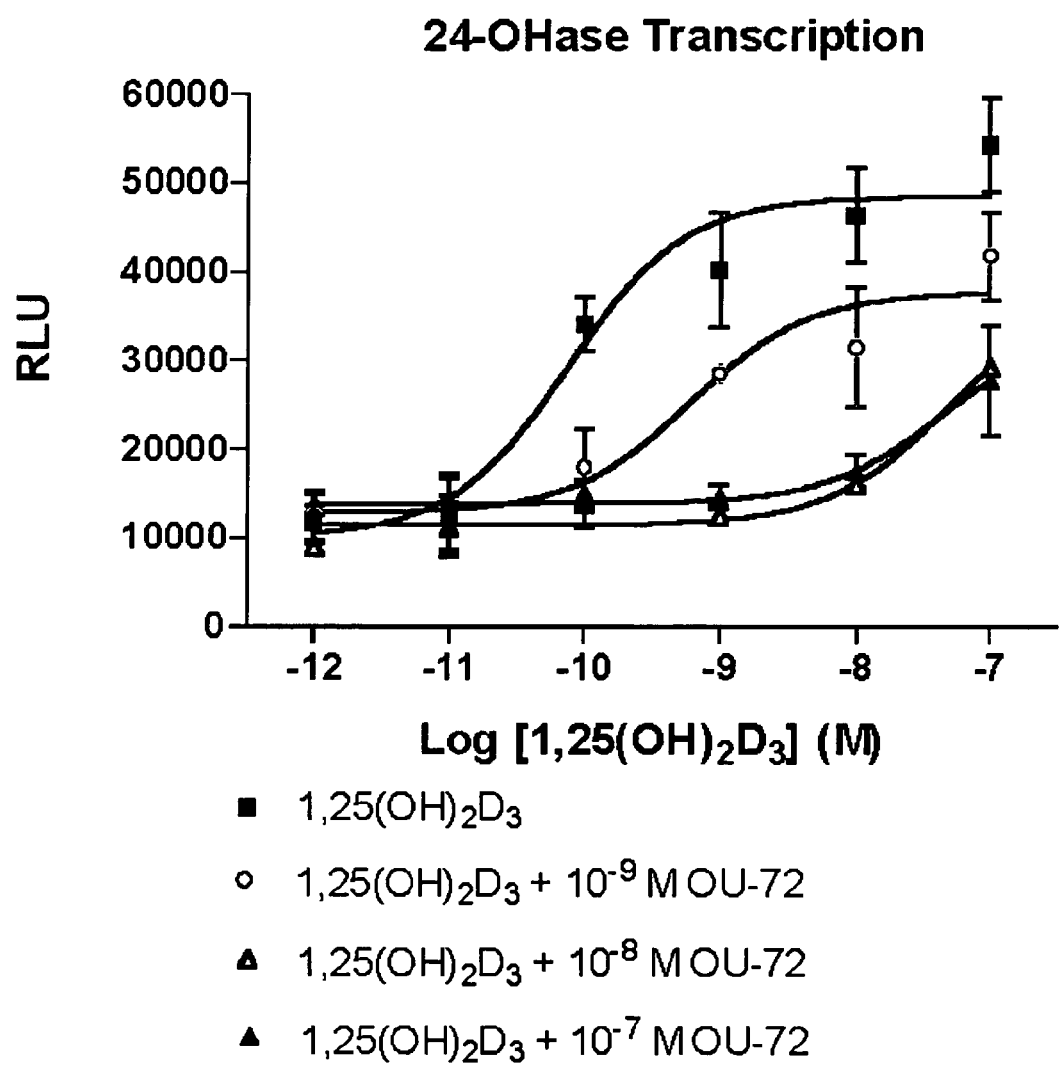
Figure 7:
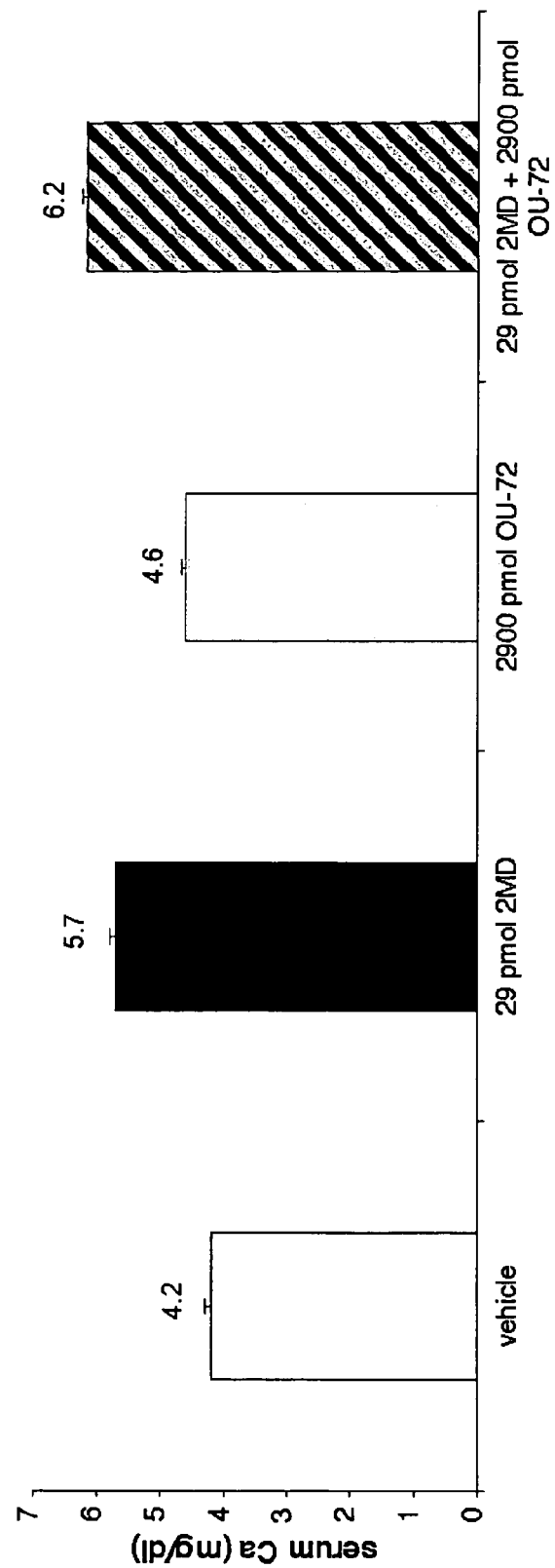
Figure 8:
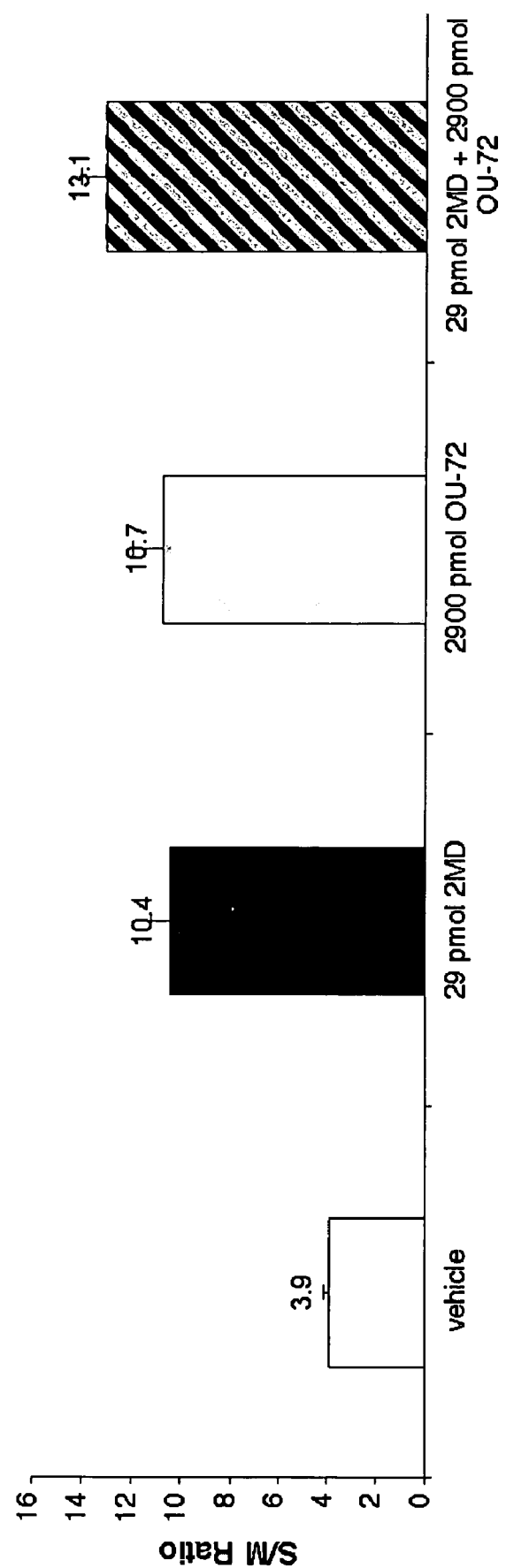

(22E)-(24R)-25-Carbobutoxy-2-methylene-26,27-cyclo-22-dehydro-1α,24-dihydroxy-19-norvitamin D$_3$ (OU-72) is approximately equal to the native hormone in binding to the vitamin D receptor as shown in FIG. 1. OU-72 is active in stimulating transcription of a reporter gene stably transfected in Ros17/2.8 (bone) cells, indicating significant biological activity (see FIG. 4). Furthermore, OU-72 shows antagonistic activity when administered along with the native hormone (1α,25-dihydroxyvitamin D$_3$) as shown in FIG. 6. OU-72 is less active than 1α,25-dihydroxyvitamin D$_3$ in inducing differentiation of HL-60 cells (see FIG. 3). OU-72 has no calcemic activity when measured either by bone calcium mobilization even when given at the dose of 2,900 pmol/day (see FIG. 7). However, OU-72 does retain does retain the ability to elevate intestinal calcium transport (FIG. 5) (see FIG. 8). This compound will find use as an effective therapy for treating asthma, hypercalcemia, eczema, hyperparathyroidism, sarcoidosis, and vitamin D intoxication.

Asthma Model

The fourth test performed on the analogs is treatment using an asthma model. For this test, BALBc mice are injected for 7 days with 10 micrograms of ovalbumin together with alum to sensitize the animals. These are given by intraperitoneal injection and at the end of 7 days, the asthmatic reaction to an inhaled dose of ovalbumin is examined. In this test, the ovalbumin as a 0.2% solution is delivered by nebulizer to the mouse. Air flow measures are carried out as described by Isenberg-Feig et al. in *Current Allergy and Asthma Reports,* 3:70-78 (2003) which is hereby incorporated by reference in its entirety and for all purposes as if fully set forth herein. Furthermore, the lungs are removed and sectioned for analysis. The degree of invasion of eosinophils into the bronchial tissue is used as a non-subjective measurement of asthmatic response. After the animals are sensitized and given the expected responses to ovalbumin, the animals are subjected to an aerosol that includes either a vitamin D antagonist of the invention or 1α,25-(OH)$_2$D$_3$. After exposure to the vitamin D antagonist of the invention or the 1α,25-(OH)$_2$D$_3$, the animals will be exposed to a nebulized dose of 0.2% ovalbumin. The presence of the antagonist will be found to block the asthmatic response to the inhaled ovalbumin. Preliminary work indicates that 1α,25-(OH)$_2$D$_3$ actually increases the severity of the asthmatic response to ovalbumin. Therefore, doses of 1α,25-(OH)$_2$D$_3$ sufficient to provide a very severe asthma reaction are given to animals in some tests, and then an analog of the invention is administered to antagonize it.

Finally, the ketone analogs of the invention are tested for their effectiveness systemically. They are also tested with respect to their ability to antagonize intestinal calcium transport and intestinal phosphate transport to 1α,25-(OH)$_2$D$_3$. These results show that the analogs of the invention show promise in treating asthma and antagonizing the vitamin D receptor.

The Effect of 1α,25-Dihydroxyvitamin D$_3$ on Ovalbumin-Inducted Allergic Asthma in Brown Norway Rats Data by Matheu et al. (J Allergy Clin Immunol 112:585, 2003) indicate that 1α,25-dihydroxyvitamin D$_3$ (1,25(OH)$_2$D$_3$) both triggers and exacerbates asthma symptoms in a mouse model of asthma. Moreover, Wittke et al. (J.

Immunol 173: 3432, 2004) demonstrated that vitamin D receptor knockout mice fail to develop ovalbumin (OVA)-induced allergic asthma.

Materials and Methods

Species, Diet and Justification 6-7 week old Brown Norway male rats were obtained from Harlan Sprague-Dawley (Madison, Wis.) and housed in shoebox cages. Animals were provided a purified rodent diet prepared in-house containing 0.47% calcium and 0.3% phosphorus, and water ad libitum. The diet was supplemented with 1.6 IU vitamin $D_3$/g.

Rats are the species of choice for the in vivo analysis of 1,25-$(OH)_2D_3$ and analogs as vitamin D metabolism is similar between rats and humans. OVA-sensitized Brown Norway rats have been used extensively as an animal model of asthma.

OVA Sensitization and Challenge Protocol

Rats were sensitized on Days 0 and 7 with a 1 mL intraperitoneal (I.P.) injection of 1 mg/mL OVA in phosphate-buffered saline (PBS) precipitated 1:1 with Imject Alum (PIERCE, IL). Control animals were sensitized with PBS. The animals were then challenged with aerosolized OVA [1% (w/v)] or aerosolized PBS (control) on Days 14 and 16. This OVA-sensitization and -challenge protocol has been used extensively to generate asthma symptoms in rats. Aerosolized-PBS (200 µL) or aerosolized-OVA (200 µL) was delivered by using the Microsprayer Syringe Model 1C (PennCentury, Philadelphia, Pa.).

Dose Administration and Regime

Aerosolized-vehicle [aqueous solution containing 30% (v/v) propylene glycol and 5% ethanol], or aerosolized-1,25 $(OH)_2D3$ (500 ng/Kg of body weight) was administered on Days 14 and 16. There were 4 groups in the study. Group 1: Sensitized and challenged with PBS, no treatment. Group 2: Sensitized and challenged with OVA, no treatment. Group 3: Sensitized and challenged with OVA, vehicle treatment on Days 14 and 16. Group 4: Sensitized and challenged with OVA, 1,25$(OH)_2D3$ treatment on Days 14 and 16.

End-of-Study Necropsy

At the end of the study, 17 days after the first I.P. injection, lungs were lavaged five times with 5 mL/each of calcium- and magnesium-free PBS containing 0.05 mM EDTA (ethylenediamine tetraacetic acid). The lavage fluid was centrifuged at 1,000×g for 10 minutes. The supernatant was removed, and the cell pellet was resuspended in 1 mL cold PBS. Total cell counts in bronchoalveolar lavage fluid (BALF) was performed using a hemocytometer. Slides of BALF were prepared by cytospin-2 cytocentrifugation of an aliquot of the cell suspension, and a differential cell count to determine the number of leukocytes was performed after staining with Diff-Quick (IMED, Inc., CA).

RESULTS AND DISCUSSION

Figure 9:
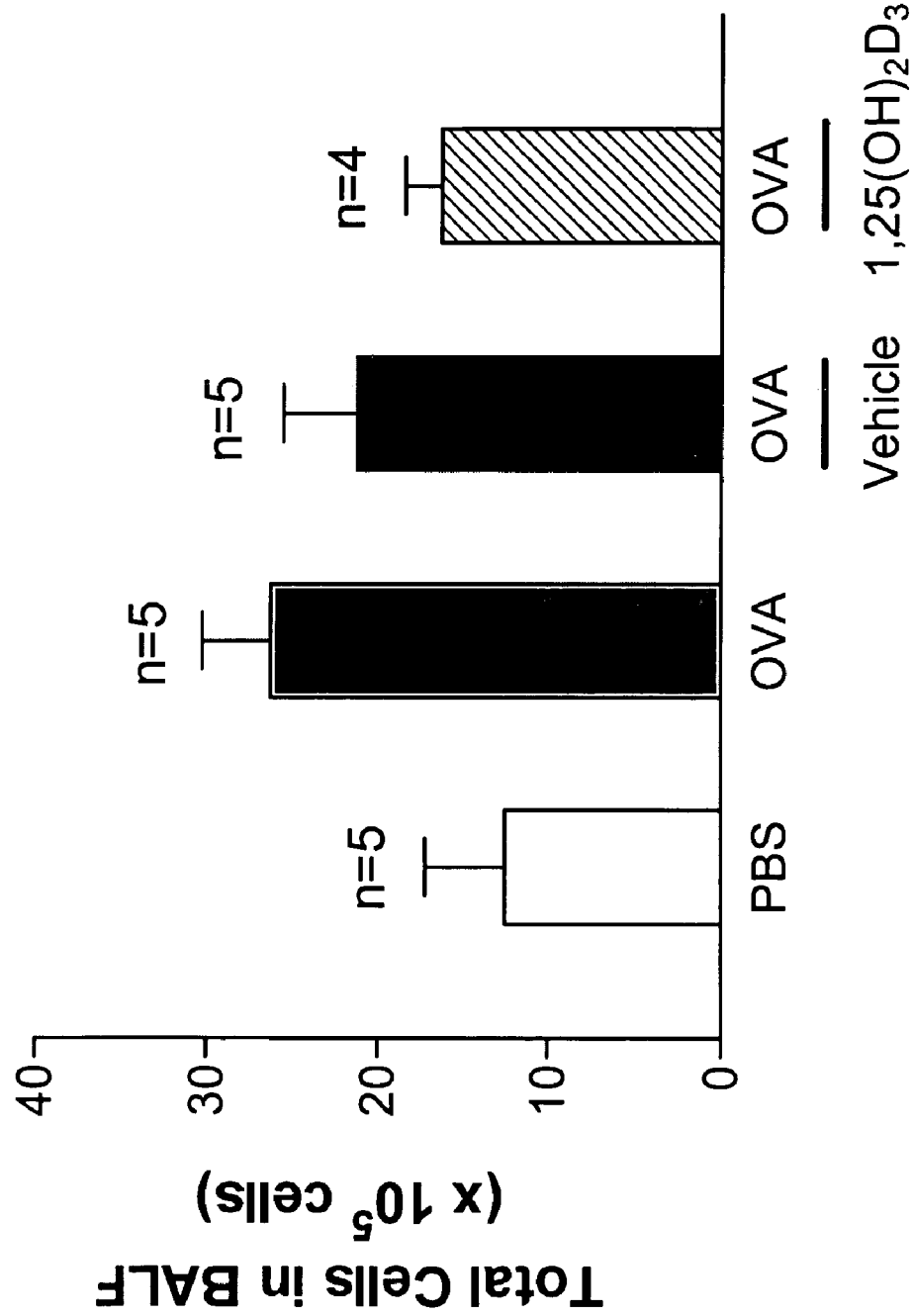
FIG. 9 is a bar graph of the total cell counts in BALF (bronchoalveolar lavage fluid) of Brown Norway rats after OVA-challenge. As shown, 1,25(OH)$_2$D$_3$ inhibits the OVA (ovalbumin)-mediated increase in total number of cells in BALF.
Figure 10:
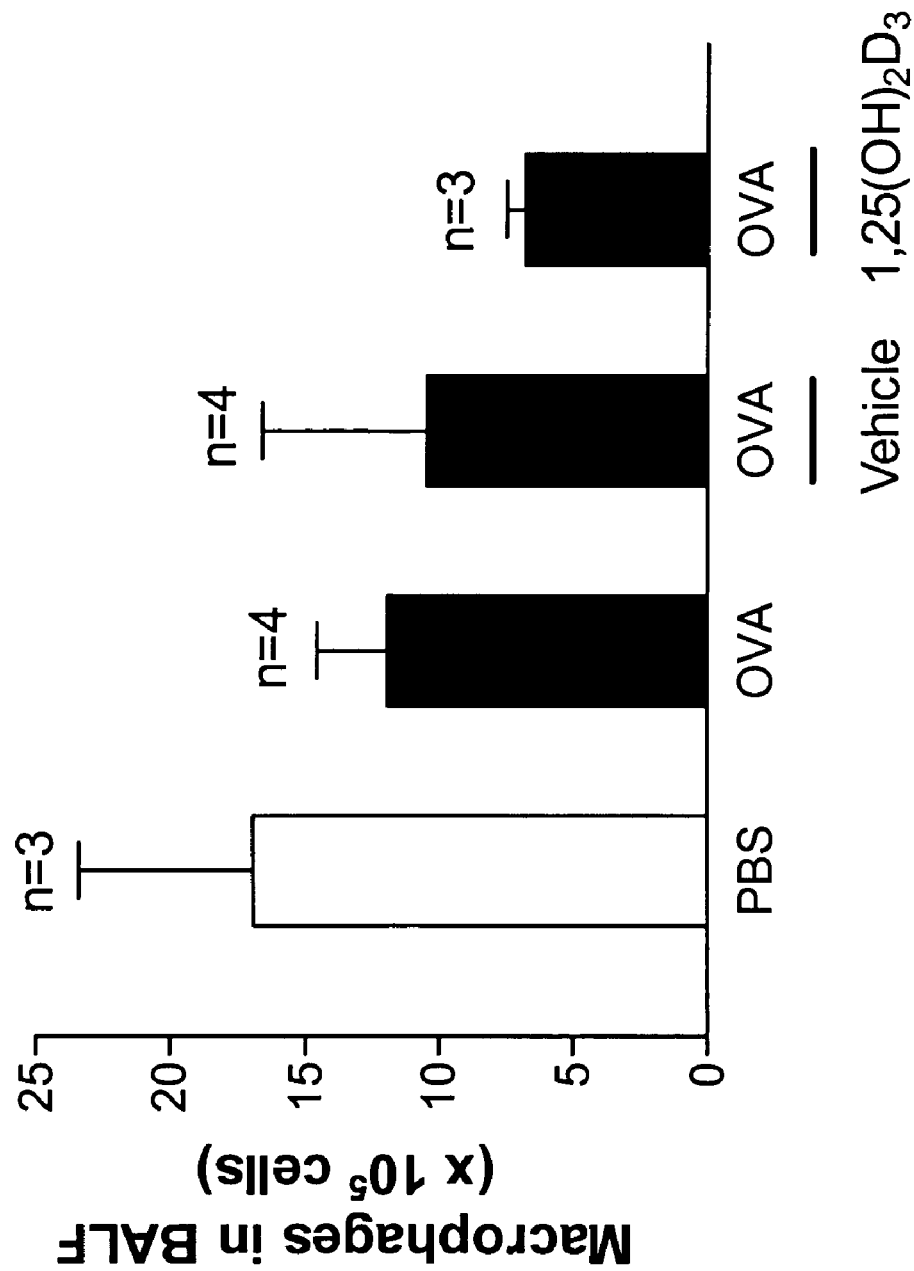
FIG. 10 is a bar graph of the number of macrophages in BALF of Brown Norway rats after OVA-challenge. As shown, 1,25(OH)$_2$D$_3$ decreases the number of macrophages compared to the control.
Figure 11:
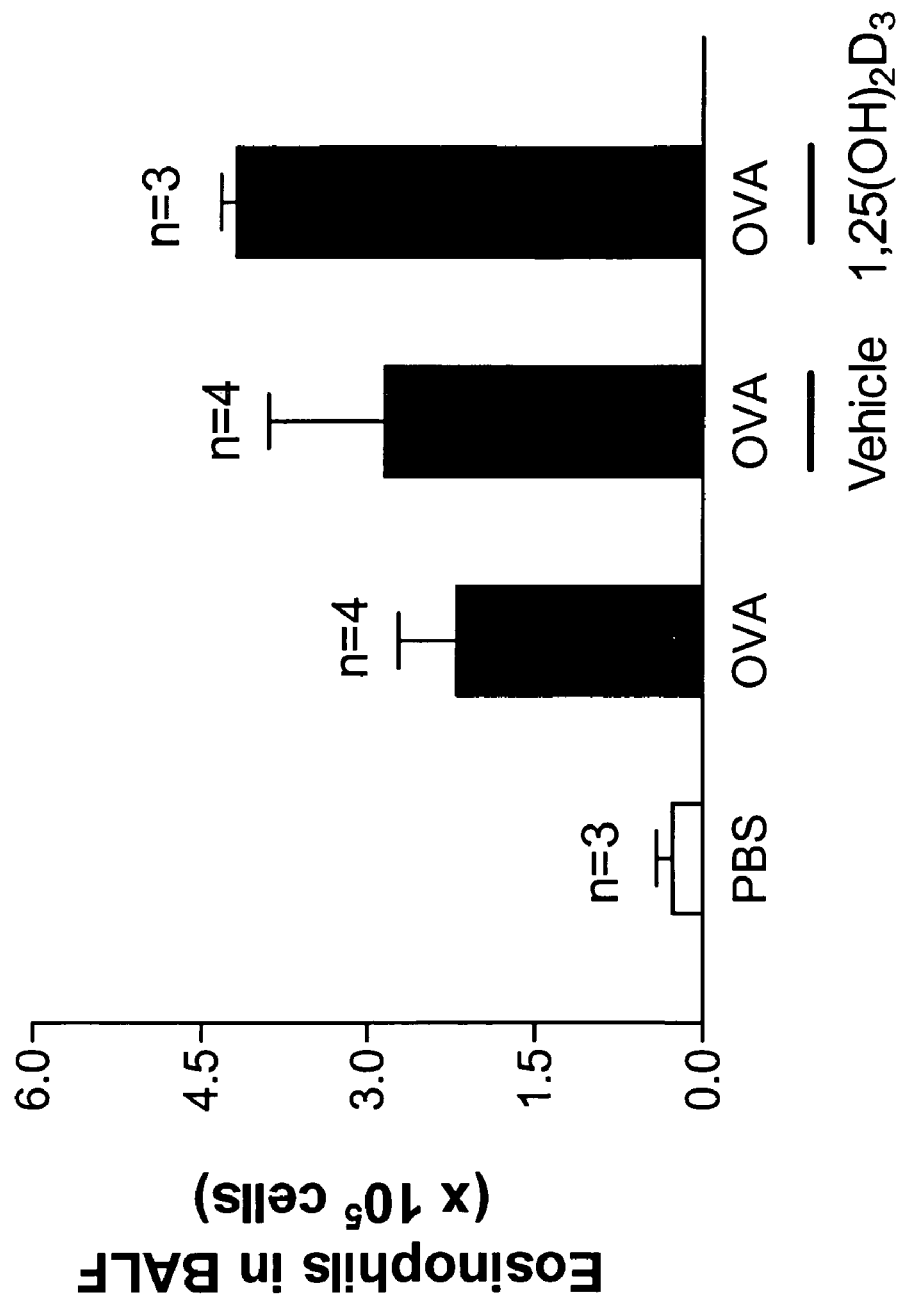
FIG. 11 is a bar graph of the number of eosinophils in BALF of Brown Norway rats after OVA-challenge. As shown, 1,25(OH)$_2$D$_3$ increases the OVA-induced eosinophils count in BALF compared to the control.

Brown Norway rats sensitized and challenged with OVA developed symptoms of allergic asthma as assessed by an increase in total cell counts and eosinophil number in BALF. The increase in total cell counts in BALF observed after OVA challenge was reduced by 1,25$(OH)_2D_3$ treatment (FIG. 9). 1,25$(OH)_2D_3$ also decreased the number of macrophages in BALF when compared to control (PBS) (FIG. 10). Moreover, 1,25$(OH)_2D_3$ increased OVA-induced eosinophils recruitment into the lungs (FIG. 11), suggesting that 1,25$(OH)_2D_3$ exacerbates OVA-induced inflammation in this animal model of allergic asthma.

All references cited herein are hereby incorporated by reference in their entirety and for all purposes as if fully set forth herein.

It is understood that the invention is not limited to the embodiments set forth herein for illustration, but embraces all such forms thereof as come within the scope of the following claims.

What is claimed is:

1. A compound of formula I, a tautomer of the compound, a pharmaceutically acceptable salt of the compound, or a pharmaceutically acceptable salt of the tautomer

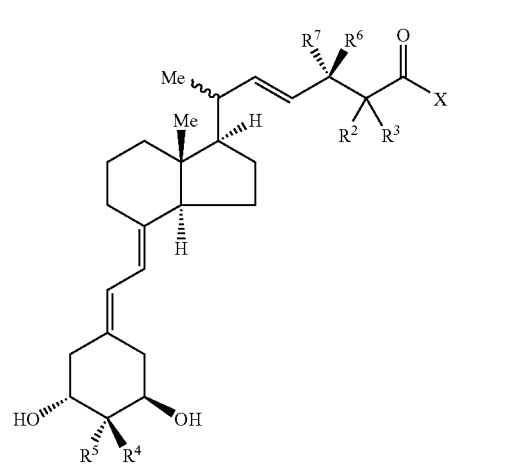

wherein

X is an $R^1$ group or is a group of formula —$OR^1$ wherein $R^1$ is a straight or branched chain alkyl group having 1 to 8 carbon atoms;

$R^2$ and $R^3$ are independently selected from H or straight or branched chain alkyl groups having 1 to 4 carbon atoms; or $R^2$ and $R^3$ join together to form a ring having 3 to 6 ring members;

$R^4$ is a straight or branched chain alkyl group having 1 to 6 carbon atoms;

$R^5$ is H; or $R^4$ and $R^5$ together represent a =$CH_2$ group; and $R^6$ is OH and $R^7$ is H; $R^6$ is an O-alkyl group and $R^7$ is H, wherein the alkyl group of the O-alkyl group is a straight or branched chain alkyl group having from 1 to 8 carbon atoms; or $R^6$ and $R^7$ together represent a =O group.

2. The compound of claim 1, wherein $R^6$ is OH and $R^7$ is H; or $R^6$ and $R^7$ together represent a =O group.

3. The compound of claim 2, wherein $R^4$ is a methyl group and $R^5$ is a H.

4. The compound of claim 2, wherein $R^4$ and $R^5$ together represent a =$CH_2$ group.

5. The compound of claim 2, wherein $R^2$ and $R^3$ are either both methyl groups, or $R^2$ and $R^3$ join together to form a cyclopropyl ring that includes the carbon to which they are both attached.

6. The compound of claim 2, wherein X is an $R^1$ group.

7. The compound of claim 2, wherein X is an —$OR^1$ group.

8. The compound of claim 2, wherein $R^6$ is OH and $R^7$ is H.

9. The compound of claim 2, wherein $R^6$ and $R^7$ together represent a =O group.

10. The compound of claim 2, wherein the compound has the formula IA

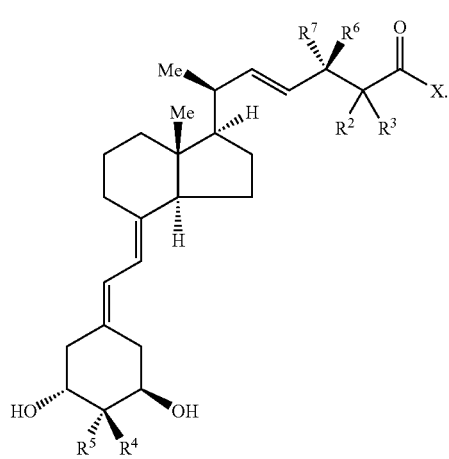

IA

11. The compound of claim 2, wherein the compound has the formula IB

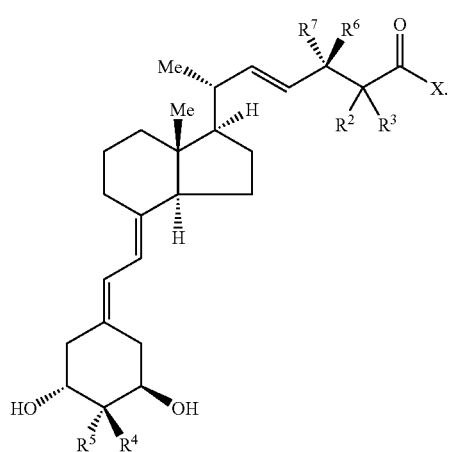

IB

12. The compound of claim 2, wherein the compound is a compound of formula II, formula III, formula IV, or formula V

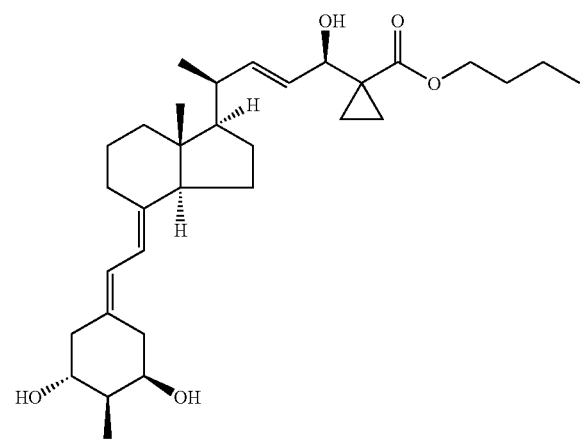

II

-continued

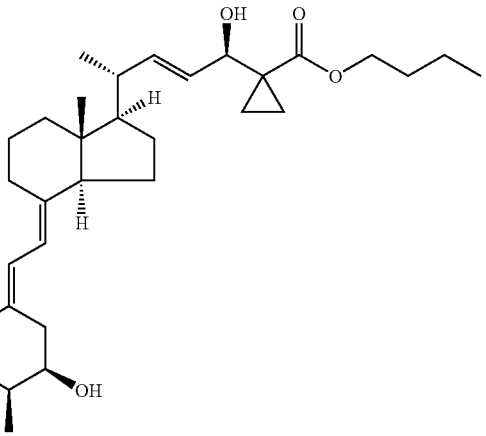

III

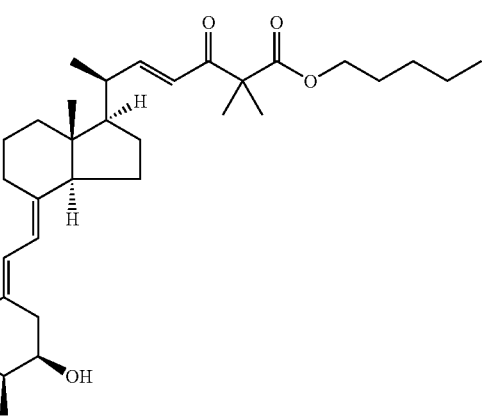

IV

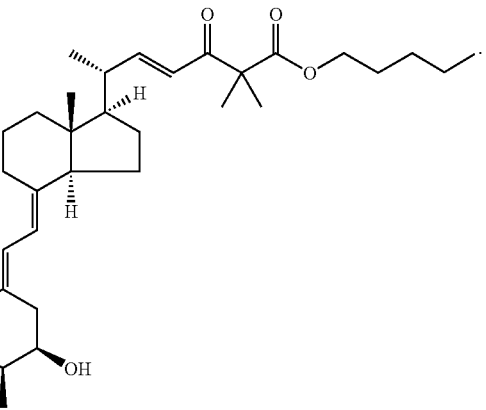

V

13. The compound of claim 2, wherein the compound is a compound of formula VI, formula VII, formula VIII, or formula IX

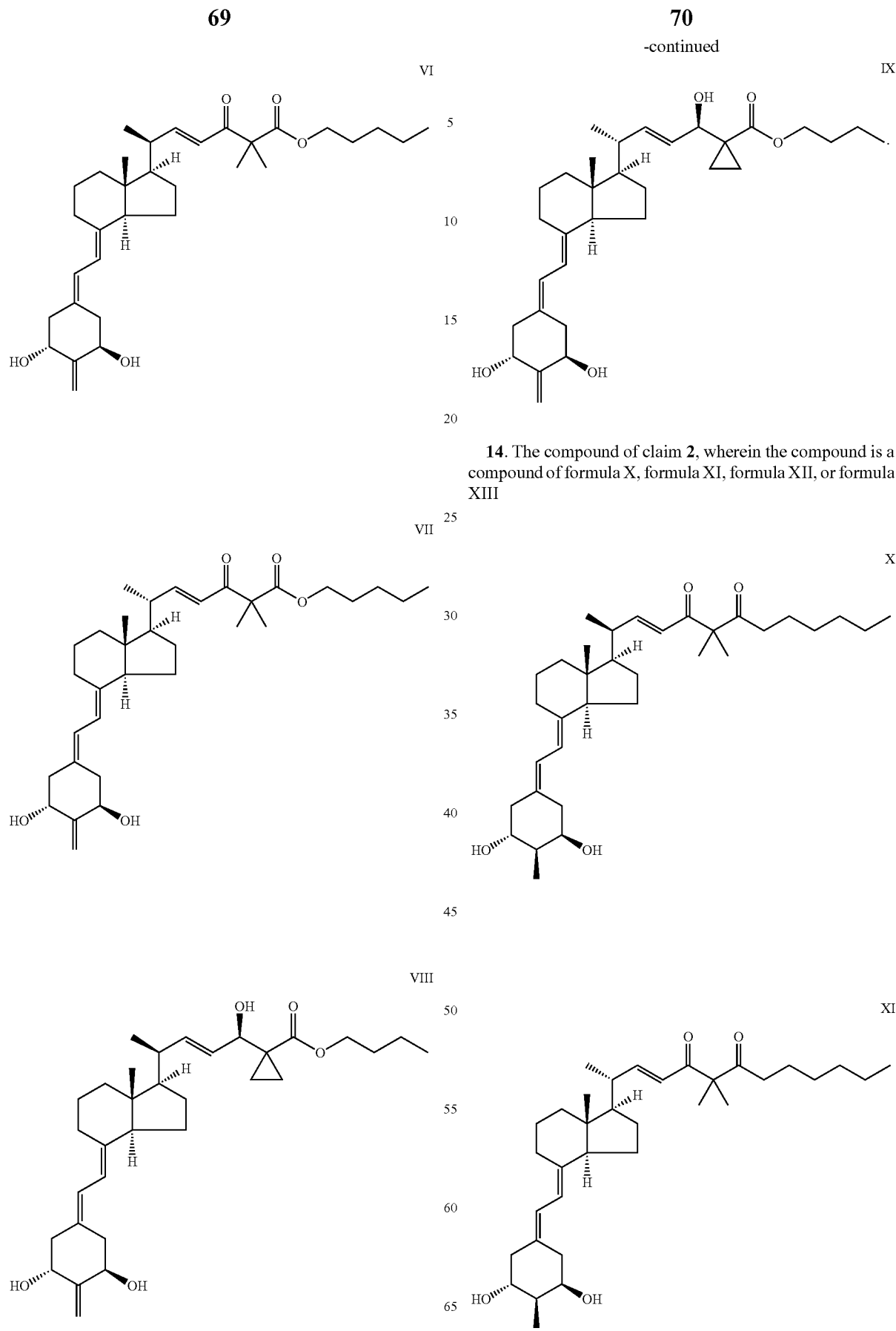
14. The compound of claim 2, wherein the compound is a compound of formula X, formula XI, formula XII, or formula XIII

XII

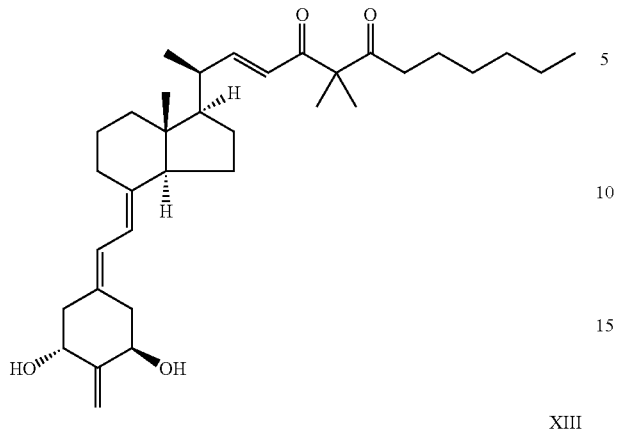

XIII

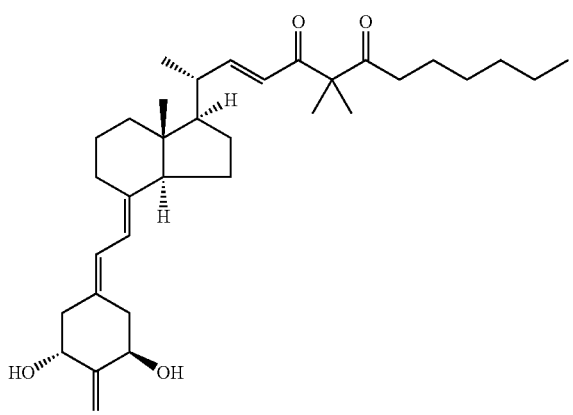

15. A pharmaceutical composition, comprising: the compound of claim 1, and a pharmaceutically acceptable carrier.

16. A method of antagonizing the vitamin D receptor, comprising administering an effective amount of the compound of claim 1 or a pharmaceutical composition comprising an effective amount of the compound of claim 1 to an animal subject, wherein the compound administered to the subject antagonizes the vitamin D receptor.

17. A method of treating asthma or eczema in an animal subject suffering from asthma or eczema, comprising administering an effective amount of the compound of claim 1 or a pharmaceutical composition comprising an effective amount of the compound of claim 1 to the animal subject.

18. The method of claim 17, wherein the compound is administered orally, parenterally, rectally, transdermally, or topically.

19. The method of claim 17, wherein the compound is administered by delivering the compound or pharmaceutical formulation in an aerosol.

20. The method of claim 19, wherein the aerosol is administered using an inhaler or a nebulizer.

21. A method of treating hypercalcemia, hyperparathyroidism, or vitamin D intoxication in an animal subject suffering from hypercalcemia, hyperparathyroidism, or vitamin D intoxication, comprising administering an effective amount of the compound of claim 1 or a pharmaceutical formulation comprising an effective amount of the compound of claim 1 to the animal subject.

22. A compound of formula XIV, a tautomer of the compound, a pharmaceutically acceptable salt of the compound, or a pharmaceutically acceptable salt of the tautomer

XIV

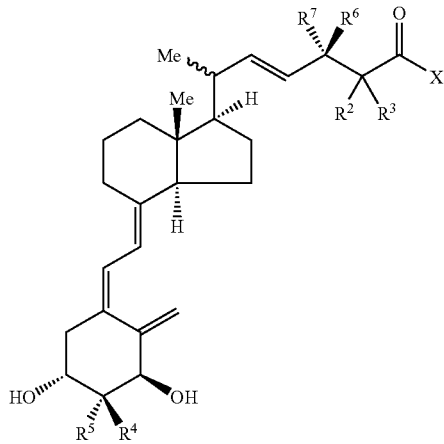

wherein
X is an $R^1$ group, wherein $R^1$ is a straight or branched chain alkyl group having 1 to 8 carbon atoms;
$R^2$ and $R^3$ are independently selected from H or straight or branched chain alkyl groups having 1 to 4 carbon atoms; or $R^2$ and $R^3$ join together to form a ring having 3 to 6 ring members;
$R^4$ is a straight or branched chain alkyl group having 1 to 6 carbon atoms;
$R^5$ is H;
$R^6$ is OH and $R^7$ is H; or $R^6$ and $R^7$ together represent a =O group.

23. The compound of claim 22, wherein $R^4$ is a methyl group.

24. The compound of claim 22, wherein $R^2$ and $R^3$ are either both methyl groups, or $R^2$ and $R^3$ join together to form a cyclopropyl ring that includes the carbon to which they are both attached.

25. The compound of claim 22, wherein $R^1$ is an ethyl, propyl, butyl, hexyl, or heptyl group.

26. The compound of claim 22, wherein $R^6$ is OH and $R^7$ is H.

27. The compound of claim 22, wherein $R^6$ and $R^7$ together represent a =O group.

28. The compound of claim 22, wherein the compound has the formula XIVA

XIVA

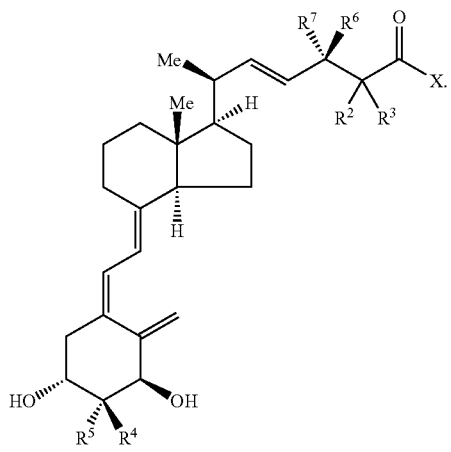

29. The compound of claim 22, wherein the compound has the formula XIVB

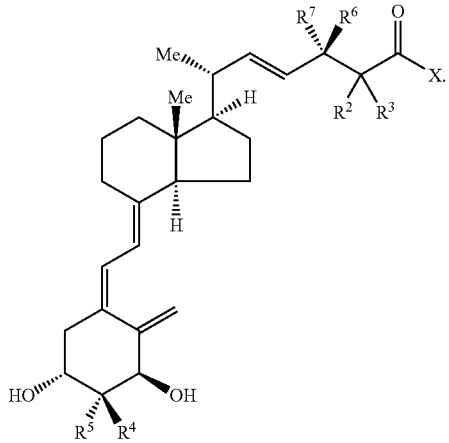

XIVB

30. The compound of claim 22, wherein the compound is a compound of formula XV, formula XVI, formula XVII, or formula XVIII

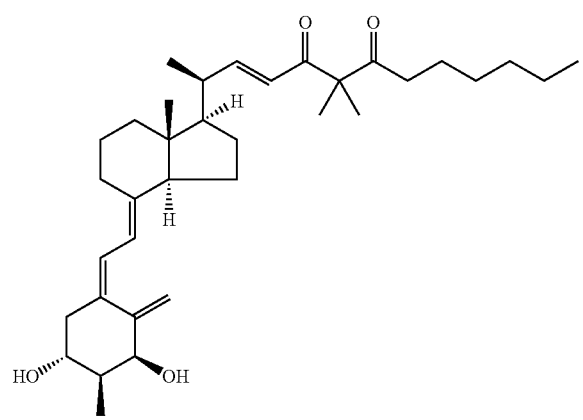

XV

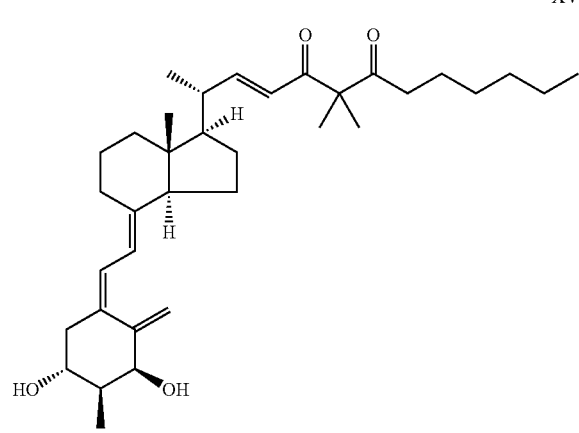

XVI

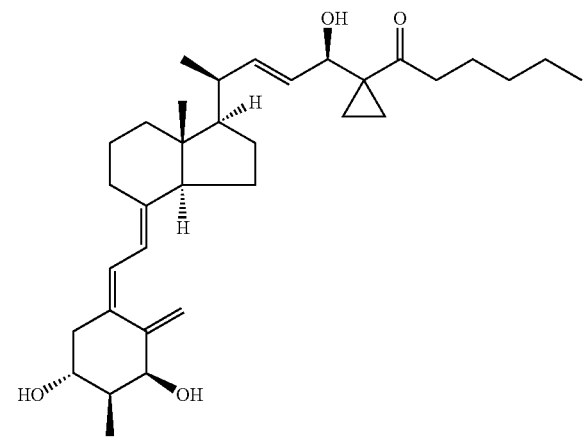

XVII

XVIII

31. A pharmaceutical composition, comprising: the compound of claim 22, and a pharmaceutically acceptable carrier.

32. A method of antagonizing the vitamin D receptor, comprising administering an effective amount of the compound of claim 22 or a pharmaceutical composition comprising an effective amount of the compound of claim 22 to an animal subject, wherein the compound administered to the subject antagonizes the vitamin D receptor.

33. A method of treating asthma or eczema in an animal subject suffering from asthma or eczema, comprising administering an effective amount of the compound of claim 22 or a pharmaceutical composition comprising an effective amount of the compound of claim 22 to the animal subject.

34. The method of claim 33, wherein the compound is administered orally, parenterally, rectally, transdermally, or topically.

35. The method of claim 33, wherein the compound is administered by delivering the compound or pharmaceutical formulation in an aerosol.

36. A method of treating hypercalcemia, hyperparathyroidism, or vitamin D intoxication in an animal subject suffering from hypercalcemia, hyperparathyroidism, sarcoidosis, or vitamin D intoxication, comprising administering an effective amount of the compound of claim 22 or a pharmaceutical formulation comprising an effective amount of the compound of claim 22 to the animal subject.

\* \* \* \* \*